United States Patent
Katayama et al.

(10) Patent No.: US 8,697,332 B2
(45) Date of Patent: Apr. 15, 2014

(54) BASE GENERATOR, PHOTOSENSITIVE RESIN COMPOSITION, PATTERN FORMING MATERIAL COMPRISING THE PHOTOSENSITIVE RESIN COMPOSITION, PATTERN FORMING METHOD USING THE PHOTOSENSITIVE RESIN COMPOSITION AND PRODUCTS COMPRISING THE SAME

(75) Inventors: Mami Katayama, Tokyo-to (JP); Shunji Fukuda, Tokyo-to (JP); Katsuya Sakayori, Tokyo-to (JP); Kouji Kawaguchi, Tokyo-to (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 0 days.

(21) Appl. No.: 13/259,586

(22) PCT Filed: Mar. 26, 2010

(86) PCT No.: PCT/JP2010/055431
§ 371 (c)(1),
(2), (4) Date: Dec. 2, 2011

(87) PCT Pub. No.: WO2010/113813
PCT Pub. Date: Oct. 7, 2010

(65) Prior Publication Data
US 2012/0070781 A1   Mar. 22, 2012

(30) Foreign Application Priority Data

Mar. 31, 2009 (JP) .................................. 2009-087617
Nov. 16, 2009 (JP) .................................. 2009-260753

(51) Int. Cl.
*G03F 7/004* (2006.01)
*G03F 7/038* (2006.01)
*G03F 7/20* (2006.01)
*G03F 7/30* (2006.01)
*G03F 7/38* (2006.01)

(52) U.S. Cl.
USPC ........ 430/270.1; 430/919; 430/920; 430/923; 430/280.1; 430/325; 430/330; 430/311; 430/9; 546/226; 546/207; 546/214; 546/14; 558/269; 558/270; 558/271; 558/272; 558/273; 564/170

(58) Field of Classification Search
None
See application file for complete search history.

(56) References Cited

U.S. PATENT DOCUMENTS

| 4,093,461 A | 6/1978 | Loprest et al. |
| 4,243,743 A | 1/1981 | Hiramoto et al. |
| 6,313,132 B1 * | 11/2001 | Johansson et al. ............ 514/277 |
| 2002/0048726 A1 * | 4/2002 | Kikkawa et al. ........... 430/283.1 |
| 2011/0086311 A1 | 4/2011 | Katayama et al. |

FOREIGN PATENT DOCUMENTS

| JP | 52-13315 A | 7/1976 |
| JP | 54-145794 A | 11/1979 |
| JP | 57-38759 | * 3/1982 |
| JP | 8-227154 A | 9/1996 |
| JP | 2003-212856 A | 7/2003 |
| JP | 2008-107409 A | 5/2008 |
| JP | 2009-080452 A | 4/2009 |
| WO | 2009/123122 A1 | 10/2009 |

OTHER PUBLICATIONS

Wang et al ("Coumarin-based Prodrugs. Part 3: Structural Effects on the Release Kinetics of Esterase-sensitive Prodrugs of Amines", Bioorganic & Medicinal Chemistry, vol. 6 (1998), p. 417-426).*
Eistert (Chemical Abstract No. 11946:35410, which is an abstract for "Relationship between "Substantivity" and Constitution of Compounds that are Substantives for Cotton", Annalen der Chemie, Justus Liebigs, vol. 556, p. 91-102 (1944)).*
Ajisawa et al (Chemical Abstract No. 1982:472095, which is an English abstract for JP 57-38759 (1982)).*
Liao et al ("The Effect of Phenyl Substituents on the Release Rates of Esterase-Sensitive Coumarin-Based Prodrugs", Chemical & Pharmaceutical Bulletin, vol. 48(8), p. 1138-1147 (2000)).*
Binghe Wang, et al; "A Photo-Sensitive Protecting Group for Amines Based on Coumarin Chemistry", Chemical and Pharmaceutical Bulletin, Apr. 1997, vol. 45, No. 4, p. 715-718.
Shunji Fukuda; "Photosensitive Polyimide using a Highly Sensitive Photobase Generator", Journal of Photopolymer Science and Technology, Aug. 14, 2009, vol. 22, No. 3, p. 391-392.
International Search Report: mailed Jun. 29, 2010; PCT/JP2010/055431.

* cited by examiner

Primary Examiner — Sin J. Lee
(74) Attorney, Agent, or Firm — Ladas & Parry LLP

(57) ABSTRACT

An object of the present invention is to provide a base generator which has sensitivity and is applicable to a wide range of applications, and a photosensitive resin composition which is applicable to a wide range of applications due to the structure of a polymer precursor in which reaction into a final product is promoted by a basic substance or by heating in the presence of a basic substance. The base generator generates a base by exposure to electromagnetic radiation and heating. The photosensitive resin composition comprises a polymer precursor in which reaction into a final product is promoted by the base generator and a basic substance or by heating in the presence of a basic substance.

10 Claims, No Drawings

BASE GENERATOR, PHOTOSENSITIVE RESIN COMPOSITION, PATTERN FORMING MATERIAL COMPRISING THE PHOTOSENSITIVE RESIN COMPOSITION, PATTERN FORMING METHOD USING THE PHOTOSENSITIVE RESIN COMPOSITION AND PRODUCTS COMPRISING THE SAME

TECHNICAL FIELD

The present invention relates to a base generator which generates a base by exposure to electromagnetic radiation and heating, and a photosensitive resin composition comprising the base generator. In particular, the present invention relates to the following: a photosensitive resin composition which can be suitably used as a material for products or components which are formed through a patterning process using electromagnetic radiation or through a curing acceleration process, a pattern forming material comprising the photosensitive resin composition, a pattern forming method, and an article comprising the resin composition.

BACKGROUND ART

A photosensitive resin composition is used as a material for forming electronic components, optical products or optical elements, a material for forming layers, an adhesive, etc. Particularly, it is suitably used for products or components which are formed through a patterning process using electromagnetic radiation.

For example, polyimide, which is a polymer material, exhibits top-ranking performance in properties such as heat resistance, dimensional stability and insulation property among organic materials. Thus, it is widely used as an insulation material for electronic components, etc., and it is increasingly and actively used as a chip coating film of semiconductor elements, a substrate of flexible printed-wiring boards, and so on.

Also in recent years, to solve problems with polyimide, intensive investigations have been carried out into polybenzoxazole having a low water absorption property a low dielectric constant, polybenzimidazole having excellent adhesion to substrates, and so on, which are processed in a similar manner to polyimide.

In general, polyimide shows poor solubility in solvents and is difficult to process. As the method for patterning polyimide in a desired shape, therefore, there is a method for obtaining a pattern of polyimide by patterning polyimide by exposure to light and development when it is in a state of polyimide precursor that has excellent solubility in solvents, and then imidizing the resultant by heating, etc.

Various methods are proposed for forming a pattern by using a polyimide precursor. Two typical examples are as follows:

(1) A method for forming a pattern by forming a resist layer comprising a photosensitive resin on a polyimide precursor which has no pattern forming ability (2) A method for forming a pattern by introducing a photosensitive site to a polyimide precursor by a bond or coordination and forming a pattern by its action, or a method for forming a pattern by mixing a polyimide precursor with a photosensitive component to produce a resin composition and forming a pattern by the action of the photosensitive component Typical patterning methods using method (2) include: (i) a method for obtaining a polyimide pattern in which a naphthoquinonediazide derivative which acts as a dissolution inhibitor before exposure to electromagnetic radiation and which produces a carboxylic acid and acts as a dissolution promoter after the exposure, is mixed with a polyimide precursor (polyamic acid) so that there is an increase in contrast between the dissolution rate of exposed regions in developers and that of unexposed regions in the same, thereby forming a pattern; thereafter, the pattern is imidized to obtain a polyimide pattern (patent literature 1) and (ii) a method for obtaining a polyimide pattern in which a methacryloyl group is introduced to a polyimide precursor via an ester bond or ionic bond; a photoradical generator is added thereto to crosslink exposed regions so that there is an increase in contrast between the dissolution rate of the exposed regions in developers and that of unexposed regions in the same, thereby forming a pattern; thereafter, the pattern is imidized to obtain a polyimide pattern (patent literature 2).

Compared with method (1), method (2) needs no resist layer, so that the process can significantly simplified. However, method (i) is problematic in that the original properties of polyimide cannot be obtained when the added amount of the naphthoquinonediazide derivative is increased for increasing the dissolution contrast. Method (ii) is problematic in that there is a limitation on the structure of the polyimide precursor.

There is a report of other patterning method (iii) which is a method for obtaining a polyimide pattern in which a polyimide precursor (polyamic acid) is mixed with a photobase generator; the mixture is exposed to light and then heated to promote cyclization by the action of bases generated by the exposure and thus to decrease the solubility of the polyimide precursor in developers so that there is an increase in contrast between the dissolution rate of exposed regions in developers and that of unexposed regions in the same, thereby forming a pattern; thereafter, the pattern is imidized to obtain a polyimide pattern (patent literature 3).

Other examples of the photosensitive resin composition comprising a photobase generator include a photosensitive resin composition comprising an epoxy compound (for example, patent literature 4). The photobase generator is exposed to light to generate amines in a layer that contains the epoxy compound, so that the amines act as an initiator or catalyst and cure the epoxy compound in exposed regions only, thereby forming a pattern.

CITATION LIST

Patent literature 1: Japanese Patent Application Laid-Open (JP-A) No. S52-13315
Patent literature 2: JP-A No. S54-145794
Patent literature 3: JP-A No. H8-227154
Patent literature 4: JP-A No. 2003-212856

SUMMARY OF INVENTION

Technical Problem

A photosensitive resin composition comprising a photobase generator can be produced by a simple process because a photosensitive polymer precursor can be obtained simply by mixing an existing polymer precursor with a photobase generator at a predetermined ratio. In particular, the photosensitive resin composition comprising the photobase generator provides the benefit of broad utility to polyimide precursors which conventionally have a limitation on the structure of usable precursor compounds because of applicability to polyimide precursors of various structures. However, conventional photobase generators are problematic in that since they have low sensitivity, a large amount of electromagnetic radiation is needed. They are also problematic in that a large electromagnetic radiation decreases throughput per unit time.

Also, there is a demand that in order to be applicable to more polymer precursors and compounds, a photobase generator has improved compatibility with the polymer precursors or the like depending on the structure of the polymer precursors or the like, appropriately. When a photobase generator has high compatibility with polymer precursors or the like, it can be dissolved with a polymer precursor or the like without using a solvent for example, so that it can be made into varnish.

Also, when a photobase generator has a phenolic hydroxyl group, there is a possibility that the phenolic hydroxyl group is reacted with an epoxy group by heating at 100° C. or more; therefore, there is a possibility that the phenolic hydroxyl group is reacted in a region which is not exposed to electromagnetic radiation. Therefore, there is an unpreferable case that a photobase generator having a phenolic hydroxyl group coexists with a polymer precursor, such as a photosensitive resin composition comprising a polymer precursor having an epoxy group.

The present invention was achieved in light of the above circumstances. A main object of the present invention is to provide a base generator which has excellent sensitivity and can be used in combination with a wide range of compounds, and a photosensitive resin composition which has excellent sensitivity, can be combined with any kind of polymer precursor and can form a well-shaped pattern.

Solution to Problem

A base generator of the present invention is represented by the following chemical formula (1) and generates a base by exposure to electromagnetic radiation and heating:

[Chemical formula 1]

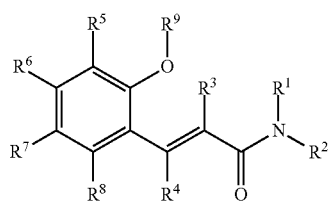

Formula (1)

wherein $R^1$ and $R^2$ are each independently a hydrogen or an organic group and may be the same or different; $R^1$ and $R^2$ may be bound to form a cyclic structure which may contain a heteroatom; at least one of $R^1$ and $R^2$ is an organic group; $R^3$ and $R^4$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group or an organic group and may be the same or different; $R^5$, $R^6$, $R^7$ and $R^8$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group or an organic group and may be the same or different; two or more of $R^5$, $R^6$, $R^7$ and $R^8$ may be bound to form a cyclic structure which may contain a heteroatom; and $R^9$ is a protecting group which can be deprotected by heating and/or exposure to electromagnetic radiation.

In the base generator of the present invention, $R^9$, which is a protecting group capable of being deprotected, is a silyl group, a silanol group, a phosphino group, a phosphinyl group, a phosphono group or a monovalent organic group.

In the base generator of the present invention, $R^9$ is preferably one or more kinds selected from the group consisting of organic groups represented by the following formulae (2-1) to (2-6), from the point of view that synthesis is easy and $R^9$ can be deprotected by heating and/or exposure to electromagnetic radiation:

[Chemical formula 2]

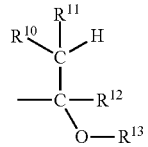

Formula (2-1)

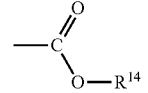

Formula (2-2)

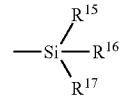

Formula (2-3)

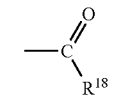

Formula (2-4)

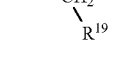

Formula (2-5)

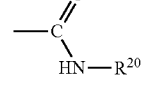

Formula (2-6)

wherein $R^{10}$, $R^{11}$ and $R^{12}$ in the formula (2-1) are each independently a hydrogen, a halogen or an organic group; $R^{13}$ in the formula (2-1) is an organic group; $R^{10}$, $R^{11}$, $R^{12}$ and $R^{13}$ may be bound to form a cyclic structure; $R^{14}$ in the formula (2-2) is an organic group; $R^{15}$, $R^{16}$ and $R^{17}$ in the formula (2-3) are each independently a hydrogen, a halogen or an organic group; $R^{18}$ in the formula (2-4) is an organic group; $R^{19}$ in the formula (2-5) is an aromatic ring which may have a substituent; and $R^{20}$ in the formula (2-6) is an organic group.

The photosensitive resin composition of the present invention comprises a polymer precursor in which reaction into a final product is promoted by a basic substance or by heating in the presence of a basic substance, and the base generator of the present invention.

The present invention also provides a pattern forming material comprising the photosensitive resin composition of the present invention.

The present invention also provides a pattern forming method using the photosensitive resin composition.

The pattern forming method of the present invention is characterized by forming a coating film or molded body with the photosensitive resin composition, exposing the coating film or molded body to electromagnetic radiation in a predetermined pattern, heating the coating film or molded body after or at the same time as the exposure to change the solubility of the exposed region, and then developing the coating film or molded body.

In the pattern forming method, the polymer precursor is used in combination with the base generator which is a compound as represented by the above formula (1); therefore, it is possible to form a pattern by development without using a resist film which is for protecting the surface of a coating film or molded body comprising a photosensitive resin composition from developers.

The present invention also provides an article selected from a printed product, a paint, a sealing agent, an adhesive, a display device, a semiconductor device, an electronic component, a microelectromechanical system, a stereolithography product, an optical element or a building material, at least part of each of which articles comprising any of the photosensitive resin composition or a cured product thereof.

Advantageous Effects of Invention

Because of having the structure represented by the formula (1), the base generator of the present invention generates a base by exposure to electromagnetic radiation and the base generation is promoted by heating, so that the base generator has greater sensitivity than conventionally-used photobase generators. In particular, by protecting the phenolic hydroxyl group with the protecting group which can be deprotected by heating and/or exposure to electromagnetic radiation and by appropriately selecting the protecting group, there is an increase in the compatibility of the base generator with compounds to be combined, such as a polymer precursor and an acid-base indicator, thereby expanding the range of compounds that can be used in combination or the range of application methods of the base generator. When used for a photosensitive resin composition, the base generator of the present invention can be used in combination with various kinds of polymer precursors.

The photosensitive resin composition of the present invention is a highly sensitive photosensitive resin composition because the base generator contained represented by the formula (1) has better sensitivity than conventionally-used photobase generators. The photosensitive resin composition of the present invention can form a well-shaped pattern because, when the photosensitive resin composition is subjected to exposure to electromagnetic radiation and heating, the solubility of the polymer precursor is changed by a base which is derived from the base generator.

Also in the photosensitive resin composition of the present invention, unlike acid, the base causes no metal corrosion; therefore, the photosensitive resin composition can form a more highly reliable cured film.

When a heating process is included in a pattern forming process, the photosensitive resin composition of the present invention can utilize the heating process as a heating for promoting base generation and thus is advantageous in that the amount of electromagnetic radiation can be decreased by the utilization of the heating process. Therefore, compared with conventional resin compositions which produce a base only by exposure to electromagnetic radiation, the photosensitive resin composition can realize process rationalization when it is used in a process that includes such a heating process.

DESCRIPTION OF EMBODIMENTS

Hereinafter, the present invention will be described in detail. In the present invention, (meth)acryloyl means acryloyl and/or methacryloyl. (Meth)acryl means acryl and/or methacryl. (Meth)acrylate means acrylate and/or methacrylate.

Also in the present invention, except when a specific wavelength is mentioned, electromagnetic radiation encompasses not only electromagnetic waves having wavelengths in the visible and non-visible regions but also particle beams such as an electron beam, and radiation or ionizing radiation, each of which is a collective term that includes electromagnetic waves and particle beams. In this description, exposure to electromagnetic radiation is also referred to as exposure to light. Electromagnetic waves having a wavelength of 365 nm, 405 nm and 436 nm may be referred to as i-line, h-line and g-line, respectively.

<Base Generator>

The base generator of the present invention is represented by the following chemical formula (1) and generates a base by exposure to electromagnetic radiation and heating:

[Chemical formula 3]

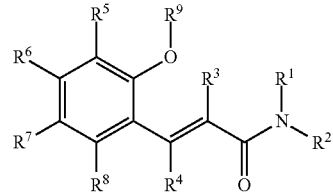

Formula (1)

wherein $R^1$ and $R^2$ are each independently a hydrogen or an organic group and may be the same or different; $R^1$ and $R^2$ may be bound to form a cyclic structure which may contain a heteroatom; at least one of $R^1$ and $R^2$ is an organic group; $R^3$ and $R^4$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group or an organic group and may be the same or different; $R^5$, $R^6$, $R^7$ and $R^8$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group or an organic group and may be the same or different; two or more of $R^5$, $R^6$, $R^7$ and $R^8$ may be bound to form a cyclic structure which may contain a heteroatom; and $R^9$ is a protecting group which can be deprotected by heating and/or exposure to electromagnetic radiation.

The base generator of the present invention is a kind of photobase generator. It generates a base only by exposure to electromagnetic radiation and the base generation is promoted by heating appropriately. The base generator of the present invention can generate a base efficiently by a combination of exposure to electromagnetic radiation and heating, with even a small amount of electromagnetic radiation. Therefore, it has higher sensitivity than conventional, so-called photobase generators. In particular, by protecting the phenolic hydroxyl group with the protecting group which can be deprotected by heating and/or exposure to electromagnetic radiation and by appropriately selecting the protecting group, there is an increase in the compatibility of the base generator with compounds to be combined, such as a polymer precursor and an acid-base indicator, thereby expanding the range of compounds that can be used in combination or the range of application methods of the base generator. For example, a polymer precursor which is not desired to coexist with a phenolic hydroxyl group can be used to coexist therewith in a resin composition by the base generator.

The base generator of the present invention has the above-specified structure; therefore, when it is exposed to electromagnetic radiation, as shown by the following formula, (—CR$^4$=CR$^3$—C(=O)—) in the formula (1) is isomerized from a trans isomer to a cis isomer. Moreover, the cis isomer is cyclized at the same time as that the protecting group R$^9$ is deprotected by heating and/or exposure to electromagnetic radiation, thereby generating a base (NHR$^1$R$^2$). By the catalytic action of the base thus generated, it is possible to decrease reaction initiation temperature at which a reaction of a polymer precursor into a final product is initiated, or it is possible to initiate a curing reaction of a polymer precursor into a final product.

[Chemical formula 4]

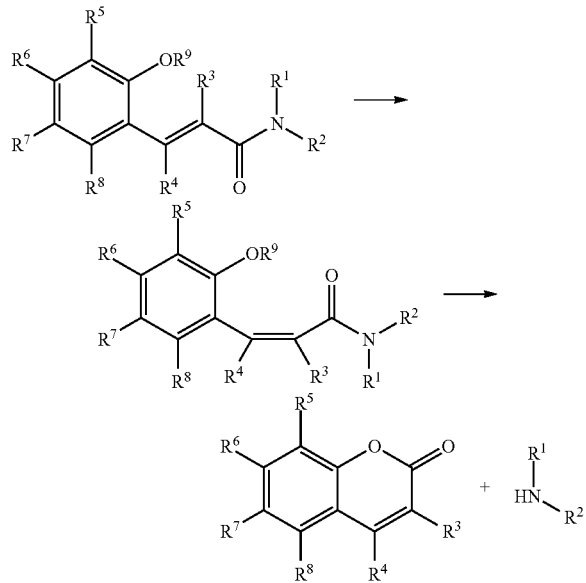

R$^1$ and R$^2$ are each independently a hydrogen atom or an organic group. At least one of R$^1$ and R$^2$ is an organic group. NHR$^1$R$^2$ is a base, and each of R$^1$ and R$^2$ is preferably an organic group containing no amino group. If an amino group is contained in R$^1$ and R$^2$, the base generator itself becomes a basic substance to promote the reaction of the polymer precursor, so that dissolution contrast between exposed and unexposed regions could be small. However, for example, as in the case where an amino group is bound to an aromatic ring that is present in the organic groups of R$^1$ and R$^2$, when there is a difference in basicity with a base generated after exposure to electromagnetic radiation and heating, it is sometimes possible to use the base generator even if an amino group is contained in the organic groups of R$^1$ and R$^2$.

Examples of the organic group include a saturated or unsaturated alkyl group, a saturated or unsaturated cycloalkyl group, an aryl group, an aralkyl group and a saturated or unsaturated alkyl halide group. These organic groups can contain a substituent or a bond other than a hydrocarbon group, such as a heteroatom, and they can be linear or branched.

When R$^1$ and R$^2$ are organic groups, they are generally monovalent organic groups. However, for example, when they form a cyclic structure described below or when the thus-generated NHR$^1$R$^2$ is a basic substance which has two or more NH groups that can form an amide bond each (e.g., diamine), they can be divalent or more organic groups.

R$^1$ and R$^2$ may be bound to form a cyclic structure.

The cyclic structure can be a saturated or unsaturated alicyclic hydrocarbon, a heterocyclic ring, a condensed ring, or a structure comprising a combination of two or more kinds selected from the group consisting of them.

The bond other than a hydrocarbon group in the organic groups of R$^1$ and R$^2$ is not particularly limited as long as the effects of the present invention are not deteriorated, and examples of the bond include an ether bond, a thioether bond, a carbonyl bond, a thiocarbonyl bond, an ester bond, an amide bond, an urethane bond, an imino bond (such as —N=C(—R)— or —C(=NR)— wherein R is a hydrogen atom or an organic group), a carbonate bond, a sulfonyl bond, a sulfinyl bond and an azo bond. From the viewpoint of heat resistance, preferred are an ether bond, a thioether bond, a carbonyl bond, a thiocarbonyl bond, an ester bond, an amide bond, an urethane bond, an imino bond (such as —N=C(—R)— or —C(=NR)— wherein R is a hydrogen atom or an organic group), a carbonate bond, a sulfonyl bond and a sulfinyl bond.

The substituent other than a hydrocarbon group in the organic groups of R$^1$ and R$^2$ is not particularly limited as long as the effects of the present invention are not deteriorated. Examples of the substituent include a halogen atom, a hydroxyl group, a mercapto group, a sulfide group, a cyano group, an isocyano group, a cyanato group, an isocyanato group, a thiocyanato group, an isothiocyanato group, a silyl group, a silanol group, an alkoxy group, an alkoxycarbonyl group, a carbamoyl group, a thiocarbamoyl group, a nitro group, a nitroso group, a carboxyl group, a carboxylate group, an acyl group, an acyloxy group, a sulfino group, a sulfo group, a sulfonato group, a phosphino group, a phosphinyl group, a phosphono group, a phosphonato group, a hydroxyimino group, a saturated or unsaturated alkyl ether group, a saturated or unsaturated alkylthioether group, an arylether group, an arylthioether group and an amino group (such as —NH$_2$, —NHR or —NRR' wherein R and R' are each independently a hydrocarbon group). A hydrogen contained in the above-mentioned substituent can be replaced by a hydrocarbon group. Moreover, a hydrocarbon group contained in the above-mentioned substituent can be linear, branched or cyclic.

Among them, preferred are a halogen atom, a hydroxyl group, a mercapto group, a sulfide group, a cyano group, an isocyano group, a cyanato group, an isocyanato group, a thiocyanato group, an isothiocyanato group, a silyl group, a silanol group, an alkoxy group, an alkoxycarbonyl group, a carbamoyl group, a thiocarbamoyl group, a nitro group, a nitroso group, a carboxyl group, a carboxylate group, an acyl group, an acyloxy group, a sulfino group, a sulfo group, a sulfonato group, a phosphino group, a phosphinyl group, a phosphono group, a phosphonato group, a hydroxyimino group, a saturated or unsaturated alkyl ether group, a saturated or unsaturated alkylthioether group, an arylether group and an arylthioether group.

The basic substance thus generated is NHR$^1$R$^2$, so that the examples include a primary amine, a secondary amine and a heterocyclic compound. Each of the amines encompasses an aliphatic amine and an aromatic amine. The said heterocyclic compound refers to NHR$^1$R$^2$ which has a cyclic structure and aromaticity. One that is not an aromatic heterocyclic compound, that is, a non-aromatic heterocyclic compound, is considered as alicyclic amine herein and included in aliphatic amines.

Furthermore, the thus-generated $NHR^1R^2$ can be a basic substance having only one NH group that can form an amide bond, such as a monoamine, or a basic substance having two or more NH groups that can form an amide bond, such as a diamine, triamine or tetraamine. When the thus-generated $NHR^1R^2$ is a basic substance having two or more NH groups, there may be mentioned a structure in which a photolatent site is further bound to one or more terminals of $R^1$ and/or $R^2$ in the formula (1), the site being able to generate a base having a NH group that can form an amide bond by exposure to electromagnetic radiation and heating. Examples of the photolatent site include a structure in which a residue of the formula (1) which excludes $R^1$ and/or $R^2$ is further bound to one or more terminals of $R^1$ and/or $R^2$ in the formula (1).

Examples of the aliphatic primary amine include methylamine, ethylamine, propylamine, isopropylamine, n-butylamine, sec-butylamine, tert-butylamine, pentylamine, isoamylamine, tert-pentylamine, cyclopentylamine, hexylamine, cyclohexylamine, heptylamine, cycloheptanamine, octylamine, 2-octanamine, 2,4,4-trimethylpentane-2-amine and cyclooctylamine.

Examples of the aromatic primary amine include aniline, 2-aminophenol, 3-aminophenol and 4-aminophenol.

Examples of the aliphatic secondary amine include dimethylamine, diethylamine, dipropylamine, diisopropylamine, dibutylamine, ethylmethylamine, aziridine, azetidine, pyrrolidine, piperidine, azepane, methylazetidine, dimethylazetidine, trimethylazetidine, methylpyrrolidine, dimethylpyrrolidine, trimethylpyrrolidine, tetramethylpyrrolidine, methylpiperidine, dimethylpiperidine, trimethylpiperidine, tetramethylpiperidine and pentamethylpiperidine. Preferred are alicyclic amines.

Examples of aromatic secondary amine include methylaniline, diphenylamine and N-phenyl-1-naphthylamine. From the viewpoint of basicity, the aromatic heterocyclic compound having an NH group(s) that can form an amide bond preferably has an imino bond (such as —N=C(—R)— or —C(=NR)— wherein R is a hydrogen atom or an organic group) in a molecule thereof, and the examples include imidazole, purine, triazole and derivatives thereof.

Amines having two or more amino groups include, for example, linear aliphatic alkylenediamines such as ethylenediamine, 1,3-propanediamine, 1,4-butanediamine, 1,5-pentanediamine, 1,6-hexanediamine, 1,7-heptanediamine, 1,8-octanediamine, 1,9-nonanediamine and 1,10-decanediamine; branched aliphatic alkylenediamines such as 1-butyl-1,2-ethanediamine, 1,1-dimethyl-1,4-butanediamine, 1-ethyl-1,4-butanediamine, 1,2-dimethyl-1,4-butanediamine, 1,3-dimethyl-1,4-butanediamine, 1,4-dimethyl-1,4-butanediamine and 2,3-dimethyl-1,4-butanediamine; polyethyleneamines represented by the general formula $NH_2(CH_2CH_2NH)_nH$ such as diethylenetriamine, triethylenetetramine and tetraethylenepentamine; alicyclic diamines such as cyclohexanediamine, methylcyclohexanediamine, isophoronediamine, norbornanedimethylamine, tricyclodecanedimethylamine and menthenediamine; aromatic diamines such as p-phenylenediamine, m-phenylenediamine, p-xylylenediamine, m-xylylenediamine, 4,4'-diaminodiphenylmethane and diaminodiphenylsulfone; triamines such as benzenetriamine, melamine and 2,4,6-triaminopyrimidine; and tetraamines such as 2,4,5,6-tetraminopyrimidine.

The thermophysical properties and basicity of the basic substance thus generated vary depending on the substituents introduced in the positions of $R^1$ and $R^2$.

A basic substance with larger basicity provides more effective catalytic action such as decreasing the reaction initiation temperature at which the polymer precursor is reacted into a final product. Therefore, by the addition of the basic substance in a small amount, it is possible to initiate the reaction into a final product at a lower temperature. In general, secondary amines have higher basicity than primary amines and exert large catalytic effects.

Aliphatic amines have higher basicity than aromatic amines and thus are preferred.

The base thus generated in the present invention is preferably a secondary amine and/or a heterocyclic compound because the sensitivity of the base generator is increased. This is supposed to be because there is no active hydrogen at the amide-binding site by using a secondary amine and/or a heterocyclic compound, so that there is a change in electron density and thus an increase in isomerization sensitivity.

From the viewpoint of thermophysical properties and basicity of the base to be eliminated, preferably, the organic groups of $R^1$ and $R^2$ are each independently an organic group having 1 to 20 carbon atoms, more preferably an organic group having 1 to 12 carbon atoms, and particularly preferably an organic group having 1 to 8 carbon atoms.

A base generated from the base generator represented by the chemical formula (1) preferably has one NH group that can form an amide bond. When the base thus generated has two or more NH groups that can form an amide bond, the base generator has two or more amide bonds which will be cut by exposure to electromagnetic radiation and heating, so that two or more light-absorbing groups are present in one molecule, such as cinnamic acid derivative residues. Generally in this case, there is a problem of deterioration in solvent solubility due to an increase in molecular weight. When there are two or more light-absorbing groups in a molecule, a base is generated by cutting one of the amide bonds, each of which binds a base to light-absorbing groups. However, a base still having a light-absorbing group has a large molecular weight, resulting in poor diffusivity and thus obtaining poor sensitivity when used as the base generator. Moreover, when there is one light-absorbing group in one molecule, an excessive amount of relatively-inexpensive base is added in to synthesize the base generator; however, when there are two or more light-absorbing groups, it is necessary to add an excessive amount of relatively expensive material for the light-absorbing groups. In the case of the base having two or more NH groups that can form an amide bond, there is a problem of difficulty in purification after the synthesis. Particularly in the case of being combined with a polyimide precursor or polybenzoxazole precursor, preferred is the base which has one NH group that can form an amide bond.

In the case of combining with an epoxy compound, as the base generated from the base generator represented by the chemical formula (1), one having two or more NH groups that can form an amide bond can be suitably used because it can act as not only a curing accelerator but also a curing agent.

In the chemical formula (1), $R^3$ and $R^4$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group or an organic group and may be the same or different.

In the present invention, when at least one of $R^3$ and $R^4$ of the chemical formula (1) is not a hydrogen and is the above-specified functional group, it is possible for the base generator of the present invention to increase the solubility in organic solvents or the affinity for polymer precursors further, compared to the case where both $R^3$ and $R^4$ are hydrogens. For example, when at least one of $R^3$ and $R^4$ is an organic group such as an alkyl group or aryl group, the solubility in organic solvents is increased. When at least one of $R^3$ and $R^4$ is a halogen (e.g., fluorine), the affinity for polymer precursors containing a halogen (e.g., fluorine) is increased. When at least one of $R^3$ and $R^4$ has a silyl group or silanol group, the affinity for polysiloxane precursors is increased. As is described, by appropriately introducing a substituent to $R^3$ and/or $R^4$ depending on a desired organic solvent or polymer precursor, it is possible to increase the solubility in the desired organic solvent or the affinity for the desired polymer precursor.

The halogen and organic group are not particularly limited as long as the effects of the present invention are not deteriorated, and there may be used those that are the same as those listed below in connection with $R^5$, $R^6$, $R^7$ and $R^8$. As the bond and substituent other than a hydrocarbon group in the organic groups of $R^3$ and $R^4$, there may be used those that are the same as those listed below in connection with $R^5$, $R^6$, $R^7$ and $R^8$.

In general, the organic groups of $R^3$ and $R^4$ are monovalent organic groups.

$R^3$ and $R^4$ can be hydrogen atoms; however, when $R^3$ and $R^4$ have a substituent, at least one of them is preferably an alkyl group having 1 to 20 carbon atoms, such as a methyl group, an ethyl group or a propyl group; a cycloalkyl group having 4 to 23 carbon atoms, such as a cyclopentyl group or a cyclohexyl group; a cycloalkenyl group having 4 to 23 carbon atoms, such as a cyclopentenyl group or a cyclohexenyl group; an aryloxyalkyl group having 7 to 26 carbon atoms (—ROAr group), such as a phenoxymethyl group, a 2-phenoxyethyl group or a 4-phenoxybutyl group; an aralkyl group having 7 to 20 carbon atoms, such as a benzyl group or a 3-phenylpropyl group; an alkyl group having a cyano group and 2 to 21 carbon atoms, such as a cyanomethyl group or a O-cyanoethyl group; an alkyl group having a hydroxyl group and 1 to 20 carbon atoms, such as a hydroxymethyl group, an alkoxy group having 1 to 20 carbon atoms, such as a methoxy group or an ethoxy group, an amide group having 2 to 21 carbon atoms, such as an acetamide group or a benzenesulfonamide group ($C_6H_5SO_2NH_2$—), an alkylthio group having 1 to 20 carbon atoms (—SR group), such as a methylthio group or an ethylthio group, an acyl group having 1 to 20 carbon atoms, such as an acetyl group or a benzoyl group, an ester group having 2 to 21 carbon atoms (—COOR group or —OCOR group), such as a methoxycarbonyl group or an acetoxy group, an aryl group having 6 to 20 carbon atoms, such as a phenyl group, a naphthyl group, a biphenyl group or a tolyl group, an aryl group having 6 to 20 carbon atoms with substitution of an electron-donating group and/or an electron-attracting group, a benzyl group with substitution of an electron-donating group and/or an electron-attracting group, a cyano group or a methylthio group (—$SCH_3$). The alkyl sites can be linear, branched or cyclic.

In the chemical formula (1), $R^5$, $R^6$, $R^7$ and $R^8$ are each independently a hydrogen, a halogen, a hydroxyl group, a mercapto group, a sulfide group, a silyl group, a silanol group, a nitro group, a nitroso group, a sulfino group, a sulfa group, a sulfonato group, a phosphino group, a phosphinyl group, a phosphono group, a phosphonato group, an amino group, an ammonia group or an organic group and may be the same or different. Two or more of $R^5$, $R^6$, $R^7$ and $R^8$ may be bound to form a cyclic structure which may contain a heteroatom.

Examples of the halogen include a fluorine, a chlorine and a bromine.

The organic group is not particularly limited as long as the effects of the present invention are not deteriorated. Examples of the organic group include a saturated or unsaturated alkyl group, a saturated or unsaturated cycloalkyl group, an aryl group, an aralkyl group, a saturated or unsaturated alkyl halide group, a cyano group, an isocyano group, a cyanato group, an isocyanato group, a thiocyanato group, an isothiocyanato group, an alkoxy group, an alkoxycarbonyl group, a carbamoyl group, a thiocarbamoyl group, a carboxyl group, a carboxylate group, an acyl group, an acyloxy group and a hydroxyimino group. These organic groups can contain a substituent or a bond other than a hydrocarbon group, such as a heteroatom, and they can be linear or branched.

When $R^5$ to $R^8$ are organic groups, they are generally monovalent organic groups. However, for example, when they form a cyclic structure described below, they can be divalent or more organic groups.

The bond other than a hydrocarbon group in the organic groups of $R^5$ to $R^8$ is not particularly limited as long as the effects of the present invention are not deteriorated, and examples of the bond include an ether bond, a thioether bond, a carbonyl bond, a thiocarbonyl bond, an ester bond, an amide bond, an urethane bond, an imino bond (such as —N=C(—R)— or —C(=NR)— wherein R is a hydrogen atom or an organic group), a carbonate bond, a sulfonyl bond, a sulfinyl bond and an azo bond.

From the viewpoint of heat resistance, preferred are an ether bond, a thioether bond, a carbonyl bond, a thiocarbonyl bond, an ester bond, an amide bond, an urethane bond, an imino bond (such as —N=C(—R)— or —C(=NR)— wherein R is a hydrogen atom or an organic group), a carbonate bond, a sulfonyl bond and a sulfinyl bond.

The substituent other than a hydrocarbon group in the organic groups of $R^5$ to $R^8$ is not particularly limited as long as the effects of the present invention are not deteriorated. Examples of the substituent include a halogen atom, a hydroxyl group, a mercapto group, a sulfide group, a cyano group, an isocyano group, a cyanato group, an isocyanato group, a thiocyanato group, an isothiocyanato group, a silyl group, a silanol group, an alkoxy group, an alkoxycarbonyl group, a carbamoyl group, a thiocarbamoyl group, a nitro group, a nitroso group, a carboxyl group, a carboxylate group, an acyl group, an acyloxy group, a sulfino group, a sulfo group, a sulfonato group, a phosphino group, a phosphinyl group, a phosphono group, a phosphonato group, a hydroxyimino group, a saturated or unsaturated alkyl ether group, a saturated or unsaturated alkylthioether group, a saturated or unsaturated arylether group, a saturated or unsaturated arylthioether group, an amino group (such as —NH2, —NHR or —NRR' wherein R and R' are each independently a hydrocarbon group) and an ammonio group. A hydrogen contained in the above-mentioned substituent can be replaced by a hydrocarbon group. Moreover, a hydrocarbon group contained in the above-mentioned substituent can be linear, branched or cyclic.

Among them, preferred are a halogen atom, a hydroxyl group, a mercapto group, a sulfide group, a cyano group, an isocyano group, a cyanato group, an isocyanato group, a thiocyanato group, an isothiocyanato group, a silyl group, a silanol group, an alkoxy group, an alkoxycarbonyl group, a carbamoyl group, a thiocarbamoyl group, a nitro group, a nitroso group, a carboxyl group, a carboxylate group, an acyl group, an acyloxy group, a sulfino group, a sulfo group, a sulfonato group, a phosphino group, a phosphinyl group, a phosphono group, a phosphonato group, a hydroxyimino group, a saturated or unsaturated alkyl ether group, a saturated or unsaturated alkylthioether group, a saturated or unsaturated arylether group and a saturated or unsaturated arylthioether group.

Two or more of $R^5$, $R^6$, $R^7$ and $R^8$ may be bound to form a cyclic structure.

The cyclic structure can be a saturated or unsaturated alicyclic hydrocarbon, a heterocycle, a condensed ring or a structure comprising a combination of two or more kinds selected from the group consisting of them. For example, two or more of $R^5$ to $R^8$ may be bound to form a condensed ring such as naphthalene, anthracene, phenanthrene or indene, sharing an atom of the benzene ring to which $R^5$ to $R^8$ are bound.

In the present invention, it is preferable that one or more substituents are introduced to the substituents $R^5$ to $R^8$ of the present invention. That is, at least one of $R^5$, $R^6$, $R^7$ and $R^8$ is preferably a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group or an organic group. By introducing at least one substituent as just described to the substituents $R^5$ to $R^8$, it is possible to control the wavelength of absorbed light; moreover, the base generator is allowed to absorb a desired wavelength by the introduction of the substituent. By the introduction of the substituent which can elongate the conjugated chain of an aromatic ring, it is possible to shift the absorption wavelength to a longer wavelength side. It is also possible to increase the solubility or the compatibility with the polymer precursor to be combined. Thereby, it is possible to increase the sensitivity of the photosensitive resin composition considering the absorption wavelength of the polymer precursor to be combined.

As a guideline for determining what substituent can be introduced to shift the absorption wavelength to a desired wavelength side, "Interpretation of the Ultraviolet Spectra of Natural Products" (A. I. Scott 1964) and tables mentioned in "Spectrometric Identification of Organic Compounds, Fifth Edition" (R. M. Silverstein 1993) can be used.

Preferred as $R^5$ to $R^8$ are an alkyl group having 1 to 20 carbon atoms, such as a methyl group, an ethyl group or a propyl group; a cycloalkyl group having 4 to 23 carbon atoms, such as a cyclopentyl group or a cyclohexyl group; a cycloalkenyl group having 4 to 23 carbon atoms, such as a cyclopentenyl group or a cyclohexenyl group; an aryloxyalkyl group having 7 to 26 carbon atoms (—ROAr group), such as a phenoxymethyl group, a 2-phenoxyethyl group or a 4-phenoxybutyl group; an aralkyl group having 7 to 20 carbon atoms, such as a benzyl group or a 3-phenylpropyl group; an alkyl group having a cyano group and 2 to 21 carbon atoms, such as a cyanomethyl group or a β-cyanoethyl group; an alkyl group having a hydroxyl group and 1 to 20 carbon atoms, such as a hydroxymethyl group, an alkoxy group having 1 to 20 carbon atoms, such as a methoxy group or an ethoxy group, an amide group having 2 Lo 21 carbon atoms, such as an acetamide group or a benzenesulfonamide group ($C_6H_5SO_2NH_2$—), an alkylthio group having 1 to 20 carbon atoms (—SR group), such as a methylthio group or an ethylthio group, an acyl group having 1 to 20 carbon atoms, such as an acetyl group or a benzoyl group, an ester group having 2 to 21 carbon atoms (—COOR group or —OCOR group), such as a methoxycarbonyl group or an acetoxy group, an aryl group having 6 to 20 carbon atoms, such as a phenyl group, a naphthyl group, a biphenyl group or a tolyl group, an aryl group having 6 to carbon atoms with substitution of an electron-donating group and/or an electron-attracting group, a benzyl group with substitution of an electron-donating group and/or an electron-attracting group, a cyano group, or a methylthio group (—$SCH_3$). The alkyl sites can be linear, branched or cyclic.

It is also preferable that two or more of $R^5$ to $R^8$ are bound to form a condensed ring such as naphthalene, anthracene ring, phenanthrene ring or indene, sharing the atom of the benzene ring to which $R^5$ to $R^8$ are bound, so that the absorption wavelength of the base generator is shifted to a longer wavelength side.

It is also preferable that at least one of $R^5$, $R^6$, $R^7$ and $R^8$ is a hydroxyl group the base generator of the present invention, so that compared to a compound in which no hydroxyl group is contained in $R^5$, $R^6$, $R^7$ and $R^8$, the solubility in basic aqueous solutions or the like can be increased, and the absorption wavelength can be shifted to a longer wavelength side. It is particularly preferable that $R^8$ is a phenolic hydroxyl group because there is an increase in the number of reaction sites which are reacted when cyclization of a compound isomerized to a cis isomer takes place, so that the compound is likely to be cyclized.

From the viewpoint of obtaining excellent sensitivity, it is preferable that among $R^5$ to $R^8$, any of $R^5$ and $R^6$, $R^6$ and $R^7$, $R^7$ and $R^8$, and $R^5$ and $R^6$ and $R^7$ and $R^8$ have a partial structure represented by the formula (3):

[Chemical formula 5]

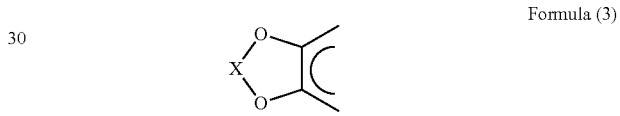

Formula (3)

wherein X is a linking group that can bound to two oxygen atoms.

The —O—X—O— part has a structure in which two substituents which are effective in shifting the absorption wavelength to a longer wavelength side and which are similar to alkoxy groups, are introduced in two adjacent positions of the 3- to 6-positions of the benzene ring and are bound to each other. Therefore, oxygen atoms are fixed to the base generator as a result of binding to the —O—X—O— part, so that the base generator having such substituents is supposed to be able to efficiently shift the absorption wavelength to a longer wavelength side, to generate a basic substance with a small amount of electromagnetic radiation, and to increase the sensitivity, compared to the case where two alkoxy groups are introduced in two adjacent positions of the 3- to 6-positions of a benzene ring.

X in the partial structure represented by the chemical formula (3) is not particularly limited as long as it is a linking group that can bound to two oxygen atoms.

In the present invention, from the viewpoint of obtaining high sensitivity, X is preferably a linking group selected from the group consisting of: a linear, branched or cyclic, saturated or unsaturated, aliphatic or aromatic hydrocarbon group which has 1 to 20 carbon atoms and which can contain a heteroatom and/or have a substituent; a linear, branched or cyclic hydrogen silicide group which has 1 to 20 silicon atoms, which can contain a heteroatom and/or have a substituent, and which can contain a silicon-silicon double bond; an ether bond; a thioether bond; a carbonyl bond; a thiocarbonyl bond; an ester bond; an amide bond; an urethane bond; a carbonate bond; a sulfonyl bond; and combinations thereof.

When X is a linear, branched or cyclic saturated aliphatic hydrocarbon group, the hydrocarbon group can have a heteroatom and/or a substituent. Examples of the saturated aliphatic hydrocarbon group include alkylene groups such as a methylene group, an ethylene group, a trimethylene group, a tetramethylene group, a pentamethylene group, a hexylene group, a decylene group, a dodecylene group, a hexadecylene group and an octadecylene groups; an ethylidene group and a propylidene group; and cycloalkylene groups such as a cyclohexylene group, a norbornanylene group and an adamantylene group.

When X is a linear, branched or cyclic unsaturated aliphatic hydrocarbon group, the hydrocarbon group can have a heteroatom and/or a substituent. Examples of the unsaturated aliphatic hydrocarbon group include a vinylene group.

Examples of the substituent of the saturated and unsaturated aliphatic hydrocarbon groups can be the same as the above-listed examples of the substituent other than a hydrocarbon group in the organic groups of $R^5$ Lo $R^8$.

Examples of the case where the saturated or unsaturated aliphatic hydrocarbon group has a heteroatom include a case where the saturated or unsaturated aliphatic hydrocarbon group has an ether bond, a thioether bond, a carbonyl bond, a thiocarbonyl bond, an ester bond, an amide bond, an urethane bond, a carbonate bond, a sulfonyl bond or the like.

When X is an aromatic hydrocarbon group, the aromatic hydrocarbon group can have a heteroatom and/or a substituent. Examples of the aromatic hydrocarbon group include a phenylene group and a naphthylene group.

Examples of the substituent of the aromatic hydrocarbon group can be the same as the substituents of the saturated aliphatic hydrocarbon group.

When the aromatic hydrocarbon group has a heteroatom (heterocyclic ring), specific examples thereof include furan and thiophene.

When X is a linear, branched or cyclic hydrogen silicide group, the hydrogen silicide group can have a heteroatom and/or a substituent. It can also have a silicon-silicon double bond.

In the present invention, "hydrogen silicide group" is a group consisting only of silicon and hydrogen. When it is a divalent hydrogen silicide group, it is —(SiH$_2$)$_n$—. When it is a monovalent hydrogen silicide group, it is —(SiH$_2$)$_n$—H. In these silicons, n is a natural number of 1 or more.

Examples of the substituent that the hydrogen silicide group can have include a halogen atom, a hydroxyl group and an organic group. These substituents can be the same as those listed above in connection with $R^5$ to $R^8$.

When the hydrogen silicide group has a heteroatom, examples of the bond contained in X include those listed above in connection with the saturated aliphatic hydrocarbon group.

More preferably, the partial structure represented by the chemical formula (3) is a partial structure represented by the following chemical formula (4):

[Chemical formula 6]

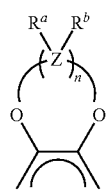

Formula (4)

wherein Z is a carbon atom, a silicon atom, a carbon-carbon double bond (—C=C—) or a silicon-silicon double bond (—Si=Si—); $R^a$ and $R^b$ are each independently a hydrogen, a halogen atom, a hydroxyl group, a nitro group, a nitroso group, a mercapto group, a silanol group, a monovalent hydrogen silicide group that may have a substituent, a phosphino group, a phosphinyl group, a phosphono group or an organic group; $R^a$ and $R^b$ can be the same or different; $R^a$ and $R^b$ can be bound to form a cyclic structure and can contain a heteroatom; and n is an integer of 1 to 10.

The cyclic structure which is formed when $R^a$ is bound to $R^b$ can be a saturated or unsaturated alicyclic hydrocarbon, a hetero ring, an aromatic hydrocarbon, or a structure comprising a combination of two or more kinds selected from the group consisting of them.

For example, when Z is a carbon atom, any two of n $R^a$(s) and n $R^b$(s) can be bound to form an alicyclic hydrocarbon or hetero ring. When Z is a carbon-carbon double bond, $R^a$ and $R^b$ can form a cyclic structure in combination with Z (carbon-carbon double bond), thereby forming an aromatic ring.

When Z is a silicon atom, each of n $R^a$(s) and n $R^b$(s) can be an organic group, and carbon atoms of the organic groups can be bound to form a cyclic structure. Or, each of n $R^a$(s) and n $R^b$(s) can be a hydrogen silicide group which may have a substituent, and silicon atoms of the hydrogen silicide groups can be bound to form a cyclic structure. The cyclic structure can include a heteroatom such as oxygen.

When Z is a silicon-silicon double bond, carbon atoms/and or silicon atoms of n $R^a$(s) and n $R^b$(s) can form a cyclic structure in combination with Z (silicon-silicon double bond), and the cyclic structure can further include a silicon-silicon double bond.

The halogen atom and organic group of $R^a$ and $R^b$ may be the same as those listed above in connection with $R^5$ to $R^8$.

As described above, n is an integer of 1 to 10. It is preferably an integer of 1 to 6, more preferably an integer of 1 to 3.

The following are examples of the partial structure represented by the formula (3). However, the partial structure is not limited to these examples.

[Chemical formula 7]

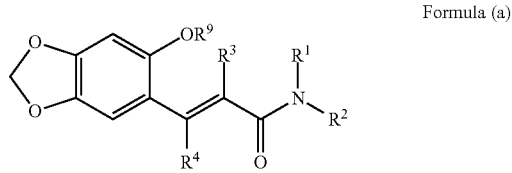

Formula (a)

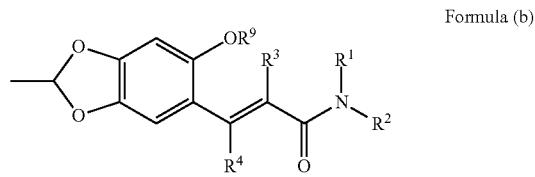

Formula (b)

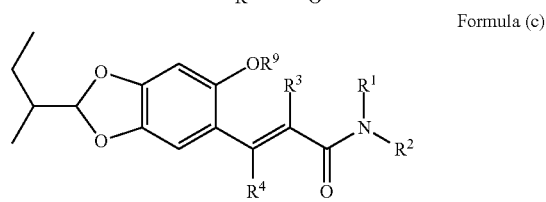

Formula (c)

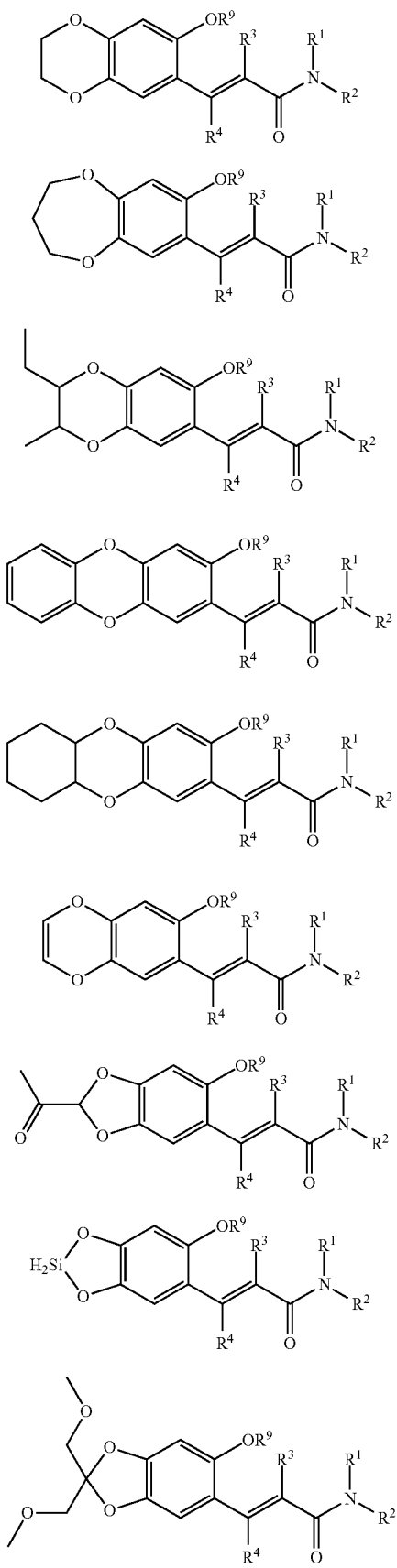
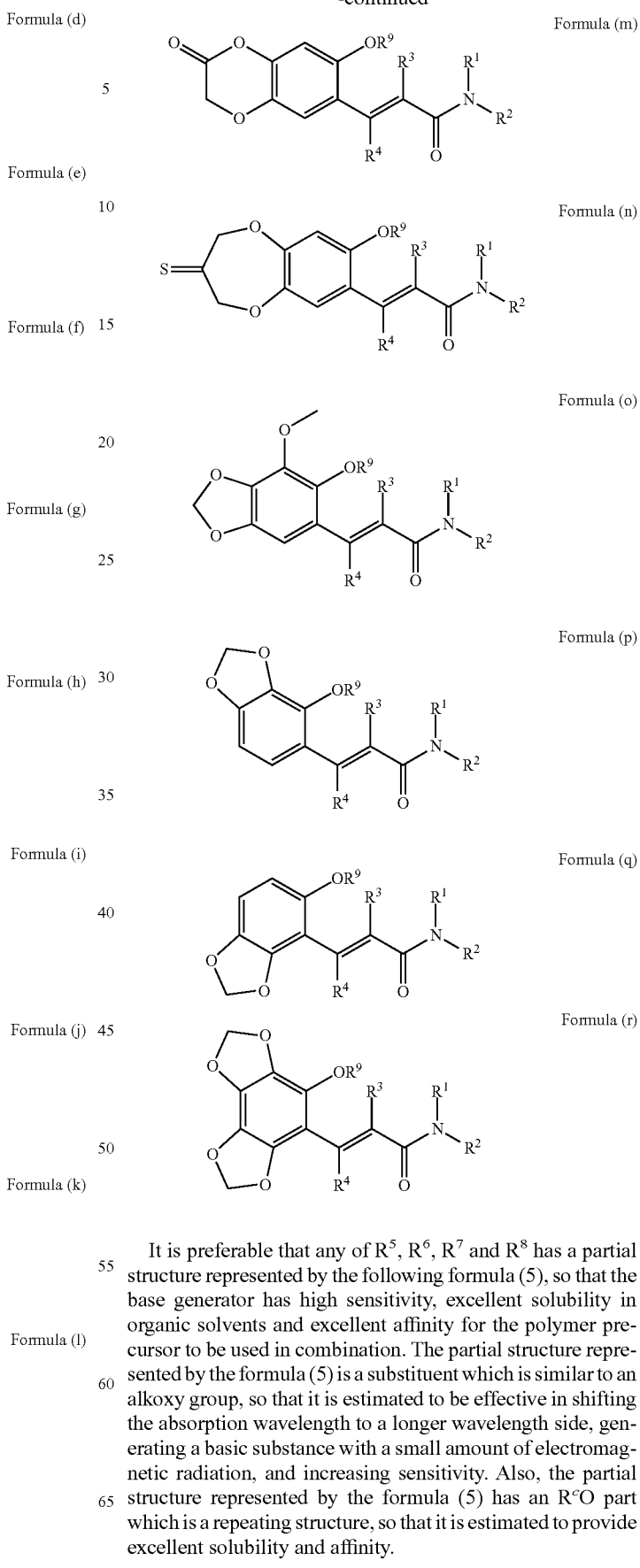

It is preferable that any of $R^5$, $R^6$, $R^7$ and $R^8$ has a partial structure represented by the following formula (5), so that the base generator has high sensitivity, excellent solubility in organic solvents and excellent affinity for the polymer precursor to be used in combination. The partial structure represented by the formula (5) is a substituent which is similar to an alkoxy group, so that it is estimated to be effective in shifting the absorption wavelength to a longer wavelength side, generating a basic substance with a small amount of electromagnetic radiation, and increasing sensitivity. Also, the partial structure represented by the formula (5) has an $R^cO$ part which is a repeating structure, so that it is estimated to provide excellent solubility and affinity.

[Chemical formula 8]

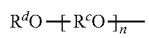    Formula (5)

In the formula (5), $R^c$ is a linking group that can be bound to two oxygen atoms; $R^d$ is a hydrogen, a silyl group, a silanol group, a phosphino group, a phosphinyl group, a phosphono group or an organic group; and n is an integer of 1 or more.

The partial structure represented by the formula (5) has only to be included in at least one of $R^5$, $R^6$, $R^7$ and $R^8$. A typical example thereof is a structure in which the partial structure represented by the formula (5) is directly bound to the benzene ring in the position of any of $R^5$, $R^6$, $R^7$ and $R^8$, as a substituent. Any of $R^5$, $R^6$, $R^7$ and $R^8$ can be an organic group, a part of which is the partial structure represented by the formula (5). When two or more of $R^5$ to $R^8$ are bound to form an alicyclic hydrocarbon structure such as a cyclohexyl group, or when two or more of $R^3$ to $R^8$ are bound to form a condensed ring such as naphthalene, anthracene, phenanthrene, indene or fluorene, sharing an atom of the benzene ring to which $R^5$ to $R^8$ are bound, the cyclic structure can have the partial structure represented by the formula (5) as a substituent.

$R^c$ in the partial structure represented by the formula (5) is not particularly limited as long as it is a linking group that can be bound to two oxygen atoms. Also, n $R^c$(s) included in the repeating unit may be the same or different.

In the present invention, from the viewpoint of obtaining high sensitivity, $R^c$ is preferably a linking group selected from the group consisting of: a linear, branched or cyclic, saturated or unsaturated, aliphatic or aromatic hydrocarbon group which has 1 to 20 carbon atoms and which can contain a heteroatom and/or have a substituent; a linear, branched or cyclic hydrogen silicide group which has 1 to 20 silicon atoms, which can contain a heteroatom and/or have a substituent, and which can contain a silicon-silicon double bond; a carbonyl bond; a thiocarbonyl bond; a sulfonyl bond; a sulfinyl bond; and an azo bond.

From the viewpoint of obtaining heat resistance, $R^c$ is preferably a linking group selected from the group consisting of: a linear, branched or cyclic, saturated or unsaturated, aliphatic or aromatic hydrocarbon group which has 1 to 20 carbon atoms and which can contain a heteroatom and/or have a substituent; a linear, branched or cyclic hydrogen silicide group which has 1 to 20 silicon atoms, which can contain a heteroatom and/or have a substituent, and which can contain a silicon-silicon double bond; a carbonyl bond; a thiocarbonyl bond; a sulfonyl bond; and a sulfinyl bond. They may be the same as those listed above in connection with X in the formula (3).

$R^c$ is more preferably a linear, branched or cyclic, saturated or unsaturated, aliphatic or aromatic hydrocarbon group which has 1 to 20 carbon atoms and which can contain a heteroatom and/or have a substituent, and still more preferably a linear, branched or cyclic, saturated or unsaturated, aliphatic hydrocarbon group which has 1 to 10 carbon atoms and which can have a substituent. $R^c$ is even still more preferably a linear, branched or cyclic, saturated aliphatic hydrocarbon group which has 1 to 6 carbon atoms and which can have a substituent, and particularly preferably it is a linear, branched or cyclic, saturated aliphatic hydrocarbon group which has 1 to 3 carbon atoms and which can have a substituent.

The repeating number of $OR^c$, n, is an integer of 1 or more. Preferably, n is adjusted appropriately depending on the structure or molecular weight of $R^c$; however, n is preferably 1 to 20 and more preferably 1 to 10.

$R^d$ is a hydrogen, a silyl group, a silanol group, a phosphino group, a phosphinyl group, a phosphono group or an organic group. As the organic group, there may be used those that are listed above in connection with $R^5$ to $R^8$.

From the viewpoint of sensitivity and solvent solubility, $R^d$ is preferably an organic group.

In the base generator of the present invention, $R^9$ is a protecting group which can be deprotected by heating and/or exposure to electromagnetic radiation. What is meant by "which can be deprotected" is that there is a possibility that $-OR^9$ is changed to $-OH$. $R^9$ is deprotected by heating and/or exposure to electromagnetic radiation, thereby producing a hydroxyl group. $R^9$ can be used without any particular limitation as long as it is a protecting group for a phenolic hydroxyl group that can be deprotected by heating and/or exposure to electromagnetic radiation in such a condition that an amide group present in the formula (1) is not decomposed in the base generator of the present invention. For example, an amide bond is decomposed by heating in a highly acidic environment where a strong Lewis acid (such as boron tribromide or aluminum trichloride) or a strong acid (such as sulfuric acid, hydrochloric acid or nitric acid) is present, or by heating in a highly basic environment where a strong base (such as sodium hydroxide) is present. Therefore, a protecting group which is deprotected only in such a highly acidic or basic condition is not appropriate as the protecting group that is used for the base generator of the present invention. $R^9$ is appropriately selected depending on the type of the compound which is used in combination with the base generator or on the application method or synthesis method of the base generator, with a view to increasing solubility or compatibility or to changing reactivity upon synthesis.

$R^9$ can be selected from a silyl group, a silanol group, a phosphino group, a phosphinyl group, a phosphono group or an organic group. When $R^9$ is an organic group, it is generally a monovalent organic group.

From the point of view that $R^9$ can be deprotected by heating and/or exposure to electromagnetic radiation in such a condition that the amide group present in the formula (1) cannot be decomposed, $R^9$ is preferably one or more kinds selected from the group consisting of organic groups represented by the following formulae (2-1) to (2-6):

[Chemical formula 9]

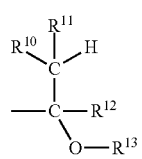    Formula (2-1)

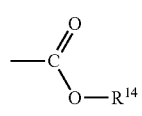    Formula (2-2)

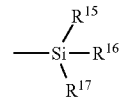    Formula (2-3)

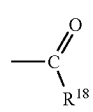

Formula (2-4)

Formula (2-5)

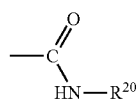

Formula (2-6)

wherein $R^{10}$, $R^{11}$ and $R^{12}$ in the formula (2-1) are each independently a hydrogen, a halogen or an organic group; $R^{13}$ in the formula (2-1) is an organic group; $R^{10}$, $R^{11}$, $R^{12}$ and $R^{13}$ may be bound to form a cyclic structure; $R^{14}$ in the formula (2-2) is an organic group; $R^{15}$, $R^{16}$ and $R^{17}$ in the formula (2-3) are each independently a hydrogen, a halogen or an organic group; $R^{18}$ in the formula (2-4) is an organic group; $R^{19}$ in the formula (2-5) is an aromatic ring which may have a substituent; and $R^{20}$ in the formula (2-6) is an organic group.

When $R^{10}$ to $R^{20}$ are organic groups, they are generally monovalent organic groups. However, they can be divalent or more organic croups.

The organic group represented by the formula (2-1) can be obtained by, as described below, the reaction of a phenolic hydroxyl group with a vinyl ether compound, for example:

[Chemical formula 10]

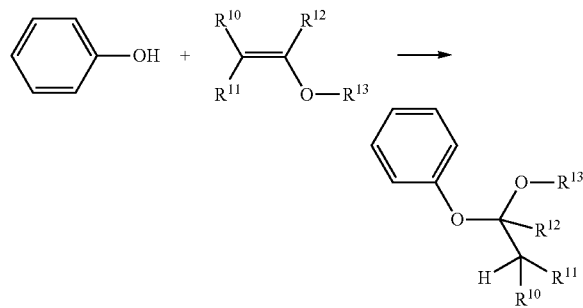

wherein $R^{10}$, $R^{11}$, $R^{12}$ and $R^{13}$ are the same as the formula (2-1).

When the organic group represented by the formula (2-1) is obtained by this reaction, $R^{10}$, $R^{11}$, $R^{12}$ and $R^{13}$ are determined by the structure of the vinyl ether compound used. The organic group represented by the formula (2-1) is not particularly limited and can be appropriately selected depending on the type of the compound (e.g., a polymer precursor) which is used in combination with the base generator or on the application method of the base generator.

$R^{10}$, $R^{11}$ and $R^{12}$ are each preferably a hydrogen or a substituted or unsubstituted, alkyl, ally or aryl group. From the viewpoint of availability of raw materials, a hydrogen is preferred. From the viewpoint of stability of the compound, it is also preferable that $R^{10}$, $R^{11}$ and $R^{12}$ do not contain a primary, secondary or tertiary amino group or a substituent having an active hydrogen such as a hydroxyl group.

$R^{13}$ of the organic group represented by the formula (2-1) is an organic group having 1 or more carbon atoms. An example of $R^{13}$ is a group having a hydrocarbon skeleton. The group having a hydrocarbon skeleton can contain a substituent or a bond other than a hydrocarbon, such as a heteroatom, and such a heteroatom part can be incorporated into an aromatic ring to form a hetero ring. Examples of the group having a hydrocarbon skeleton include: a linear, branched or cyclic, saturated or unsaturated hydrocarbon group; a linear, branched or cyclic, saturated or unsaturated alkyl halide group; an aromatic group (e.g., phenyl, naphthyl); a linear or branched, saturated or unsaturated group having a hydrocarbon skeleton that contains an ether bond (for example, there may be mentioned —(R—O)$_n$—R' wherein R and R' are each a substituted or unsubstituted, saturated or unsaturated hydrocarbon and n is an integer of 1 or more, and —R"—(O—R''')$_m$ wherein R" and R''' are each a substituted or unsubstituted, saturated or unsaturated hydrocarbon; m is an integer of 1 or more; and —(O—R''')$_m$ is bound to a carbon which is different from that at the terminal of R"), a linear or branched, saturated or unsaturated group having a hydrocarbon skeleton that contains a thioether bond; linear or branched, saturated or unsaturated groups having a hydrocarbon skeleton to which a heteroatom or a heteroatom-containing group (e.g., cyano group, silyl group, nitro group, acetyl group, acetoxy group) is bound. $R^{13}$ of the organic group represented by the formula (2-1) can be bound to $R^{10}$ or $R^{11}$ to form a cyclic structure. From the viewpoint of stability of The compound, it is preferable that $R^{13}$ does not contain a primary, secondary or tertiary amino group or a substituent having an active hydrogen such as a hydroxyl group, also.

The organic group represented by the formula (2-1) is deprotected by heating and/or exposure to electromagnetic radiation. In general, substituents have a tendency that the deprotection temperature increases in the following order of carbon atoms which are each directly bound to an oxygen atom (ether bond) of the vinyl ether compound at $R^{13}$ of the above formula: tertiary carbon atom (hereinafter may be referred to as "tertiary carbon")<secondary carbon atom (hereinafter may be referred to as "secondary carbon")<primary carbon atom (hereinafter may be referred to as "primary carbon").

Meanwhile, in general, substituents have a tendency that the reaction rate of the protection reaction of the vinyl ether compound with the hydroxyl group increases in the following order of carbon atoms which are each bound to an oxygen atom at $R^{13}$ of the above formula: primary carbon<secondary carbon<tertiary carbon.

Therefore, it is preferable that the heating temperature for deprotection is selected depending on the compound to be used in combination with the base generator and the usage, and the protecting group is appropriately selected depending on the thus-obtained heating temperature.

In the present invention, concerning the carbon atom which is bound to the ether oxygen (carbon atom bound to the oxygen atom at $R^{13}$ in the formula (2-1)) or the other carbon atom which is bound to the ether oxygen that is bound to a vinyl group of the vinyl ether compound which derives the organic group represented by the formula (2-1), "primary carbon atom" refers to the case where the carbon atom is bound to zero or one different carbon atom; "secondary carbon atom" refers to the case where the carbon atom is bound to two different carbon atoms; and "tertiary carbon atom" refers to the case where the carbon atom is bound to three different carbon atoms.

From the viewpoint of volatility of decomposed products, $R^{13}$ in the formula (2-1) preferably has 1 to 18 carbon atoms, more preferably 3 to 10 carbon atoms.

$R^{13}$ in the formula (2-1) is not particularly limited and examples thereof include a methyl group, an ethyl group, an ethynyl group, a propyl group, an isopropyl group, a n-butyl group, a t-butyl group, an n-hexyl group, a cyclohexyl group, a cyclohexylmethyl group, a methoxyethyl group, an ethoxyethyl group, a propoxyethyl group, a butoxyethyl group, a cyclohexyloxyethyl group, a methoxypropyl group, an ethoxypropyl group, a propoxypropyl group, a butoxypropyl group, a cyclohexyloxypropyl group and a 2-tetrahydropyranyl group. Also, there may be mentioned such an example that in the formula (2-1), $R^{13}$ is bound to $R^{10}$ or $R^{11}$ to form a cyclic structure and a substituent corresponding to $R^9$ is a cyclic ether such as a 2-tetrahydropyranyl group.

The organic group represented by the formula (2-2) can be obtained by, for example, the reaction of a phenolic hydroxyl group with a so-called carbonate-based protecting group.

Examples of the carbonate-based protecting group include a tert-butoxycarbonyl group (Boc-), a benzyloxycarbonyl group (Z-), a 9-fluorenylmethoxycarbonyl group (Fmoc-), a 1,1-dioxobenzo[b]thiophene-2-ylmethoxycarbonyl group (Bsmoc-), a 2-(4-nitrophenylsulphonyl)ethoxycarbonyl group (Nsc-), a p-methoxybenzyloxycarbonyl group (Z(OMe-)), an allyloxycarbonyl group (Alloc-) and a 2,2,2-trichloroethoxycarbonyl group (Troc-).

$R^{14}$ in the formula (2-2) is not particularly limited and examples thereof include a tert-butyl group, a benzyl group, a 9-fluorenylmethyl group, a 2,2,2-trichloroethyl group, an allyl group, a p-methoxybenzyl group, a 1,1-dioxobenzo[b]thiophene-2-ylmethyl group, a 2-(4-nitrophenylsulphonyl)ethyl group and an o-nitrobenzyl group. When $R^{14}$ is an o-nitrobenzyl group, it can be deprotected by exposure to electromagnetic radiation.

The organic group represented by the formula (2-3) can be obtained by, for example, the reaction of a phenolic hydroxyl group with a silyl ether-based protecting group.

Examples of the silyl ether-based protecting group include a trimethylsilyl group (TMS-), a tert-butyldimethylsilyl group (TBDMS-), a tert-butyldiphenylsilyl group (TBDPS-) and a triisopropylsilyl group (TIPS-).

$R^{15}$, $R^{16}$ and $R^{17}$ in the formula (2-3) are not particularly limited. For example, alkyl groups such as a methyl group, a tert-butyl group and an isopropyl group, and aryl groups such as a phenyl group are suitably used as $R^{15}$, $R^{16}$ and $R^{17}$.

The organic group represented by the formula (2-4) can be obtained by, for example, the reaction of a phenolic hydroxyl group with an acid chloride or acid anhydride.

Examples of an ester-based protecting group represented by the formula (2-4) include an acetyl group (Ac-), a pivaloyl group and a benzoyl group.

$R^{18}$ in the formula (2-4) is not particularly limited. For example, alkyl groups such as a methyl group and a tert-butyl group, aryl groups such as a phenyl group, and aralkyl groups such as a benzyl group are suitably used as $R^{18}$.

The organic group represented by the formula (2-5) can be obtained by, for example, the Williamson reaction of a phenolic hydroxyl group with a halide.

Examples of an ether-based protecting group represented by the formula (2-5) include a benzyl group which may have a substituent.

$R^{19}$ in the formula (2-5) is an aromatic ring which may have a substituent and is not particularly limited; however, examples thereof include phenyl and naphthyl groups which may have a substituent. Particularly in the case where the organic group represented by the formula (2-5) is an o-nitrobenzyl group, that is, $R^{19}$ is a 2-nitrophenyl group, the protecting group can be deprotected by exposure to electromagnetic radiation.

The organic group represented by the formula (2-6) can be obtained by, for example, the reaction of a phenolic hydroxyl group with an isocyanate.

Examples of a carbamate-based protecting group include a benzyl isocyanate.

R in the formula (2-6) is not particularly limited and examples thereof include a benzyl group.

The structure represented by the chemical formula (1) has a geometric isomer; however, it is preferable to use only a trans isomer as the structure represented by the chemical formula (1). However, there is a possibility that a cis isomer (geometric isomer) is mixed therewith during synthesis and purification processes, storage, etc., and in this case, a mixture of the trans and cis isomers can be used. From the point of view that it is possible to increase the dissolution contrast, the percentage of the cis isomer is preferably less than 10%.

The base generator represented by the chemical formula (1) preferably has a 5% weight loss temperature (a temperature at which there is a weight decrease of 5% from the initial weight by heating) of 60° C. or more, more preferably 100° C. or more. In the case of using a polyimide or polybenzoxazole precursor, it is needed to use a high-boiling solvent such as N-methyl-2-pyrrolidone to form a coating film. However, in the case where the base generator has such a high 5% weight loss temperature, it is possible to form a coating film in a drying condition which can minimize the influence of a residual solvent. Therefore, it is possible to prevent a decrease in the dissolution contrast between the exposed and unexposed regions, which is due to the influence of the residual solvent.

In the present invention, "x % weight loss temperature" is a temperature at which, when measured for weight decrease with a thermogravimetric analyzer, a sample shows a weight decrease of x % from the initial weight (that is, a temperature at which the weight of the sample is (100−x) % of the initial weight).

It is also preferable that no impurities derived from the base generator of the present invention remain in a product produced by using the photosensitive resin composition of the present invention. Therefore, it is preferable that the base generator of the present invention is decomposed or volatilized in a heating process after development (for example, in the case where the polymer combined is a polyimide precursor, in an imidization process). In particular, the base generator preferably has a 50% weight loss temperature (a temperature at which there is a weight decrease of 50% from the initial weight) of 400° C. or less, more preferably 350° C. or less. The base thus generated preferably has a boiling point of 25° C. or more for ease of handling at room temperature. If the boiling point of the base is not 25° C. or more, an amine thus generated is likely to evaporate from the coating film formed from the photosensitive resin composition especially at the time of drying the film, which can result in difficulty in handling.

The base thus generated preferably has a boiling point of 25° C. or more for ease of handling at room temperature. If the boiling point of the base is not 25° C. or more, amine thus generated is likely to evaporate from the coating film formed from the photosensitive resin composition especially at the time of drying the film, which can result in difficulty in handling In the case of using the thus-generated base as a curing accelerator that will not remain in the film, it is preferable that the thus-generated base preferably shows a weight decrease of 80% or more at 350° C., so that it is easy to prevent the base from remaining in the polymer after curing. However, in the case of using the thus-generated base as a crosslinking or curing agent which will remain in the film, the above-described weight decrease of the thus-generated base is not a problem.

In the case of using the base generator represented by the formula (1), the heating temperature for deprotecting the protecting group and generating a base is appropriately determined depending on the polymer precursor to be combined or on the intended purpose, and it is not particularly limited. The heating can be heating at a temperature of the environment where the base generator is placed (e.g., room temperature) and in this case, bases are gradually generated. Bases are also generated by heat that is produced as a by-product of the exposure to electromagnetic radiation, so that heating can be substantially performed at the same time by the heat produced as the by-product. To increase the reaction rate and efficiently generate a base, the heating temperature for generating a base is preferably 30° C. or more, more preferably 60° C. or more, still more preferably 100° C. or more, and particularly preferably 120° C. or more. However, the suitable heating temperature is not limited thereto because the unexposed region can be cured by heating at 60° C. or more for example, depending on the type of the polymer precursor used in combination. To prevent the base generator represented by the formula (1) from decomposition other than base generation, the base generator is preferably heated at 300° C. or less, more preferably at 200° C. or less.

When heating the base generator, it is possible to deprotect the protecting group at a low temperature and to generate a base at a higher temperature.

Deprotection of the protecting group can be performed only by heating or only by exposure to electromagnetic radiation. In the case of deprotecting the protecting group only by exposure to electromagnetic radiation, deprotection can be performed by the exposure to electromagnetic radiation for base generation, or the wavelength can be changed by the exposure to electromagnetic radiation for deprotection and that for base generation. An example is such that deprotection is performed by exposure to long-wavelength electromagnetic radiation and then isomerization is performed by exposure to short-wavelength electromagnetic radiation for base generation. In these cases, the amount of electromagnetic radiation varies depending on the electromagnetic radiation used, and the amount is not particularly limited and is appropriately controlled.

Deprotection can be performed by performing heating and exposure to electromagnetic radiation simultaneously or alternately.

Also, deprotection can be performed by heating before the exposure. Depending on the type of protecting group, the absorption wavelength is shifted to a short wavelength side by introducing the protecting group and there could be a decrease in the sensitivity of the base generator, therefore. In this case, the sensitivity of the same upon exposure to electromagnetic radiation can be increased by deprotecting the protecting group in advance by heating before exposure to electromagnetic radiation, and then exposing the base generator to electromagnetic radiation.

The deprotection condition of the protecting group varies depending on the components coexisting in the composition. For example, when other photoacid generator and/or photobase generator is contained in the composition, the heating temperature after the exposure could be changed by the influence of the acid/base generated by exposure to electromagnetic radiation.

The base generator represented by the formula (1) generates a base only by exposure to electromagnetic radiation; however, base generation is accelerated by heating the base generator appropriately. Therefore, in the case of using the base generator represented by the formula (1), heating is performed after or at the same time as exposure to electromagnetic radiation (exposure). Exposure and heating can be performed alternately. The most efficient method is heating at the same time as the exposure.

A method for synthesizing the base generator represented by the chemical formula (1) of the present invention will be explained by reference to the case of protecting the hydroxyl group of 2-hydroxycinnamic acid amide. The present invention is not limited thereto, however. The base generator of the present invention can be synthesized by conventionally known synthesis routes.

For example, 2-hydroxycinnamic acid amide can be synthesized by the reaction of 2-hydroxycinnamic acid with cyclohexylamine. The target can be obtained by, in the presence of a condensing agent such as 1-ethyl-3-(3-dimethylaminopropyl)carbodiimide hydrochloride, dissolving 2-hydroxycinnamic acid and cyclohexylamine in tetrahydrofuran and stirring them.

A cinnamic acid to which a substituent is introduced can be synthesized by performing a Wittig, Knoevenagel or Perkin reaction on the hydroxybenzaldehyde having the corresponding substituent. Among them, Wittig reaction is preferred because it is easy to selectively obtain a trans isomer by the reaction. A hydroxybenzaldehyde to which a substituent is introduced can be synthesized by performing a Duff or Vilsmeier-Haack reaction on the phenol having the corresponding substituent or by performing a general ether synthesis method such as Williamson reaction on dihydroxybenzaldehyde.

The protecting group ($R^9$) can be introduced to the phenolic hydroxyl group in the middle or at the end of the synthesis. For example, in the case of protecting the hydroxyl group using a vinyl ether compound, the target can be synthesized by the reaction of 2-hydroxycinnamic acid amide with vinyl ether. The target can be obtained by, in the presence of an acid catalyst such as pyridinium p-toluenesulfonate, dissolving 2-hydroxycinnamic acid amide and a vinyl ether compound in dimethylformamide and stirring them.

In the case of protecting the hydroxyl group using a carbonate-based protecting group, the target can be synthesized with 2-hydroxycinnamic acid amide and a reagent for introducing a carbonate-based protecting group (such as di-t-butyl dicarbonate, benzyloxycarbonyl chloride or N-(9-fluorenylmethoxycarbonyloxy)succinimide).

In the case of protecting the hydroxyl group using a silyl ether-based protecting group, the target can be synthesized by, in the presence of a base catalyst such as imidazole, dissolving 2-hydroxycinnamic acid amide and a reagent for introducing a silyl ether-based protecting group (such as chlorotrimethylsilane, tert-butyldimethylchlorosilane or tert-butyldiphenylchlorosilane) in dimethylformamide.

In the case of protecting the hydroxyl group using an ester-based protecting group, the target can be synthesized with 2-hydroxycinnamic acid amide and acid chloride or acid anhydride in the presence of a base catalyst such as triethylamine.

In the case of protecting the hydroxyl group using an ether-based protecting group, the target can be synthesized with 2-hydroxycinnamic acid amide and halide (such as benzyl chloride) in the presence of strong base such as sodium hydride.

In the case of protecting the hydroxyl group using a carbamate-based protecting group, the target can be synthesized from 2-hydroxycinnamic acid amide and isocyanate (such as benzyl isocyanate).

The base generator represented by the chemical formula (1) of the present invention is needed to have absorption at least a part of exposure wavelengths so that the base generator can sufficiently fulfill its base generation function for reacting the polymer precursor into a final product. The wavelengths of a high pressure mercury lamp, which are a general exposing source, are 365 nm, 405 nm and 436 nm. Therefore, the base generator represented by the chemical formula (1) of the present invention preferably has absorption at least one of electromagnetic radiation wavelengths of 365 nm, 405 nm and 436 nm. This is preferable because the types of applicable polymer precursors are further increased in this case.

The base generator represented by the chemical formula (1) preferably has a molar absorption coefficient of 100 or more at an electromagnetic radiation wavelength of 365 nm, or a molar absorption coefficient of 1 or more at 405 nm, so that the types of applicable polymer precursors are further increased.

The fact that the base generator represented by the chemical formula (1) of the present invention has absorption in the above-described wavelength range, can be proved by dissolving the base generator represented by the chemical formula (1) in a solvent having no absorption in the above wavelength range (e.g., acetonitrile) so as to reach a concentration of $1 \times 10^{-4}$ mol/L or less (it is normally about $1 \times 10^{-4}$ mol/L to $1 \times 10^{-5}$ mol/L and can be appropriately adjusted to reach an appropriate absorption wavelength) and then measuring the absorbance with an ultraviolet-visible spectrophotometer (such as UV-2550 manufactured by Shimadzu Corporation).

The base generator represented by the chemical formula (1) of the present invention has higher sensitivity than conventionally used photobase generators and is thus available for a wide range of applications. Various kinds of photosensitive compositions can be produced by not only combining the base generator with a polymer precursor in which reaction into a final product is promoted by a basic substance or by heating in the presence of a basic substance, which will be described below in detail, but also by combining the same with a compound which has a structure or properties that can be changed by a base such as an acid-base indicator. Such photosensitive compositions can be used as a paint, printing ink, sealing agent or adhesive, or as a material for forming display, semiconductor device, electronic component, microelectromechanical system (MEMS), optical member or building material.

For example, the base generator can be applied to a display such as an image forming medium which comprises an image forming layer that contains at least a photobase generator and an acid-base indicator and that covers or penetrates a substrate, and which forms an image in such a manner that when the image forming layer is exposed to light, the photobase generator generates a base that is reactive with the acid-base indicator, thereby forming an image.

<Photosensitive Resin Composition>

The photosensitive resin composition of the present invention comprises a polymer precursor in which reaction into a final product is promoted by a basic substance or by heating in the presence of a basic substance, and the base generator of the present invention which is represented by the following chemical formula (1) and generates a base by exposure to electromagnetic radiation and heating:

[Chemical formula 11]

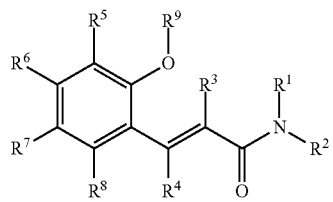

Formula (1)

wherein $R^1$ and $R^2$ are each independently a hydrogen or an organic group and may be the same or different; $R^1$ and $R^2$ may be bound to form a cyclic structure which may contain a heteroatom; at least one of $R^1$ and $R^2$ is an organic group; $R^3$ and $R^4$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group or an organic group and may be the same or different; $R^5 R^6$, $R^7$ and $R^8$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group or an organic group and may be the same or different; two or more of $R^5$, $R^6$, $R^7$ and $R^8$ may be bound to form a cyclic structure which may contain a heteroatom; and $R^9$ is a protecting group which can be deprotected by heating and/or exposure to electromagnetic radiation.

As described above, the base generator represented by the formula (1) has the above-specified structure. Therefore, by exposing the base generator to electromagnetic radiation, ($-CR^4=CR^3-C(=O)-$) is isomerized into a cis isomer. By further heating the same, the protecting group $R^9$ is deprotected and cyclized, thereby generating a base ($NHR^1R^2$).

In the polymer precursor, reaction into a final product is promoted by the action of the basic substance generated from the base generator.

Due to such a change in solubility of the polymer precursor, in the photosensitive resin composition of the present invention, a difference in solubility occurs between the exposed and unexposed regions, that is, the dissolution contrast is increased, so that pattern formation is possible.

As described above, the base generator represented by the formula (1) has higher sensitivity than conventional photobase generators, so that the photosensitive resin composition of the present invention is highly sensitive. Also, a wide range of polymer precursors can be applied to the photosensitive resin composition of the present invention, so that the photosensitive resin composition can be widely used in areas where the characteristics of the composition can be utilized, such as the change in solubility of the polymer precursor and base generator. For example, the photosensitive resin composition of the present invention can be suitably used in areas where the characteristics of a photosensitive polyimide precursor resin composition and an imidized product thereof can be utilized.

Hereinafter, the components of the photosensitive resin composition of the present invention will be described. A base generator which can be used for the photosensitive resin composition of the present invention will not be described since, as the base generator, one which is similar to the base generator of the present invention can be used. Accordingly, the polymer precursor and other components that can be contained in the composition as needed, will be described in order.

As the base generator and polymer precursor, only one kind can be used, or a mixture of two or more kinds can be used.

<Polymer Precursor>

The polymer precursor used for the photosensitive resin composition of the present invention refers to a substance which is finally reacted into a polymer with target properties by a reaction. Examples of the reaction include an intermolecular reaction and an intramolecular reaction. The polymer precursor itself can be a relatively low molecular weight compound or a high molecular weight compound.

The polymer precursor of the present invention is a compound in which reaction into a final product is promoted by a basic substance or by heating in the presence of a basic substance. Examples of the embodiment in which reaction into a final product is promoted in the polymer precursor by a basic substance or by heating in the presence of a basic substance include not only an embodiment in which the polymer precursor is reacted into a final product only by the action of a basis substance, but also an embodiment in which the reaction temperature of the polymer precursor at which the polymer precursor is reacted into a final product by the action of a basic substance is lowered compared to the case without the action of a basic substance.

In the case where there is such a reaction temperature difference due to the presence or absence of a basic substance, by utilizing the reaction temperature difference and heating at an appropriate temperature at which only the polymer precursor coexisting with the basic substance is reacted into a final product, only the polymer precursor coexisting with the basic substance is reacted into a final product, and the solubility of the polymer precursor in a solvent such as a developer is changed. Therefore, the solubility of the polymer precursor in the solvent can be changed by the presence or absence of the basic substance, so that patterning by development using the solvent as a developer is possible.

As the polymer precursor of the present invention, any polymer precursor can be used without particular limitation as long as it can be reacted into a final product by the basis substance as described above or by heating in the presence of such a basic substance. Typical examples of such a polymer precursor will be described below; however, the polymer precursor of the present invention is not limited thereto.

[Polymer Precursor which is Reacted into Polymer by Intermolecular Reaction]

Examples of the polymer precursor which is reacted into a target polymer by an intermolecular reaction include a compound and polymer which have a reactive substituent and cause a polymerization reaction, or a compound and polymer which cause a reaction to form a bond between molecules (crosslinking reaction). Examples of the reactive substituent include an epoxy group, an oxetane group, a thiirane group, an isocyanate group, a hydroxyl group and a silanol group. Examples of the polymer precursor include a compound which causes hydrolysis and polycondensation between molecules, and examples of the reactive substituent include —SiX of polysiloxane precursor, wherein X is a hydrolyzable group selected from the group consisting of an alkoxy group, an acetoxy group, an oxime group, an enoxy group, an amino group, an aminooxy group, an amide group and a halogen.

Examples of the compound which has a reactive substituent and causes a polymerization reaction include a compound having one or more epoxy groups, a compound having one or more oxetane groups, and a compound having one or more thiirane groups.

Examples of the polymer which has a reactive substituent and causes a polymerization reaction include a polymer having two or more epoxy groups (epoxy resin), a polymer having two or more oxetane groups, and a polymer having two or more thiirane groups. Among them, the compound and polymer having the epoxy group(s) will be described below in detail. However, the compounds and polymers having the oxetane group(s) and those having the thiirane group(s) can be used similarly to them.

(Compound and Polymer Having Epoxy Group)

As the compound and polymer having one or more epoxy groups, any conventionally known compound and polymer can be used without particular limitation as long as the compound and polymer have one or more epoxy groups in a molecule thereof.

In general, the base generator also functions as a curing catalyst for a compound having one or more epoxy groups in a molecule thereof.

In the case of using the compound having one or more epoxy groups in a molecule thereof or the polymer having two or more epoxy groups in a molecule thereof (epoxy resin), a compound having two or more functional groups in a molecule thereof can be used in combination therewith, which are reactive with epoxy groups. Examples of the functional groups which are reactive with epoxy groups include carboxyl groups, phenolic hydroxyl groups, mercapto groups and primary or secondary aromatic amino groups. Considering three dimensional curing properties, the number of the functional groups in a molecule of the compound is preferably two or more.

Also, it is preferable to use a polymer which has a weight average molecular weight of 3,000 to 100,000 and in which the functional groups are introduced to a side chain thereof. If the weight average molecular weight is less than 3,000, the strength of a cured film could be decreased; moreover, the surface of the cured film could be tacky and impurities are likely to adhere thereto. It is not preferable that the weight average molecular weight is more than 100,000 because there is a possible increase in viscosity.

An example of the polymer having one or more epoxy groups in a molecule thereof is epoxy resin. Examples of the epoxy resin include a bisphenol A type epoxy resin derived from bisphenol A and epichlorohydrin, bisphenol F type epoxy resin derived from bisphenol F and epichlorohydrin, a bisphenol S type epoxy resin, a phenol novolac type epoxy resin, a cresol novolac type epoxy resin, a bisphenol A novolac type epoxy resin, a bisphenol F novolac type epoxy resin, an alicyclic epoxy resin, a diphenyl ether type epoxy resin, a hydroquinone type epoxy resin, a naphthalene type epoxy resin, a biphenyl type epoxy resin, a fluorene type epoxy resin, polyfunctional type epoxy resins such as a trifunctional type epoxy resin an a tetrafunctional type epoxy resin, a glycidyl ester type epoxy resin, a glycidyl amine type epoxy resin, a hydantoin type epoxy resin, an isocyanurate type epoxy resin and a chain aliphatic epoxy resin. These epoxy resins can be halogenated or hydrogenated. Commercially available epoxy resin products include, but not limited to, jER coat 828, 1001, 801N, 806, 807, 152, 604, 630, 871, YX8000, YX8034 and YX4000 (manufactured by Japan Epoxy Resins Co., Ltd.), EPICLON 830, EXA835LV, HP4032D and HP820 (manufactured by DIC Corporation), EP4100 series, EP4000 series and EPU series (manufactured by ADEKA Corporation), CELLOXIDE series (2021, 2021P, 2083, 2085, 3000, etc.), EPOLEAD series and EHPE series (manufactured by DAICEL Chemical Industries, Ltd.), YD series, YDF series, YDCN series and YDB series (manufactured by Tohto Kasei Co., Ltd.), DENACOL series (manufactured by Nagase ChemteX Corporation), and EPOLIGHT series (manufactured by Kyoeisha Chemical Co., Ltd.), for example. These epoxy resins can be used in combination of two or more kinds. Among them, preferred are bisphenol type epoxy resins because, compared to other various kinds of epoxy compounds, bisphenol type epoxy resin products having different molecular weights are widely available and make it possible to optionally set adhesion, reactivity, etc.

An example of the compound which causes a crosslinking reaction between molecules is a combination of a compound having two or more isocyanate groups in a molecule thereof and a compound having two or more hydroxyl groups in a molecule thereof. An urethane bond is formed between molecules by the reaction of the isocyanate groups with the hydroxyl groups, so that the combination can be reacted into a polymer.

An example of the polymer which causes a crosslinking reaction between molecules is a combination of a polymer having two or more isocyanate groups in a molecule thereof (isocyanate resin) and a polymer having two or more hydroxyl groups in a molecule thereof (polyol).

It is also possible to use a combination of a compound and polymer, each of which causes a crosslinking reaction between molecules. Examples of such a combination include a combination of a polymer having two or more isocyanate groups in a molecule (isocyanate resin) and a compound having two or more hydroxyl groups in a molecule, and a combination of a compound having two or more isocyanate groups in a molecule and a polymer having two or more hydroxyl groups in a molecule (polyol).

(Compound and Polymer Having Isocyanate Groups)

As the compound and polymer having isocyanate groups, a conventionally known compound and polymer can be used without particularly limited as long as they have two or more isocyanate groups in a molecule thereof. Examples of such a compound include low-molecular-weight compounds such as p-phenylene diisocyanate, 2,4-toluene diisocyanate, 2,6-toluene diisocyanate, 1,5-naphthalene diisocyanate and hexamethylene diisocyanate, an oligomer and a polymer which has a weight average molecular weight of 3,000 or more and in which isocyanate groups are present at a side chain or terminal thereof.

(Compound and Polymer having Hydroxyl Groups)

In general, the compound and polymer having isocyanate groups are each used in combination with a compound having hydroxyl groups in a molecule thereof. As such a compound having hydroxyl groups, any conventionally known compound can be used without particular limitation as long as it has two or more hydroxyl groups in a molecule thereof. Examples of such a compound include low-molecular-weight compounds such as ethylene glycol, propylene glycol, glycerin, diglycerin and pentaerythritol, and a polymer which has a weight average molecular weight of 3,000 or more and in which hydroxyl groups are present at a side chain or terminal thereof.

(Polysiloxane Precursor)

An example of the compound which causes hydrolysis and polycondensation between molecules is a polysiloxane precursor.

Examples of the polysiloxane precursor include an organic silicon compound represented by $Y_nSiX_{(4-n)}$ (wherein Y is a hydrogen or an alkyl group, fluoroalkyl group, vinyl group or phenyl group which may have a substituent; X is a hydrolyzable group selected from the group consisting of an alkoxy group, an acetoxy group, an oxime group, an enoxy group, an amino group, an aminooxy group, an amide group and a halogen; and n is an integer of 0 to 3) and a hydrolyzed polycondensate of the organic silicon compound. Among them, preferred is one represented by the above formula wherein n is an integer of 0 to 2. As the hydrolyzable group, preferred is an alkoxy group in terms of the ease of preparing a silica-dispersed oligomer solution and its availability.

The organic silicon compound is not particularly limited and conventionally known organic silicon compounds can be used as the compound. Examples thereof include trimethoxysilane, triethoxysilane, methyltrichlorosilane, methyltrimethoxysilane, methyltriethoxysilane, methyltriisopropoxysilane, methyltri-t-butoxysilane, ethyltribromosilane, ethyltrimethoxysilane, ethyltriethoxysilane, n-propyltriethoxysilane, n-hexyltrimethoxysilane, phenyltrimethoxysilane, phenyltriethoxysilane, tetramethoxysilane, tetraethoxysilane, tetrabutoxysilane, dimethoxydiethoxysilane, dimethyldichlorosilane, dimethyldimethoxysilane, diphenyldimethoxysilane, vinyltrimethoxysilane, trifluoropropyltrimethoxysilane, γ-glycidoxypropylmethyldiethoxysilane, γ-glycidoxypropyltrimethoxysilane, γ-methacryloxypropylmethyldimethoxysilane, γ-aminopropylmethyldimethoxysilane, γ-mercaptopropylmethyldiethoxysilane, γ-mercaptopropyltrimethoxysilane, β-(3,4-epoxycyclohexyl)ethyltrimethoxysilane, fluoroalkylsilane which is known as a fluorine-containing silane coupling agent, hydrolysis-condensation products or hydrolysis-cocondensation products thereof, and mixtures thereof.

[Polymer Precursor which is Reacted into Polymer by Intramolecular Ring Closure Reaction]

Examples of the polymer precursor which is finally reacted into a polymer with target properties by an intermolecular ring closure reaction include a polyimide precursor and a polybenzoxazole precursor. Each of these precursors can be a mixture of two or more polymer precursors synthesized separately.

The polyimide precursor and polybenzoxazole precursor which are polymer precursors preferred in the present invention will be described below. However, the present invention is not limited thereto.

(Polyimide Precursor)

As the polyimide precursor, a polyamic acid having a repeating unit represented by the following chemical formula (6) is suitably used:

[Chemical formula 12]

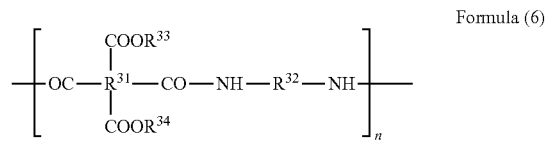

Formula (6)

wherein $R^{31}$ is a tetravalent organic group; $R^{32}$ is a divalent organic group; $R^{33}$ and $R^{34}$ are a hydrogen atom or organic group each; and n is a natural number of 1 or more.

When $R^{33}$ and $R^{34}$ are organic groups, examples thereof include an alkyl group, an alkenyl group, an alkynyl group, an aryl group and structures comprising these groups and an ether bond, as represented by the formula $C_nH_{2n}OC_mH_{2m+1}$.

As the polyimide precursor, a polyamic acid represented by the following formula (6') is suitably used from the viewpoint of alkali developing properties:

[Chemical formula 13]

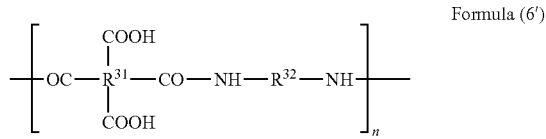

Formula (6')

wherein $R^{31}$ is a tetravalent organic groups; $R^{32}$ is a divalent organic groups; and n is a natural number of 1 or more.

In the formulae (6) and (6'), the tetravalence of $R^{31}$ means a tetracarboxylic acid residue derived from an acid dianhydride, etc., and the divalence of $R^{32}$ means a diamine residue. The tetravalence of $R^{31}$ only refers to a valence for bonding to acids; however, $R^{31}$ may have other substituent(s) further.

Similarly, the divalence of $R^{32}$ refers only to a valence for bonding to amines; however, $R^{32}$ may have other substituent(s) further.

Polyamic acid is preferred because it can be obtained only by mixing an acid dianhydride with a diamine in a solution, so that it can be synthesized by a one-step reaction, is easy to synthesize and can be obtained at low cost.

There is such a secondary effect that when the polymer precursor used is a polyamic acid, a low temperature is good enough for imidization to take place due to the catalytic effect of the basic substance, so that it is possible to decrease the final curing temperature to less than 300° C., preferably 250° C. or less. Conventional polyamic acids have limited applications since the final curing temperature is needed to be 300° C. or more for imidization to take place; however, it is now possible by the present invention to decrease the final curing temperature and thus to use the polyamic acid in a wide range of applications.

A polyamic acid can be obtained by the reaction of an acid dianhydride and a diamine. However, to provide excellent heat resistance and dimensional stability to the finally-obtained polyimide, it is preferable that $R^{31}$ or $R^{32}$ of the chemical formula (6') is an aromatic compound, and it is more preferable that $R^{31}$ and $R^{32}$ of the chemical formula (6') are aromatic compounds. In this case, at $R^{31}$ of the chemical formula (6'), four groups ((—CO—)$_2$(—COOH)$_2$) bound to $R^{31}$ can be bound to the same aromatic ring or different aromatic rings. Similarly, at $R^{32}$ of the chemical formula (6'), two groups ((—NH—)$_2$) bound to $R^{32}$ can be bound to the same aromatic ring or different aromatic rings.

The polyamic acid represented by the chemical formula (6') can be one comprising a single repeating unit or one comprising two or more kinds of repeating units.

Conventionally known methods can be used as the method for producing the polyimide precursor of the present invention. Examples thereof include, but not limited to, (1) a method for synthesizing a polyamic acid (precursor) from an acid dianhydride and a diamine, and (2) a method for synthesizing a polyimide precursor by the reaction of a carboxylic acid of an ester acid or amide acid monomer with a diamino compound or derivative thereof, the ester acid or amino acid monomer being synthesized by the reaction of an acid dianhydride with a monovalent alcohol, an amino compound, an epoxy compound, or the like.

Examples of the acid dianhydride which are applicable to the reaction for obtaining the polyimide precursor of the present invention include aliphatic tetracarboxylic dianhydrides such as an ethylenetetracarboxylic dianhydride, butanetetracarboxylic dianhydride, cyclobutanetetracarboxylic dianhydride, methylcyclobutanetetracarboxylic dianhydride and cyclopentanetetracarboxylic dianhydride; and aromatic tetracarboxylic dianhydrides such as pyromellitic dianhydride, 3,3',4,4'-benzophenonetetracarboxylic dianhydride, 2,2',3,3'-benzophenonetetracarboxylic dianhydride, 2,3',3,4'-benzophenonetetracarboxylic dianhydride, 3,3',4,4'-biphenyltetracarboxylic dianhydride, 2,2',3,3'-biphenyltetracarboxylic dianhydride, 2,3',3,4'-biphenyltetracarboxylic dianhydride, 2,2',6,6'-biphenyltetracarboxylic dianhydride, 2,2-bis(3,4-dicarboxyphenyl)propane dianhydride, 2,2-bis(2,3-dicarboxyphenyl)propane dianhydride, bis (3,4-dicarboxyphenyl)ether dianhydride, bis(3,4-dicarboxyphenyl)sulfone dianhydride, 1,1-bis(2,3-dicarboxyphenyl) ethane dianhydride, bis(2,3-dicarboxyphenyl)methane dianhydride, bis(3,4-dicarboxyphenyl)methane dianhydride, 2,2-bis(3,4-dicarboxyphenyl)-1,1,1,3,3,3-hexafluoropropane dianhydride, 2,2-bis(2,3-dicarboxyphenyl)-1,1,1,3,3,3-hexafluoropropane dianhydride, 1,3-bis[(3,4-dicarboxy)benzoyl]benzene dianhydride, 1,4-bis[(3,4-dicarboxy)benzoyl] benzene dianhydride, 2,2-bis{4-[4-(1,2-dicarboxy)phenoxy] phenyl}propane dianhydride, 2,2-bis{4-[3-(1,2-dicarboxy)phenoxy]phenyl}propane dianhydride, bis{4-[4-(1,2-dicarboxy)phenoxy] phenyl}ketone dianhydride, bis{4-[3-(1,2-dicarboxy)phenoxy]phenyl}ketone dianhydride, 4,4'-bis[4-(1,2-dicarboxy) phenoxy]biphenyl dianhydride, 4,4'-bis[3-(1,2-dicarboxy) phenoxy]biphenyl dianhydride, bis{4-[4-(1,2-dicarboxy) phenoxy]phenyl}ketone dianhydride, bis{4-[3-(1,2-dicarboxy)phenoxy]phenyl}ketone dianhydride, bis{4-[4-(1,2-dicarboxy)phenoxy]phenyl}sulfone dianhydride, bis{4-[3-(1,2-dicarboxy)phenoxy]phenyl}sulfone dianhydride, bis{4-[4-(1,2-dicarboxy)phenoxy]phenyl}sulfide dianhydride, bis{4-[3-(1,2-dicarboxy)phenoxy]phenyl}sulfide dianhydride, 2,2-bis{4-[4-(1,2-dicarboxy)phenoxy]phenyl}-1,1,1,3,3,3-hexafluoropropane dianhydride, 2,2-bis{4-[3-(1,2-dicarboxy)phenoxy]phenyl}-1,1,1,3,3,3-hexafluoropropane dianhydride, 2,3,6,7-naphthalenetetracarboxylic dianhydride, 1,1,1,3,3,3-hexafluoro-2,2-bis(2,3- or 3,4-dicarboxyphenyl)propane dianhydride, 1,4,5,8-naphthalenetetracarboxylic dianhydride, 1,2,5,6-naphthalenetetracarboxylic dianhydride, 1,2,3,4-benzenetetracarboxylic dianhydride, 3,4,9,10-perylenetetracarboxylic dianhydride, 2,3,6,7-anthracenetetracarboxylic dianhydride, 1,2,7,8-phenanthrenetetracarboxylic dianhydride, pyridinetetracarboxylic dianhydride, sulfonyldiphthalic anhydride, m-terphenyl-3,3',4,4'-tetracarboxylic dianhydride and p-terphenyl-3,3',4,4'-tetracarboxylic dianhydride. They are used solely or in combination of two or more kinds. Preferred tetracarboxylic dianhydrides are pyromellitic dianhydride, 3,3',4,4'-benzophenonetetracarboxylic dianhydride, 3,3',4,4'-biphenyltetracarboxylic dianhydride, 2,2',6,6'-biphenyltetracarboxylic dianhydride, bis(3,4-dicarboxyphenyl)ether dianhydride and 2,2-bis(3,4-dicarboxyphenyl)-1,1,1,3,3,3-hexafluoropropane dianhydride.

In the case of using, as the acid anhydride used in combination, an acid dianhydride having a fluorine introduced thereto or an acid dianhydride having an alicyclic skeleton, it is possible to control physical properties (e.g., solubility and thermal expansion coefficient) without a large deterioration in transparency. In the case of using a rigid acid dianhydride such as pyromellitic dianhydride, 3,3',4,4'-biphenyltetracarboxylic dianhydride or 1,4,5,8-naphthalenetetracarboxylic dianhydride, the finally-obtained polyimide is provided with a small linear thermal expansion coefficient; however, there is a tendency that the use inhibits an increase in transparency, so that such a rigid acid dianhydride can be used in combination, paying attention to copolymerization ratio.

Meanwhile, as the amine component, one kind of diamine can be used solely or two or more kinds of diamines can be used in combination. The used diamine component(s) is not limited and examples thereof include aromatic diamines such as p-phenylenediamine, m-phenylenediamine, o-phenylenediamine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenyl sulfone, 3,4'-diaminodiphenyl sulfone, 4,4'-diaminodiphenyl sulfone, 3,3'-diaminobenzophenone, 4,4'-diaminobenzophenone, 3,4'-diaminobenzophenone, 3,3'-diaminodiphenylmethane, 4,4'-diaminodiphenylmethane, 3,4'-diaminodiphenylmethane, 2,2-di(3-aminophenyl)propane, 2,2-di(4-aminophenyl)propane, 2-(3-aminophenyl)-2-(4-aminophenyl)propane, 2,2-di(3-aminophenyl)-1,1,1,3,3,3-hexafluoropropane, 2,2-di(4-aminophenyl)-1,1,1,3,3,3-hexafluoropropane, 2-(3-aminophenyl)-2-(4-aminophenyl)-1,1,1,3,3,3- hexafluoropropane, 1,1-di(3-aminophenyl)-1-phenylethane, 1,1-di(4-aminophenyl)-1-phenylethane, 1-(3-aminophenyl)-1-(4-aminophenyl)-1-phenylethane, 1,3-bis(3-aminophenoxy)benzene, 1,3-bis(4-aminophenoxy)benzene, 1,4-bis(3-aminophenoxy)benzene, 1,4-bis(4-aminophenoxy)benzene, 1,3-bis(3-aminobenzoyl)benzene, 1,3-bis(4-aminobenzoyl)benzene, 1,4-bis(3-aminobenzoyl)benzene, 1,4-bis(4-aminobenzoyl)benzene, 1,3-bis(3-amino-α,α-dimethylbenzyl)benzene, 1,3-bis(4-amino-α,α-dimethylbenzyl)benzene, 1,4-bis(3-amino-α,α-dimethylbenzyl)benzene, 1,4-bis(4-amino-α,α-dimethylbenzyl)benzene, 1,3-bis(3-amino-α,α-ditrifluoromethylbenzyl)benzene, 1,3-bis(4-amino-α,α-ditrifluoromethylbenzyl)benzene, 1,4-bis(3-amino-α,α-ditrifluoromethylbenzyl)benzene, 1,4-bis(4-amino-α,α-ditrifluoromethylbenzyl)benzene, 2,6-bis(3-aminophenoxy)benzonitrile, 2,6-bis(3-aminophenoxy)pyridine, 4,4'-bis(3-aminophenoxy)biphenyl, 4,4'-bis(4-aminophenoxy)biphenyl, bis[4-(3-aminophenoxy)phenyl]ketone, bis[4-(4-aminophenoxy)phenyl]ketone, bis[4-(3-aminophenoxy)phenyl]sulfide, bis[4-(4-aminophenoxy)phenyl]sulfide, bis[4-(3-aminophenoxy)phenyl]sulfone, bis[4-(4-aminophenoxy)phenyl]sulfone, bis[4-(3-aminophenoxy)phenyl]ether, bis[4-(4-aminophenoxy)phenyl]ether, 2,2-bis[4-(3-aminophenoxy)phenyl]propane, 2,2-bis[4-(4-aminophenoxy)phenyl]propane, 2,2-bis[3-(3-aminophenoxy)phenyl]-1,1,1,3,3,3-hexafluoropropane, 2,2-bis[4-(4-aminophenoxy)phenyl]-1,1,1,3,3,3-hexafluoropropane, 1,3-bis[4-(3-aminophenoxy)benzoyl]benzene, 1,3-bis[4-(4-aminophenoxy)benzoyl]benzene, 1,4-bis[4-(3-aminophenoxy)benzoyl]benzene, 1,4-bis[4-(4-aminophenoxy)benzoyl]benzene, 1,3-bis[4-(3-aminophenoxy)-α,α-dimethylbenzyl]benzene, 1,3-bis[4-(4-aminophenoxy)-α,α-dimethylbenzyl]benzene, 1,4-bis[4-(3-aminophenoxy)-α,α-dimethylbenzyl]benzene, 1,4-bis[4-(4-aminophenoxy)-α,α-dimethylbenzyl]benzene, 4,4'-bis[4-(4-aminophenoxy)benzoyl]diphenyl ether, 4,4'-bis[4-(4-amino-α,α-dimethylbenzyl)phenoxy]benzophenone, 4,4'-bis[4-(4-amino-α,α-dimethylbenzyl)phenoxy]diphenyl sulfone, 4,4'-bis[4-(4-aminophenoxy)phenoxy]diphenyl sulfone, 3,3'-diamino-4,4'-diphenoxybenzophenone, 3,3'-diamino-4,4'-dibiphenoxybenzophenone, 3,3'-diamino-4-phenoxybenzophenone, 3,3'-diamono-4-biphenoxybenzophenone, 6,6'-bis(3-aminophenoxy)-3,3,3',3'-tetramethyl-1,1'-spirobiindan and 6,6'-bis(4-aminophenoxy)-3,3,3',3'-tetramethyl-1,1'-spirobiindan; aliphatic amines such as 1,3-bis(3-aminopropyl)tetramethyldisiloxane, 1,3-bis(4-aminobutyl)tetramethyldisiloxane, α,ω-bis(3-aminopropyl)polydimethylsiloxane, α,ω-bis(3-aminobutyl)polydimethylsiloxane, bis(aminomethyl)ether, bis(2-aminoethyl)ether, bis(3-aminopropyl)ether, bis(2-aminomethoxy)ethyl]ether, bis[2-(2-aminoethoxy)ethyl]ether, bis[2-(3-aminoprotoxy)ethyl]ether, 1,2-bis(aminomethoxy)ethane, 1,2-bis(2-aminoethoxy)ethane, 1,2-bis[2-(aminomethoxy)ethoxy]ethane, 1,2-bis[2-(2-aminoethoxy)ethoxy]ethane, ethylene glycol bis(3-aminopropyl)ether, diethylene glycol bis(3-aminopropyl)ether, triethylene glycol bis(3-aminopropyl)ether, ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane and 1,12-diaminododecane; and alicyclic diamines such as 1,2-diaminocyclohexane, 1,3-diaminocyclohexane, 1,4-diaminocyclohexane, 1,2-di(2-aminoethyl)cyclohexane, 1,3-di(2-aminoethyl)cyclohexane, 1,4-di(2-aminoethyl)cyclohexane, bis(4-aminocyclohexyl)methane, 2,6-bis(aminomethyl)bicyclo[2.2.1]heptane and 2,5-bis(aminomethyl)bicyclo[2.2.1]heptane. Guanamines include acetoguanamine and benzoguanamine. Also, it is possible to use a diamine which is obtained by replacing part or all of hydrogen atoms of the aromatic ring of any of the above diamines with a substituent selected from the group consisting of a fluoro group, a methyl group, a methoxy group, a trifluoromethyl group and a trifluoromethoxy group.

Furthermore, depending on the intended purpose, any one or two or more of an ethynyl group, a benzocyclobutene-4'-yl group, a vinyl group, an allyl group, a cyano group, an isocyanate group and an isopropenyl group can be introduced to part or all of the hydrogen atoms of the aromatic ring of any of the above diamines as a substituent, the groups serving as a crosslinking point.

The diamine can be selected depending on target properties, and in the case of using a rigid diamine such as p-phenylenediamine, the finally-obtained polyimide is provided with a low expansion coefficient. Examples of the rigid diamine include a diamine in which two amino groups are bound to one aromatic ring, such as p-phenylenediamine, m-phenylenediamine, 1,4-diaminonaphthalene, 1,5-diaminonaphthalene, 2,6-diaminonaphthalene, 2,7-diaminonaphthalene and 1,4-diaminoanthracene.

Moreover, there may be mentioned a diamine in which two or more aromatic rings are connected via a single bond and two or more amino groups are each bound to the different aromatic rings directly or as a part of a substituent, such as a diamine represented by the following formula (7). Specific examples thereof include benzidine.

[Chemical formula 14]

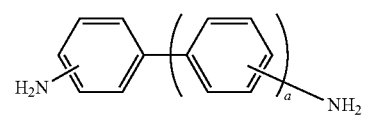

Formula (7)

In the formula (7), a is a natural number of 1 or more, and each of the amino groups is bound to the meta- or para-position of the bond between the benzene rings.

Also, there may be used a diamine which is represented by the formula (7) and in which a substituent is present in a position of each benzene ring, the position being not involved in bonding to the other benzene ring and not replaced with an amino group. The substituents are organic groups; however, they may be bound to each other.

Specific examples thereof include 2,2'-dimethyl-4,4'-diaminobiphenyl, 2,2'-ditrifluoromethyl-4,4'-diaminobiphenyl, 3,3'-dichloro-4,4'-diaminobiphenyl, 3,3'-dimethoxy-4,4'-diaminobiphenyl and 3,3'-dimethyl-4,4'-diaminobiphenyl.

In the case of using the finally-obtained polyimide as an optical waveguide or optical circuit component, it is possible to increase the transmittance of the polyimide for electromagnetic radiation at a wavelength of 1 μm or less by introducing a fluorine as a substituent of each aromatic ring.

In the case of using a diamine having a siloxane skeleton (e.g., 1,3-bis(3-aminopropyl)tetramethyldisiloxane) as the diamine, there is a decrease in the elastic modulus of the finally-obtained polyimide and thus a decrease in the glass transition temperature of the same.

From the viewpoint of heat resistance, the diamine selected herein is preferably an aromatic diamine. However, depending on target properties, a diamine other than aromatic diamine (e.g., aliphatic diamine and siloxane diamine) can be used in an amount that does not exceed 60% by mole, preferably 40% by mole of the whole diamine.

The polyimide precursor can be synthesized as follows, for example: a solution is prepared by dissolving 4,4'-diaminodiphenyl ether (amine component) in an organic polar solvent such as N-methylpyrrolidone; while cooling the solution, an equimolar 3,3',4,4'-biphenyltetracarboxylic dianhydride is gradually added thereto and stirred, thereby obtaining a polyimide precursor solution.

To provide heat resistance and dimensional stability to the finally-obtained polyimide, the copolymerization ratio of the aromatic acid component and/or the aromatic amine component in the polyimide precursor synthesized as above is preferably as large as possible. In particular, the aromatic acid component is preferably 50% by mole or more, more preferably 70% by mole or more of the acid component constituting the repeating unit of the imide structure; the aromatic amine component is preferably 40% by mole or more, more preferably 60% by mole or more of the amine component constituting the repeating unit of the imide structure; and a wholly aromatic polyimide is particularly preferable.

<Polybenzoxazole Precursor>

As the polybenzoxazole precursor used in the present invention, a polyamide alcohol having a repeating unit represented by the following chemical formula (8) is suitably used.

The polyamide alcohol can be synthesized by conventionally known methods. For example, it can be obtained by the addition reaction of a dicarboxylic acid derivative (e.g., dicarboxylic acid halide) with a dihydroxydiamine in an organic solvent.

[Chemical formula 15]

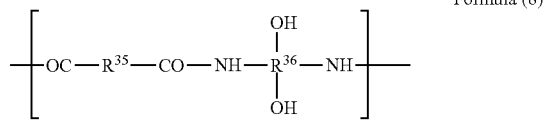

Formula (8)

In the chemical formula (8), $R^{35}$ is a divalent organic group; $R^{36}$ is a tetravalent organic group; and n is a natural number of 1 or more.

The divalence of $R^{35}$ refers only to a valence for bonding to acids; however, $R^{35}$ may have other substituent(s) further. Similarly, the tetravalence of $R^{36}$ refers only to a valence for bonding to amines and hydroxyl groups; however, $R^{36}$ may have other substituent(s) further.

To provide excellent heat resistance and dimensional stability to the finally-obtained polybenzoxazole, the polyamide alcohol having a repeating unit represented by the chemical formula (8) is preferably such that $R^{35}$ or $R^{36}$ of the chemical formula (8) is an aromatic compound, and it is more preferable that $R^{35}$ and $R^{36}$ of the chemical formula (8) are aromatic compounds. In this case, at $R^{35}$ of the chemical formula (8), two groups ((—CO—)$_2$) bound to $R^{35}$ can be bound to the same aromatic ring or different aromatic rings. Similarly, at $R^{36}$ of the chemical formula (8), four groups ((—NH—)$_2$(—OH)$_2$) bound to $R^{36}$ can be bound to the same aromatic ring or different aromatic rings.

The polyamide alcohol represented by the chemical formula (8) can be one comprising a single repeating unit or one comprising two or more kinds of repeating units.

Examples of the dicarboxylic acid or derivative thereof which can be applied to the reaction for obtaining the polybenzoxazole precursor include, but not limited to, phthalic acid, isophthalic acid, terephthalic acid, 4,4'-benzophenone dicarboxylic acid, 3,4'-benzophenone dicarboxylic acid, 3,3'-benzophenone dicarboxylic acid, 4,4'-biphenyldicarboxylic acid, 3,4'-biphenyldicarboxylic acid, 3,3'-biphenyldicarboxylic acid, 4,4'-diphenyl ether dicarboxylic acid, 3,4'-diphenyl ether dicarboxylic acid, 3,3'-diphenyl ether dicarboxylic acid, 4,4'-diphenyl sulfone dicarboxylic acid, 3,4'-diphenyl sulfone dicarboxylic acid, 3,3'-diphenyl sulfone dicarboxylic acid, 4,4'-hexafluoroisopropylidene dibenzoic acid, 4,4'-dicarboxydiphenylamide, 1,4-phenylenediethanoic acid, 1,1-bis(4-carboxyphenyl)-1-phenyl-2,2,2-trifluoroethane, bis(4-carboxyphenyl)tetraphenyldisiloxane, bis(4-carboxyphenyl)tetramethyldisiloxane, bis(4-carboxyphenyl) sulfone, bis(4-carboxyphenyl)methane, 5-t-butylisophthalic acid, 5-bromoisophthalic acid, 5-fluoroisophthalic acid, 5-chloroisophthalic acid, 2,2-bis-(p-carboxyphenyl)propane, 4,4'-(p-phenylenedioxy)dibenzoic acid, 2,6-naphthalenedicarboxylic acid, acid halides thereof, and active esters thereof with hydroxybenzotriazole or the like. They are used solely or in combination of two or more kinds.

Specific examples of the dihydroxydiamine include, but not limited to, 3,3'-dihydroxybenzidine, 3,3'-diamino-4,4'-dihydroxybiphenyl, 4,4'-diamino-3,3'-dihydroxybiphenyl, 3,3'-diamino-4,4'-dihydroxydiphenyl sulfone, 4,4'-diamino-3,3'-dihydroxydiphenyl sulfone, bis-(3-amino-4-hydroxyphenyl)methane, 2,2-bis-(3-amino-4-hydroxyphenyl)propane, 2,2-bis-(3-amino-4-hydroxyphenyl) hexafluoropropane, 2,2-bis-(4-amino-3-hydroxyphenyl) hexafluoropropane, bis-(4-amino-3-hydroxyphenyl) methane, 2,2-bis-(4-amino-3-hydroxyphenyl)propane, 4,4'-diamino-3,3'-dihydroxybenzophenone, 3,3'-diamino-4,4'-dihydroxybenzophenone, 4,4'-diamino-3,3'-dihydroxydiphenyl ether, 3,3'-diamino-4,4'-dihydroxydiphenyl ether, 1,4-diamino-2,5-dihydroxybenzene, 1,3-diamino-2,4-dihydroxybenzene, and 3-diamino-4,6-dihydroxybenzene. They may be used solely or in combination of two or more kinds.

The polymer precursor such as polyimide precursor or polybenzoxazole precursor preferably shows a transmittance of at least 5% or more, more preferably 15% or more for the exposure wavelength when it is formed into a film having a thickness of 1 μm, so that the photosensitive resin composition thus obtained is provided with high sensitivity and a pattern shape that can accurately reproduce a mask pattern is obtained.

The higher the transmittance of the polymer precursor (such as polyimide precursor or polybenzoxazole precursor) for the exposure wavelength, the smaller the loss of electromagnetic radiation. Therefore, a highly sensitive photosensitive resin composition can be obtained.

In the case of using a high pressure mercury lamp, which is a general exposing source, for exposure, the polymer precursor preferably has a transmittance of 5% or more, more preferably 15%, still more preferably 50% or more, for at least one of electromagnetic radiation wavelengths of 436 nm, 405 nm and 365 nm, when it is formed into a film having a thickness of 1 μm.

The polymer precursor such as polyimide precursor or polybenzoxazole precursor has a weight average molecular weight in the range of, although it depends on the intended use, preferably 3,000 to 1,000,000, more preferably 5,000 to 500,000, still more preferably 10,000 to 500,000. When the weight average molecular weight is less than 3,000, a coating or film made of the polymer precursor is not likely to have sufficient strength. Also, low strength is provided to a film formed from a polymer (e.g., polyimide) converted from the polymer precursor by heating treatment or the like. On the other hand, when the weight average molecular weight exceeds 1,000,000, the viscosity of the polymer precursor is increased and the solubility of the same is likely to be decreased; therefore, it is difficult to obtain a coating or film having a smooth surface and uniform thickness.

The molecular weight used herein is a polystyrene-equivalent value obtained by gel permeation chromatography (GPC). It can be the molecular weight of the polymer precursor itself (e.g., polyimide precursor) or can be the molecular weight after a chemical imidization treatment is performed thereon with acetic anhydride or the like.

The solvent used for the synthesis of the polyimide precursor or polybenzoxazole precursor is preferably a polar solvent. Typical examples thereof include N-methyl-2-pyrrolidone, N-acetyl-2-pyrrolidone, N,N-dimethylformamide, N,N-dimethylacetamide, N,N-diethylformamide, N,N-diethylacetamide, N,N-dimethylmethoxyacetamide, dimethylsulfoxide, hexamethylphosphoramide, pyridine, dimethyl sulfone, tetramethylene sulfone, dimethyltetramethylene sulfone, diethylene glycol dimethyl ether, cyclopentanone, γ-butyrolactone and α-acetyl-γ-butyrolactone. They are used solely or in combination of two or more kinds. Besides, a non-polar solvent can be used in combination with the solvent, and examples thereof include benzene, benzonitrile, 1,4-dioxane, tetrahydrofuran, butyrolactone, xylene, toluene and cyclohexanone. These solvents are used as a dispersion medium for raw materials, a reaction control agent, an agent for controlling solvent volatilization from a product, a coating film smoothing agent, etc.

The solubility of the polyamic acid or polybenzoxazole precursor is decreased as the reaction of the same into a final product is promoted by the action of a basic substance. Therefore, when combined with a decrease in solubility which is due to the base generated from the base generator represented by the chemical formula (1), there is an advantage that the dissolution contrast between the exposed and unexposed regions of the photosensitive resin composition of the present invention can be increased further.

<Other Components>

The photosensitive resin composition of the present invention can be a simple mixture of the base generator represented by the chemical formula (1), one or more kinds of polymer precursors and a solvent. Also, it can be prepared by adding a photo- or heat-curable component, a non-polymerizable binder resin other than the polymer precursor, and other component to the mixture.

Various kinds of all-purpose solvents can be used as the solvent for dissolving, dispersing or diluting the photosensitive resin composition. In the case of using a polyamide acid as the precursor, a solution obtained by the synthesis reaction of the polyamide acid can be used as it is, and the solution can be mixed with other component as needed.

Usable all-purpose solvents include, for example, ethers such as diethyl ether, tetrahydrofuran, dioxane, diethylene glycol dimethyl ether, ethylene glycol diethyl ether, propylene glycol dimethyl ether, propylene glycol diethyl ether and diethylene glycol dimethyl ether; glycol monoethers (so-called cellosolves) such as ethylene glycol monomethyl ether, ethylene glycol monoethyl ether, propylene glycol monomethyl ether, propylene glycol monoethyl ether, diethylene glycol monomethyl ether and diethylene glycol monoethyl ether; ketones such as methyl ethyl ketone, acetone, methyl isobutyl ketone, cyclopentanone and cyclohexanone; esters such as ethyl acetate, butyl acetate, n-propyl acetate, i-propyl acetate, n-butyl acetate, i-butyl acetate, ester acetates of the glycol monoethers (e.g., methyl cellosolve acetate, ethyl cellosolve acetate), propylene glycol monomethyl ether acetate, propylene glycol monoethyl ether acetate, dimethyl oxalate, methyl lactate and ethyl lactate; alcohols such as ethanol, propanol, butanol, hexanol, cyclohexanol, ethylene glycol, diethylene glycol and glycerin; halogenated hydrocarbons such as methylene chloride, 1,1-dichloroethane, 1,2-dichloroethylene, 1-chloropropane, 1-chlorobutane, 1-chloropentane, chlorobenzene, bromobenzene, o-dichlorobenzene and m-dichlorobenzene; amides such as N,N-dimethylformamide, N,N-diethylformamide, N,N-dimethylacetamide, N,N-diethylacetamide and N,N-dimethylmethoxyacetamide; pyrrolidones such as N-methyl-2-pyrrolidone and N-acetyl-2-pyrrolidone; lactones such as γ-butyrolactone and α-acetyl-γ-butyrolactone; sulfoxides such as dimethylsulfoxide; sulfones such as dimethyl sulfone, tetramethylene sulfone and dimethyltetramethylene sulfone; amide phosphates such as hexamethylphosphoramide; and other organic polar solvents. In addition, there may be mentioned aromatic hydrocarbons such as such as benzene, toluene, xylene and pyridine, and other organic nonpolar solvents. These solvents are used solely or in combination.

Among them, preferred are polar solvents such as propylene glycol monomethyl ether, methyl ethyl ketone, cyclopentanone, cyclohexanone, ethyl acetate, propylene glycol monomethyl ether acetate, N,N-dimethylacetamide, N-methyl-2-pyrrolidone and γ-butyrolactone; aromatic hydrocarbons such as toluene; and mixed solvents thereof.

As the photocurable component, a compound having one or two or more ethylenically unsaturated bond can be used. Examples thereof include amide monomers, (meth)acrylate monomers, urethane (meth)acrylate oligomers, polyester (meth)acrylate oligomers and epoxy(meth)acrylates, hydroxyl group-containing (meth)acrylates and aromatic vinyl compounds such as such as styrene. In the case where the polyimide precursor has a carboxylic acid component (e.g., polyamic acid) in a structure thereof, the use of an ethylenically unsaturated bond-containing compound having a tertiary amino group allows formation of an ionic bond between the tertiary amino group and the carboxylic acid of the polyimide precursor. Therefore, there is an increase in the dissolution rate contrast between the exposed and unexposed regions.

In the case of using such a photocurable composition having an ethylenically unsaturated bond, a photoradical generator can be added further. Examples of the photoradical generator include benzoins such as benzoin, benzoin methyl ether, benzoin ethyl ether and benzoin isopropyl ether, and alkyl ethers thereof; acetophenones such as acetophenone, 2,2-dimethoxy-2-phenylacetophenone, 2,2-diethoxy-2-phenylacetophenone, 1,1-dichloroacetophenone, 1-hydroxyacetophenone, 1-hydroxycyclohexyl phenyl ketone, and 2-methyl-1-[4-(methylthio)phenyl]-2-morpholino-propane-1-on; anthraquinones such as 2-methylanthraquinone, 2-ethylanthraquinone, 2-t-butylanthraquinone, 1-chloroanthraquinone and 2-amylanthraquinone; thioxanthones such as 2,4-dimethylthioxanthone, 2,4-diethylthioxanthone, 2-chlorothioxanthone and 2,4-diisopylthioxanthone; ketals such as acetophenone dimethyl ketal and benzil dimethyl ketal; monoacyl phosphine oxides such as 2,4,6-trimethylbenzoyl diphenylphosphine oxide and bisacyl phosphine oxides; benzophenones such as benzophenone; and xanthones.

To the extent that does not inhibit the advantageous effects of the present invention, other photosensitive component can be added to the photosensitive resin composition of the present invention, the component playing a supplementary role to the base generator of the present invention and generating an acid or base by exposure to light. Also, a base amplifier and/or sensitizer can be added thereto.

Examples of the compound which generates an acid by exposure to light include photosensitive diazoquinone compounds having a 1,2-benzoquinonediazide or 1,2-naphthoquinonediazide structure. Such compounds are described in the specifications of U.S. Pat. Nos. 2,772,972, 2,797,213 and 3,669,658. Also, a conventionally known photobase generator can be used, such as triazine and derivatives thereof, an oxime sulfonate compound, an iodonium sulfonate and a sulfonium sulfonate. Examples of the compound which generates a base by exposure to light include 2,6-dimethyl-3,5-dicyano-4-(2'-nitrophenyl)-1,4-dihydropyridine, 2,6-dimethyl-3,5-diacetyl-4-(2'-nitrophenyl)-1,4-dihydropyridine, and 2,6-dimethyl-3,5-diacetyl-4-(2',4'-dinitrophenyl)-1,4-dihydropyridine.

A base amplifier can be used in combination, which is decomposed or causes a rearrangement reaction by the action of a small amount of base generated from the base generator, thereby generating a base. Examples of the base amplifier include a compound having a 9-fluorenylmethyl carbamate bond, a compound having a 1,1-dimethyl-2-cyanomethyl carbamate bond $HON)CH_2C(CH_3)_2OC(O)NR_2)$, a compound having a p-nitrobenzyl carbamate bond, and a compound having a 2,4-dichlorobenzyl carbamate bond, and urethane-based compounds described in paragraphs [0010] to [0032] of Japanese Patent Application Laid-Open (JP-A) No. 2000-330270 and paragraphs [0033] to [0060] of JP-A No. 2008-250111, for example.

Addition of a sensitizer can be effective when it is required to increase the sensitivity of the photosensitive resin composition by allowing the base generator to sufficiently utilize the energy of electromagnetic waves at a wavelength that passes through the polymer.

Especially in the case where the polyimide precursor has absorption at a wavelength of 360 nm or more, addition of a sensitizer is particularly effective. Specific examples of compounds called sensitizers include thioxanthone and derivatives thereof such as diethylthioxanthone, coumarins and derivative thereof, ketocoumarin and derivatives thereof, ketobiscoumarin and derivatives thereof, cyclopentanone and derivatives thereof, cyclohexanone and derivatives thereof, thiopyrylium salts and derivatives thereof, thioxanthenes and derivatives thereof, and xanthenes and derivatives thereof.

Specific examples of coumarins, ketocoumarin and derivatives thereof include 3,3'-carbonylbiscoumarin, 3,3'-carbonylbis(5,7-dimethoxycoumarin) and 3,3'-carbonylbis(7-acetoxycoumarin). Specific examples of thioxanthone and derivatives thereof include diethylthioxanthone and isopropylthioxanthone. In addition, there may be mentioned benzophenone, acetophenone, phenanthrene, 2-nitrofluorene, 5-nitroacenaphthene, benzoquinone, 2-ethylanthraquinone, 2-tert-butylanthraquinone, 1,2-benzanthraquinone, 1,2-naphthoquinone, etc.

They exert particularly excellent effects when combined with a base generator, so that a sensitizer which exerts optimal sensitizing effects is appropriately selected depending on the structure of the base generator.

Other various kinds of organic or inorganic, low- or high-molecular-weight compounds can be added further to provide processability and various kinds of functionality to the resin composition of the present invention. For example, there may be used a dye, a surfactant, a leveling agent, a plasticizer, fine particles, etc. Examples of the fine particles include organic fine particles such as polystyrene and polytetrafluoroethylene, and inorganic fine particles such as colloidal silica, carbon and phyllosilicate. They can be porous or hollow. Functions or forms thereof include a pigment, filler, fiber, etc.

From the viewpoint of film physical properties of the resulting pattern, especially film strength and heat resistance, the polymer precursor (solid content) contained in the photosensitive resin composition of the present invention is generally 30% by weight or more, preferably 50% by weight or more of the total solid content of the photosensitive resin composition.

The base generator represented by the chemical formula (1) is generally contained in the range of 0.1 to 95% by weight, preferably in the range of 0.5 to 60% by weight of the solid content of the polymer precursor contained in the photosensitive resin composition. If less than 0.1% by weight, the dissolution contrast between the exposed and unexposed regions could not be increased sufficiently. If more than 95% by weight, properties of the finally-obtained cured resin are poorly reflected in the final product.

In the case of using the base generator as a curing agent, such as the case of mixing the base generator with an epoxy compound, the base generator is generally in the range of 0.1 to 95% by weight, preferably in the range of 0.5 to 60% by weight of the solid content of the polymer precursor contained in the photosensitive resin composition, depending of the degree of curing.

In the case of using the base generator as a curing accelerator, the photosensitive resin composition can be cured by adding the base generator in a small amount. The base generator represented by the chemical formula (1) is generally contained in the range of 0.1 to 30% by weight, preferably in the range of 0.5 to 20% by weight of the solid content of the polymer precursor contained in the photosensitive resin composition.

In the photosensitive resin composition of the present invention, the polymer precursor (solid content) is generally 50.1 to 99.9% by weight, preferably 62.5 to 99.5% by weight of the total solid content of the photosensitive resin composition. The base generator represented by the chemical formula (1) is generally 0.1 to 49.9% by weight, preferably 0.5 to 37.5% by weight of the total solid content of the photosensitive resin composition.

The solid content of the photosensitive resin composition refers to all components other than a solvent and includes a liquid monomer component.

A mixing ratio of other optional component(s) other than a solvent is preferably in the range of 0.1% by weight to 95% by weight of the total solid content of the photosensitive resin composition. If less than 0.1% by weight, addition of the additive(s) is not effective very much. If more than 95% by weight, properties of the finally-obtained cured resin are poorly reflected in the final product.

The photosensitive resin composition of the present invention can be used in various kinds of coating and molding processes and can produce films and three-dimensional molded products.

As an embodiment of the photosensitive resin composition of the present invention, in the case of using the polyimide precursor or polybenzoxazole precursor as the polymer precursor, the thus-obtained polyimide or polybenzoxazole has a 5% weight loss temperature measured in a nitrogen atmosphere of preferably 250° C. or more, more preferably 300° C. or more from the viewpoint of obtaining properties such as heat resistance, dimensional stability and insulation. Especially in the case where the photosensitive resin composition is used for an application such as an electronic component that undergoes a solder reflow process, if the thus-obtained polyimide or polybenzoxazole has a 5% weight loss temperature is 300° C. or less, a defect such as air bubbles could be caused by cracked gas produced in the solder reflow process.

Glass transition temperature of the polyimide and polybenzoxazole obtained from the photosensitive resin composition of the present invention is preferably as high as possible from the viewpoint of heat resistance. However, in applications in which a thermoforming process is expected, such as an optical waveguide, the polyimide and polybenzoxazole preferably shows a glass transition temperature of about 120° C. to 450° C., more preferably about 200° C. to 380° C.

When the polyimide or polybenzoxazole obtained from the photosensitive resin composition can be formed into a film, the glass transition temperature of the present invention is obtained from the peak temperature of tan δ (tan δ=loss elastic modulus (E")/storage elastic modulus (E')) by dynamic viscoelasticity measurement. The dynamic viscoelasticity measurement can be carried out with a viscoelasticity analyzer such as Solid Analyzer RSA II (manufactured by Rheometric Scientific Inc.) at a frequency of 3 Hz and a heating rage of 5° C./min. When the polyimide or polybenzoxazole obtained from the photosensitive resin composition cannot be formed into a film, the glass transition temperature is determined from the temperature of an inflection point of the baseline of a differential thermal analysis (DTA).

From the viewpoint of dimensional stability of the polyimide and polybenzoxazole obtained from the photosensitive resin composition of the present invention, the linear thermal expansion coefficient is preferably 60 ppm or less, more preferably 40 ppm or less. To form a film on a silicon wafer in the process of manufacturing a semiconductor device, etc., the linear thermal expansion coefficient is still more preferably 20 ppm or less from the viewpoint of adhesion and substrate warpage.

In the present invention, the linear thermal expansion coefficient can be obtained by measuring a film of the polyimide or polybenzoxazole obtained from the photosensitive resin composition of the present invention with a thermal mechanical analyzer (TMA). It can be obtained with a thermal mechanical analyzer (such as Thermo Plus TMA8310 manufactured by Rigaku Corporation) at a heating rate of 10° C./min and a tensile load of 1 g/25,000 $\mu m^2$ so that a uniform load is applied to per cross-sectional area of an evaluation sample.

As described above, according to the present invention, the photosensitive resin composition can be obtained by such a simple method of mixing the polymer precursor with the base generator represented by the chemical formula (1); therefore, the present invention provides excellent cost performance.

An aromatic component-containing carboxylic acid and basic substance which constitute the base generator represented by the chemical formula (1) are available at low cost; therefore, the price of the photosensitive resin composition can be low.

Due to the base generator represented by the chemical formula (1), the photosensitive resin composition of the present invention can be used to promote the reaction of various kinds of polymer precursors into a final product, and the structure of the finally-obtained polymer can be selected from a wide range of structures.

Also, due to the catalytic effect of the basic substance (e.g., amine) generated by exposure to electromagnetic radiation, it is possible to decrease a process temperature that is required for a reaction such as cyclization (e.g., imidization of the polyimide precursor or polybenzoxazole precursor into a final product). Therefore, it is possible to reduce the load on the process and heat damage to a final product.

In addition, when a heating step is included in the process of obtaining a final product from the polymer precursor, the heating step can be utilized by the base generator of the present invention which generates a base by exposure to electromagnetic radiation and heating; therefore, it is possible to reduce the amount of electromagnetic radiation and to use the step efficiently.

The photosensitive resin composition of the present invention can be used in all conventionally-known fields and products which use a resin material, such as a printing ink, a paint, a sealing agent, an adhesive, an electronic material, an optical circuit component, a molding material, a resist material, a building material, a stereolithography product and an optical element. It can be suitably used in any of applications such as an application in which the photosensitive resin composition is subjected to whole surface exposure, such as a paint, a sealing agent and an adhesive, and an application in which the photosensitive resin composition is used to form a pattern, such as a permanent film and a stripping film.

The photosensitive resin composition of the present invention is suitably used in a wide range of fields and products for which properties such as heat resistance, dimensional stability and insulation are effective, such as a paint, a printing ink, a sealing agent, an adhesive or a material for forming displays, semiconductor devices, electronic components, microelectromechanical systems (MEMS), optical elements or building materials. For example, in particular, as the material for forming electronic components, the photosensitive resin composition can be used for a printed wiring board, an interlayer insulating film, a wire cover film or the like as an encapsulating material or layer forming material. As the material for forming displays, the photosensitive resin composition can be used for a color filter, a film for flexible displays, a resist material, an orientation film or the like as a layer forming material or image forming material. As the material for forming semiconductor devices, it can be used as a resist material, a material for forming layers such as a buffer coat film, etc. As the material for forming optical components, it can be used for a hologram, an optical, waveguide, an optical circuit, an optical circuit component, an antireflection film or the like as an optical material or layer forming material. As the building material, it can be used for a paint, a coating agent or the like. Also, it can be used as the material for stereolithography products. The photosensitive resin composition of the present invention provides any of the following articles: a paint, a sealing agent, an adhesive, a display, a semiconductor device, an electronic component, a microelectromechanical system, a stereolithography product, an optical element and a building material.

Because of having the above characteristics, the photosensitive resin composition of the present invention can be also used as a pattern forming material. Especially in the case where the photosensitive resin composition containing the polyimide precursor or polybenzoxazole precursor is used as a pattern forming material (resist), the pattern formed therewith is a permanent film that comprises polyimide or polybenzoxazole and functions as a component which provides heat resistance or insulation property. For example, it is suitable to form a color filter, a film for flexible displays, an electronic component, a semiconductor device, an interlayer insulating film, a wire cover film, an optical circuit, an optical circuit component, an antireflection film, other optical element or an electronic member.

<Pattern Forming Method>

The pattern forming method of the present invention is a method for forming a pattern by forming a coating film or molded body with the photosensitive resin composition of the present invention, exposing the coating film or molded body to electromagnetic radiation in a predetermined pattern, heating the coating film or molded body after or at the same time as the exposure to change the solubility of the exposed region, and then developing the coating film or molded body.

A coating film is formed by applying the photosensitive resin composition of the present invention onto a substrate of some sort, or a molded body is formed by an appropriate molding method using the photosensitive resin composition. The coating film or molded body is exposed to electromagnetic radiation in a predetermined pattern and heated after or at the same time as the exposure, so that the base generator represented by the chemical formula (1) is isomerized and cyclized only in the exposed region, thereby generating a basic substance. The basic substance functions as a catalyst that promotes the reaction of the polymer precursor in the exposed region into a final product.

In the case of using a polymer precursor of which thermal curing temperature can be decreased by the catalytic reaction of a base, such as a polyimide precursor and polybenzoxazole precursor, a region where a pattern is required to be left on the coating film or molded body formed with the photosensitive resin composition is exposed first, the photosensitive resin composition comprising a combination of such a polymer precursor and the base generator represented by the chemical formula (1). By heating the same after or at the same time as the exposure, a basic substance is generated in the exposed region and the thermal curing temperature of the region is selectively decreased. After or at the same time as the exposure, the coating film or molded body is heated at a treatment temperature at which the exposed region is thermally cured while the unexposed region is not, thereby curing only the exposed region. The heating process for generating a basic substance and another heating process for causing a reaction to cure the exposed region only (post exposure bake) can be one single process or different processes. Next, the unexposed region is dissolved with a predetermined developer (such as an organic solvent or basic aqueous solution) to form a pattern comprising a thermally-cured product. This pattern is heated further as needed to finish thermal curing. A desired two-dimensional resin pattern (general plane pattern) or three-dimensional resin pattern (three-dimensionally formed pattern) is obtained by these processes, both of which are normally negative patterns.

Even in the case of using a polymer precursor that can initiate a reaction by the catalytic action of a base, such as a compound or polymer having an epoxy or cyanate group, the region where a pattern is required to be left on the coating film or molded body formed with the photosensitive resin composition is exposed first, the photosensitive resin composition comprising a combination of such a polymer precursor and the base generator represented by the chemical formula (1). By heating the same after or at the same time as the exposure, a basic substance is generated in the exposed region and thus the compound or polymer having an epoxy or cyanate group in the region initiates a reaction to cure only the exposed region. The heating process for generating a basic substance and another heating process for causing a reaction to cure the exposed region only (post exposure bake) can be one single process or different processes. Next, the unexposed region is dissolved with a predetermined developer (such as an organic solvent or basic aqueous solution) to form a pattern comprising a thermally-cured product. This pattern is heated further as needed to finish thermal curing. A desired two-dimensional resin pattern (general plane pattern) or three-dimensional resin pattern (three-dimensionally formed pattern) is obtained by these processes, both of which are normally negative patterns.

The photosensitive resin composition of the present invention forms a non-adhesive coating film on a substrate by: dissolving the same in a polar solvent (such as propylene glycol monomethyl ether, methyl ethyl ketone, cyclopentanone, cyclohexanone, ethyl acetate, propylene glycol monomethyl ether acetate, N,N-dimethylacetamide, N-methyl-2-pyrrolidone or γ-butyrolactone), an aromatic hydrocarbon such as toluene, or a mixed solvent thereof; applying the mixture onto a surface of a substrate such as a silicon wafer, metal substrate, ceramic substrate or resin film by a dipping method, spraying method, flexographic printing method, gravure printing method, screen printing method, spin coating method, dispensing method or the like; and heating the applied coating film to remove most of the solvent, thereby forming the film. A thickness of the coating film is not particularly limited and is preferably 0.5 to 50 μm. From the viewpoint of sensitivity and development rate, it is more preferably 1.0 to 20 μm. A drying condition of the applied coating film is a temperature of 80 to 100° C. and a time of 1 to 20 minutes, for example.

The coating film is exposed to electromagnetic radiation through a mask having a predetermined pattern so as to be exposed in a predetermined pattern. After heating, the film is developed with an appropriate developer to remove the unexposed region of the film, thereby obtaining a desirably patterned film.

An exposing method and device used in the exposure process are not particularly limited. The method can be contact exposure or indirect exposure. As the device, there may be used a contact-proximity exposure system using a g-line stepper, i-line stepper or super high pressure mercury lamp, a mirror projection exposure system, or other projection device or radiation source which can emit ultraviolet light, visible light, X-ray, electron beam or the like.

In the case of deprotecting a protecting group by exposure to electromagnetic radiation, the electromagnetic radiation used for the deprotection can be the same as or different from that for generating a base. For example, deprotection can be performed by exposure to electromagnetic radiation at a long wavelength, and then isomerization can be carried out by exposure to electromagnetic radiation at a short wavelength to generate a base. An amount of electromagnetic radiation varies depending on the type of electromagnetic radiation, and it is not particularly limited and is appropriately controlled.

The heating temperature for deprotecting the protecting group and generating a base before, after or at the same time as the exposure is appropriately determined depending on the polymer precursor to be combined or on the intended purpose, and it is not particularly limited. The heating can be heating at a temperature of the environment where the photosensitive resin composition is placed (e.g., room temperature) and in this case, bases are gradually generated. Bases are also generated by heat that is produced as a by-product of the exposure to electromagnetic radiation, so that heating can be substantially performed at the same time by the heat produced as the by-product. To increase the reaction rate and efficiently generate an amine, the heating temperature for generating a base is preferably 30° C. or more, more preferably 60° C. or more, still more preferably 100° C. or more, and particularly preferably 120° C. or more. However, the suitable heating temperature is not limited thereto because the unexposed region can be cured by heating at 60° C. or more for example, depending on the type of the polymer precursor used in combination.

For example, in the case of an epoxy resin, the preferred temperature range of heat treatment is appropriately determined depending on the type of the epoxy resin; however, it is generally about 100° C. to 150° C.

Only the deprotection of a protecting group can be performed by heating before the exposure. The heating for deprotecting a protecting group before the exposure to electromagnetic radiation can be a coating film drying process or other heating process. In this case, as the heating temperature, a temperature at which the deprotection is possible can be appropriately selected. It is preferably a temperature of 50° C. to 180° C. and the time is preferably 10 seconds or more and 60 minutes or less.

To physically promote a crosslinking reaction or initiate a reaction for curing only the exposed region, it is preferable to perform a post exposure bake (PEB) on the coating film of the photosensitive resin composition of the present invention between the exposure and developing processes. The PEB is preferably performed at a temperature at which, due to the action of the base generated by the exposure to electromagnetic radiation and heating, the reaction rate of a curing reaction (e.g., imidization rate) will be different between regions where the base is present and not present. For example, in the case of imidization, the preferred temperature range of heat treatment is generally about 60° C. to 200° C., more preferably 120° C. to 200° C. When the heat treatment temperature is less than 60° C., imidization is not efficient and it is difficult to cause a difference between the imidization rate of the exposed region and that of the unexposed region under a realistic process condition. When the heat treatment temperature exceeds 200° C., imidization could proceed even in the unexposed region where no amine is present, so that it is difficult to cause a difference between the solubility of the exposed region and that of the unexposed region.

The heat treatment can be performed by any conventionally method. A specific example thereof is, but not particularly limited to, heating with a circulation-type oven or hot plate in the air or a nitrogen atmosphere.

In the present invention, a base is generated from the base generator by exposure to electromagnetic radiation and heating; however, the heating for generating a base and PEB process can be one single process or different processes.

(Developer)

The developer used in the developing process is not particularly limited as long as it is a solvent which can change the solubility of the exposed region. It can be appropriately selected from basic aqueous solutions, organic solvents and so on, depending on the used polymer precursor.

The basic aqueous solutions are not particularly limited and include, for example, a tetramethylammonium hydroxide (TMAH) aqueous solution in a concentration of 0.01% by weight to 10% by weight (preferably 0.05% by weight to 5% by weight) and aqueous solutions of diethanolamine, diethyl amino ethanol, sodium hydroxide, potassium hydroxide, sodium carbonate, potassium carbonate, sodium hydrogencarbonate, potassium hydrogencarbonate, triethylamine, diethylamine, methylamine, dimethylamine, dimethylamino ethyl acetate, dimethylaminoethanol, dimethylamino ethyl methacrylate, cyclohexylamine, ethylenediamine, hexamethylenediamine, tetramethylammonium and so on.

A solute can be one or more kinds of solutes. The basic aqueous solution can contain an organic solvent or the like when it contains water in an amount of 50% or more, more preferably 70% or more of the total weight thereof.

The organic solvent is not particularly limited. As the organic solvent, polar solvents such as N-methyl-2-pyrrolidone, N,N-dimethylformamide, N,N-dimethylacetamide, dimethylsulfoxide, γ-butyrolactone and dimethylacrylamide, alcohols such as methanol, ethanol and isopropanol, esters such as ethyl acetate and propylene glycol monomethyl ether acetate, ketones such as cyclopentanone, cyclohexanone, isobutyl ketone and methyl isobutyl ketone, and other organic solvents such as tetrahydrofuran, chloroform and acetonitrile, can be used solely or in combination of two or more kinds. After the development, washing is performed with water or a poor solvent. Even in this case, an alcohol such as ethanol or isopropyl alcohol, an ester such as ethyl lactate or propylene glycol monomethyl ether acetate, etc., can be added to water.

After the development, to stabilize the pattern, rinsing with water or a poor solvent is performed as needed and then drying is performed at a temperature of 80 to 100° C. To make the resulting relief pattern heat resistant, it is heated at a temperature of 180 to 500° C., more preferably 200 to 350° C. for several ten minutes to several hours, thereby forming a patterned, highly heat-resistant resin layer.

EXAMPLES

Hereinafter, the present invention will be described in detail by way of examples. The scope of the present invention is not restricted by these examples. All designations of "part" or "parts" are part or parts by weight unless otherwise specifically indicated. Structures of base generators generated in the following examples were confirmed by $^1$H NMR.

Measurements and experiments were carried out by means of the following devices:

$^1$H NMR measurement: JEOL JNM-LA400WB manufactured by JEOL Ltd.

Manual exposure: MA-1100 manufactured by Japan Science Engineering Co., Ltd.

Measurement of absorbance: Ultraviolet-visible spectrophotometer UV-2550 manufactured by Shimadzu Corporation Heating of coating film: HOT PLATE EC-1200 manufactured by AS ONE Corporation (it may be referred to as "hot plate" in the following examples)

Production Example 1

Synthesis of Base Generator

In a 100 mL three-necked flask under a nitrogen flow, 0.50 g (3.1 mmol) of o-coumaric acid (manufactured by Tokyo Chemical Industry Co., Ltd.) was dissolved in 40 mL of dehydrated tetrahydroxyfuran, and 0.59 g (3.1 mmol, 1.0 eq) of 1-ethyl-3-(3-dimethylaminopropyl) carbodiimide hydrochloride (manufactured by Tokyo Chemical Industry Co., Ltd.) was added thereto. In an ice bath, 0.3 ml (3.1 mmol, 1.0 eq) of piperidine (manufactured by Tokyo Chemical Industry Co., Ltd.) was added thereto and the resultant was stirred at room temperature for one night. A reaction solution thus obtained was condensed. The condensed reaction solution was extracted with chloroform to obtain an extract. The extract was washed with dilute hydrochloric acid, a sodium hydrogen carbonate solution and then a salt solution, and subjected to filtration, thereby obtaining 450 mg of a compound represented by the following formula (10). In a 100 mL flask, 0.25 g (1.1 mmol) of the compound represented by the formula (10) and 0.17 mL (1.2 mmol, 0.55 eq) of cyclohexyl vinyl ether (manufactured by Tokyo Chemical Industry Co., Ltd.) were dissolved in 5 mL of dimethylformamide, followed by addition of 27.5 mg (110 μmol, 0.05 eq) of pyridinium p-toluenesulfonate, and stirring for one night. A reaction solution thus obtained was condensed. The condensed reaction solution was extracted with ethyl acetate to obtain an extract. The extract was purified by silica-gel column chromatography (developing solvent: hexane/ethyl acetate 10/1 to 1/1), thereby obtaining 110 mg of a base generator (1) represented by the following formula (11).

[Chemical formula 16]

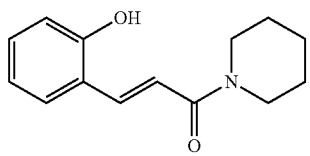

Formula (10)

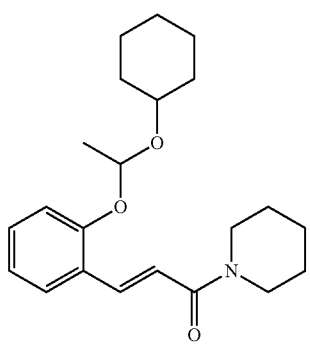

Formula (11)

Production Example 2

Synthesis of Base Generator)

A compound represented by the formula (10) was obtained in the same manner as Production example 1. In a 100 mL flask, 0.25 g (1.1 mmol) of the compound represented by the formula (10) was dissolved in a mixed solution of 1 g of tert-butyl vinyl ether (manufactured by Aldrich Inc.) and 4 g of dehydrated tetrahydrofuran. 110 mg (0.43 mmol, 0.1 eq) of pyridinium p-toluenesulfonate (manufactured by Tokyo Chemical Industry Co., Ltd.) was added thereto and the resultant was stirred for one night. After reaction was completed, saturated saline was added thereto. The resultant was extracted with ethyl acetate to obtain an extract. The extract was dried with magnesium sulfate and purified by open column chromatography (hexane:ethyl acetate=2:1 (volume ratio)), thereby obtaining 50 mg of a base generator (2) represented by the following formula (12):

[Chemical formula 17]

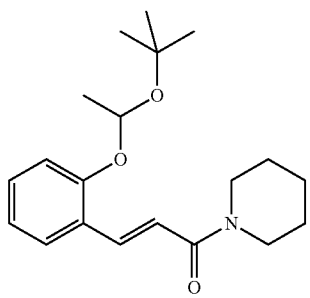

Formula (12)

Production Example 3

Synthesis of Base Generator)

A compound represented by the formula (10) was obtained in the same manner as Production example 1. In a 100 mL flask, 0.25 g (1.1 mmol) of the compound represented by the formula (10) was dissolved in a mixed solution of 110 mg (0.43 mmol, 0.1 eq) of pyridinium p-toluenesulfonate (manufactured by Tokyo Chemical Industry Co., Ltd.) and 4 g of dehydrated tetrahydrofuran. 1 g of 3,4-dihydro-2H-pyran (manufactured by Aldrich Inc.) was added thereto and the resultant was stirred for one night. After reaction was completed, saturated saline was added to thereto. The resultant was extracted with ethyl acetate to obtain an extract. The extract was washed with saturated saline, dried with magnesium sulfate and purified by open column chromatography (hexane:ethyl acetate=2:1 (volume ratio)), thereby obtaining 40 mg of a base generator (3) represented by the following formula (13):

[Chemical formula 18]

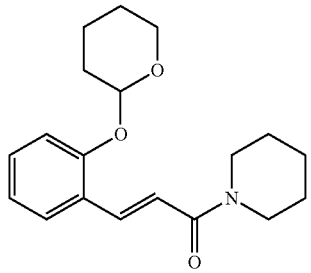

Formula (13)

Production Example 4

Synthesis of Base Generator

In a 100 mL flask, 2.00 g of potassium carbonate was added to 15 mL of methanol. In a 50 mL flask, 2.67 g (6.2 mmol) of ethoxycarbonylmethyl(triphenyl)phosphonium bromide and 945 mg (6.2 mmol) of 2-hydroxy-4-methoxybenzaldehyde were dissolved in 10 mL of methanol. The resultant was gradually added to a well-stirred potassium carbonate solution in a dropwise manner. After stirring the resultant for 3 hours, completion of reaction was confirmed by TLC. The resultant was filtered to exclude potassium carbonate and subjected to vacuum concentration. After the concentration, 50 mL of a 1 N sodium hydroxide aqueous solution was added thereto and the resultant was stirred for one hour. After reaction was completed, a reaction solution thus obtained was filtered to exclude triphenylphosphine oxide, and concentrated hydrochloric acid was added thereto in a dropwise manner to make the reaction solution an acidic solution. A precipitate thus produced was collected by filtration and washed with a small amount of chloroform, thereby obtaining 1.00 g of 2-hydroxy-4-methoxycinnamic acid. Then, in a 100 mL three-necked flask, 1.00 g (6.0 mmol) of 2-hydroxy-4-methoxycinnamic acid was dissolved in 40 mL of dehydrated tetrahydroxyfuran, and 1.41 g (7.2 mmol) of 1-ethyl-3-(3-dimethylaminopropyl)carbodiimide hydrochloride (EDC) was added thereto. After 30 minutes, 0.72 ml (7.2 mmol) of piperidine was added thereto. After reaction was completed, a reaction solution thus obtained was condensed and dissolved in water. The resulting solution was extracted with chloroform to obtain an extract. The extract was washed with a saturated sodium hydrogen carbonate aqueous solution, 1 N hydrochloric acid and then saturated saline, and then washed with a small amount of chloroform, thereby obtaining 1.03 g of a compound represented by the following formula (14).

In a 100 mL flask, 1.00 g (3.6 mmol) of the compound represented by the formula (14) was dissolved in a mixed solution of 4 g of tert-butyl vinyl ether (manufactured by Aldrich Inc.) and 4 g of dehydrated tetrahydrofuran. 91 mg (0.36 mmol, 0.1 eq) of pyridinium p-toluenesulfonate (manufactured by Tokyo Chemical Industry Co., Ltd.) was added thereto and the resultant was stirred for one night. After reaction was completed, saturated saline was added thereto. The resultant was extracted with ethyl acetate to obtain an extract. The extract was washed with saturated saline, dried with magnesium sulfate and purified by open column chromatography (hexane:ethyl acetate=2:1 (volume ratio)), thereby obtaining 60 mg of a base generator (4) represented by the following formula (15):

[Chemical formula 19]

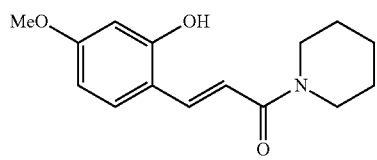

Formula (14)

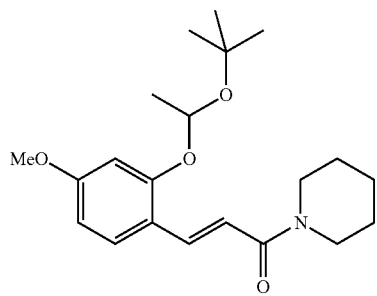

Formula (15)

Production Example 5

Synthesis of Base Generator

A compound represented by the formula (10) was obtained in the same manner as Production example 1. In a 100 mL flask, 0.25 g (1.1 mmol) of the compound represented by the formula (10), 0.28 g (1.3 mmol, 1.2 eq) of di-tert-butyl dicarbonate (manufactured by Tokyo Chemical Industry Co., Ltd.) and 0.23 ml (1.62 mmol, 1.5 eq) of triethylamine (manufactured by Tokyo Chemical Industry Co., Ltd.) were dissolved in 5 mL of chloroform and stirred for one night. After reaction was completed, saturated saline was added thereto. The resultant was extracted with ethyl acetate to obtain an extract. The extract was washed with saturated saline and dried with magnesium sulfate, thereby obtaining 160 mg of a base generator (5) represented by the following formula (16):

[Chemical formula 20]

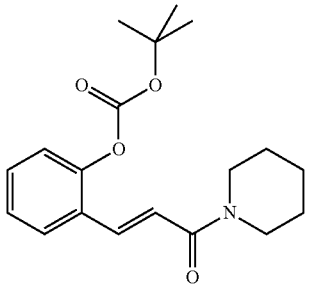

Formula (16)

Production Example 6

Synthesis of Base Generator

A compound represented by the formula (14) was obtained in the same manner as Production example 4. In a 100 mL flask, 1.00 g (3.6 mmol) of the compound represented by the formula (14) was dissolved in a mixed solution of 4 g of 2-vinyloxytetrahydropyran (manufactured by Tokyo Chemical Industry Co., Ltd.) and 4 g of dehydrated tetrahydrofuran. 91 mg (0.36 mmol, 0.1 eq) of pyridinium p-toluenesulfonate (manufactured by Tokyo Chemical Industry Co., Ltd.) was added thereto and the resultant was stirred for one night. After reaction was completed, saturated saline was added thereto. The resultant was extracted with ethyl acetate to obtain an extract. The extract was washed with saturated saline, dried with magnesium sulfate and purified by open column chromatography (hexane:ethyl acetate=2:1 (volume ratio)), thereby obtaining 82 mg of a base generator (6) represented by the following formula (17):

[Chemical formula 21]

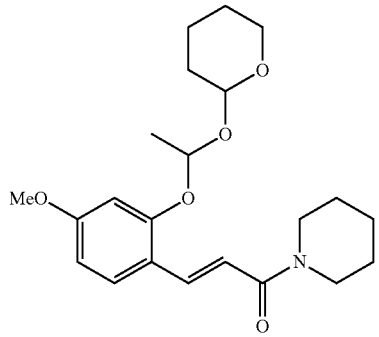

Formula (17)

Production Example 7

Synthesis of Base Generator

A compound represented by the formula (14) was obtained in the same manner as Production example 4. In a 100 mL flask, 1.00 g (3.82 mmol) of the compound represented by the formula (14) and 1.00 g (4.58 mmol, 1.2 eq) of di-tert-butyl dicarbonate (manufactured by Tokyo Chemical Industry Co., Ltd.) were dissolved in 5 mL of chloroform. A catalytic amount of N,N-dimethyl-4-aminopyridine (manufactured by Tokyo Chemical Industry Co., Ltd.) was added thereto and the resultant was stirred for one night. After reaction was completed, saturated saline was added thereto. The resultant was extracted with ethyl acetate to obtain an extract. The extract was washed with saturated saline and dried with magnesium sulfate, thereby obtaining 1.25 g of a base generator (7) represented by the following formula (18):

[Chemical formula 22]

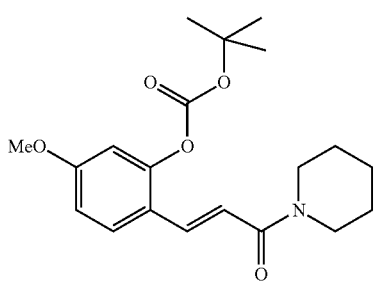

Formula (18)

Production Example 8

Synthesis of Base Generator

A compound represented by the formula (14) was obtained in the same manner as Production example 4. In a 100 mL flask, 1.00 g (3.82 mmol) of the compound represented by the formula (14) and 0.8 ml (5.74 mmol, 1.5 eq) of triethylamine (manufactured by Tokyo Chemical Industry Co., Ltd.) were dissolved in 10 mL of chloroform. 0.59 ml (4.21 mmol, 1.1 eq) of benzyl chloroformate (manufactured by Tokyo Chemical Industry Co., Ltd.) was added thereto and the resultant was stirred for one night. After reaction was completed, water was added thereto. The resultant was extracted with chloroform to obtain an extract. The extract was washed with saturated saline, dried with magnesium sulfate and recrystallized with ethyl acetate, thereby obtaining 0.89 g of a base generator (8) represented by the following formula (19):

[Chemical formula 23]

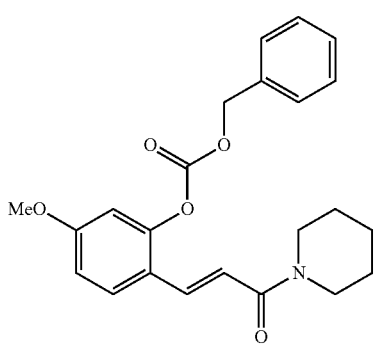

Formula (19)

Production Example 9

Synthesis of Base Generator

In a 100 mL flask in an ice bath, 10.0 g (60.9 mmol) of trans-o-coumaric acid and 21.2 mL (152 mmol, 2.5 eq) of triethylamine (manufactured by Tokyo Chemical Industry Co., Ltd.) were dissolved in 50 mL of tetrahydrofuran and 50 mL of dimethylformamide. After 12.7 g (57.9 mmol, 0.95 eq) of di-tert-butyl dicarbonate (manufactured by Tokyo Chemical Industry Co., Ltd.) was added thereto, a catalytic amount of N,N-dimethyl-4-aminopyridine (manufactured by Tokyo Chemical Industry Co., Ltd.) was added thereto and the resultant was stirred for one night. After reaction was completed, saturated saline was added thereto. The resultant was extracted with ethyl acetate to obtain an extract. The extract was washed with saturated saline and dried with magnesium sulfate, thereby obtaining 8.5 g of a compound A represented by the following formula (20). Then, in a 100 mL three-necked flask, 2.5 g (9.56 mmol) of the compound A was dissolved in 40 mL of dehydrated dimethylformamide. 2.02 g (1.1 eq) of 1-ethyl-3-(3-dimethylaminopropyl)carbodiimide hydrochloride (EDC) was added thereto. After 30 minutes, 540 mg (0.9 eq) of 1,6-hexanediamine (manufactured by Tokyo Chemical Industry Co., Ltd.) was added thereto. After reaction was completed, a reaction solution thus obtained was condensed and dissolved in water. The resulting solution was extracted with ethyl acetate to obtain an extract. The extract was condensed and recrystallized with a chloroform-ethyl acetate mixed solvent, thereby obtaining 250 mg of a base generator (9) represented by the following formula (21):

[Chemical formula 24]

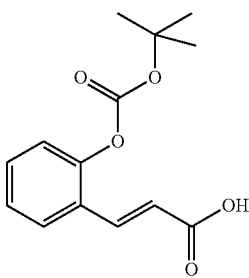

Formula (20)

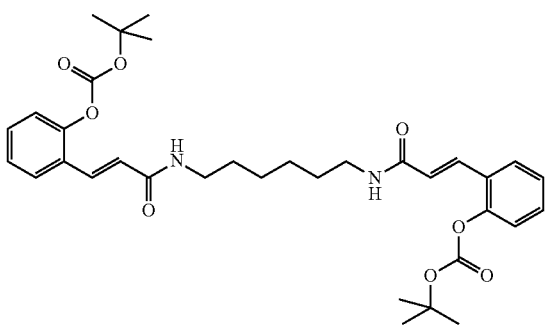

Formula (21)

Production Example 10

Synthesis of Base Generator

A compound represented by the formula (20) was obtained in the same manner as Production example 9. In a 100 mL three-necked flask, 2.5 g (9.56 mmol) of the compound A was dissolved in 40 mL of dehydrated dimethylformamide. 2.02 g (1.1 eq) of 1-ethyl-3-(3-dimethylaminopropyl)carbodiimide hydrochloride (EDC) was added thereto. After 30 minutes, 2.40 g (0.9 eq) of p-xylylenediamine (manufactured by Tokyo Chemical Industry Co., Ltd.) was added thereto. After reaction was completed, a reaction solution thus obtained was condensed and dissolved in water. The resulting solution was extracted with ethyl acetate to obtain an extract. The extract was condensed and recrystallized with a chloroform-ethyl acetate mixed solvent, thereby obtaining 250 mg of a base generator (10) represented by the following formula (22):

[Chemical formula 25]

Formula (22)

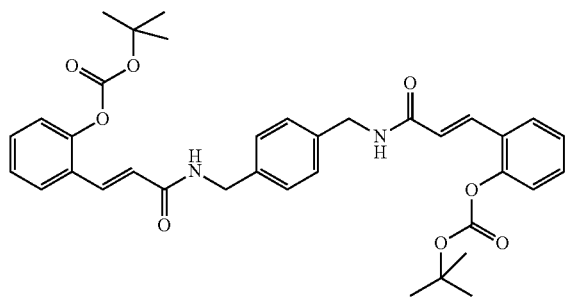

Production Example 11

Synthesis of Base Generator

A compound represented by the formula (14) was obtained in the same manner as Production example 4. In a 100 mL flask, 1.00 g (3.82 mmol) of the compound represented by the formula (14) and 0.69 g (4.58 mmol, 1.2 eq) of tert-butyldimethylchlorosilane (manufactured by Tokyo Chemical Industry Co., Ltd.) were dissolved in 5 mL of dimethylsulfoxide. 650 mg (9.58 mmol, 2.5 eq) of imidazole (manufactured by Tokyo Chemical Industry Co., Ltd.) was added thereto and stirred for one night. After reaction was completed, a 5% sodium hydrogen carbonate solution was added thereto. The resultant was extracted with ethyl acetate to obtain an extract. The extract was washed with saturated saline and dried with magnesium sulfate, thereby obtaining 0.89 g of a base generator (11) represented by the following formula (23):

[Chemical formula 26]

Formula (23)

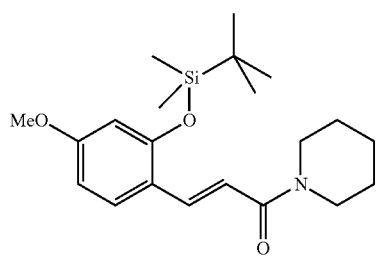

Production Example 12

Synthesis of Base Generator

A compound represented by the formula (10) was obtained in the same manner as Production example 1. In a 100 mL flask, 0.25 g (1.1 mmol) of the compound represented by the formula (10), 0.12 ml (1.3 mmol, 1.2 eq) of acetic anhydride (manufactured by Tokyo Chemical Industry Co., Ltd.) and 0.23 ml (1.62 mmol, 1.5 eq) of triethylamine (manufactured by Tokyo Chemical Industry Co., Ltd.) were dissolved in 5 mL of chloroform and stirred for one night. After reaction was completed, saturated saline was added thereto. The resultant was extracted with ethyl acetate to obtain an extract. The extract was washed with saturated saline and dried with magnesium sulfate, thereby obtaining 0.75 g of a base generator (12) represented by the following formula (24):

[Chemical formula 27]

Formula (24)

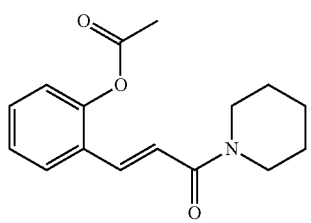

Production Example 13

Synthesis of Base Generator

A compound represented by the formula (14) was obtained in the same manner as Production example 4. In a 100 mL flask, 1.00 g (3.82 mmol) of the compound represented by the formula (14) and 0.57 ml (4.58 mmol, 1.2 eq) of benzyl isocyanate (manufactured by Tokyo Chemical Industry Co., Ltd.) were dissolved in 5 mL of chloroform and stirred for one night. After reaction was completed, water was added thereto. The resultant was extracted with chloroform to obtain an extract. The extract was washed with saturated saline and dried with magnesium sulfate, thereby obtaining 0.21 g of a base generator (13) represented by the following formula (25):

[Chemical formula 28]

Formula (25)

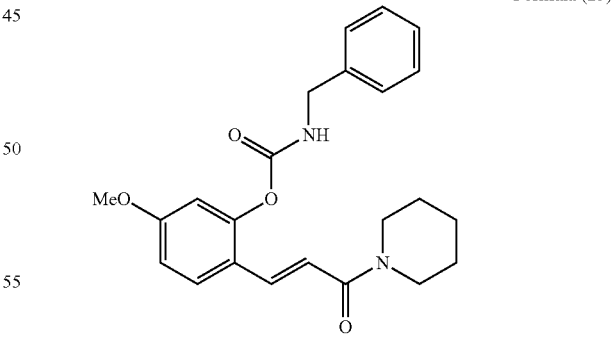

Production Example 14

Synthesis of Base Generator

A compound represented by the formula (14) was obtained in the same manner as Production example 4. In a 100 mL flask, 1.00 g (3.82 mmol) of the compound represented by the formula (14) and 640 mg (4.58 mmol, 1.2 eq) of cyclohexanemethyl isocyanate (manufactured by Sigma-Aldrich Japan K.K.) were dissolved in 5 mL of chloroform and stirred for one night. After reaction was completed, water was added thereto. The resultant was extracted with chloroform to obtain an extract. The extract was washed with saturated saline and dried with magnesium sulfate, thereby obtaining 0.35 g of a base generator (14) represented by the following formula (26):

[Chemical formula 29]

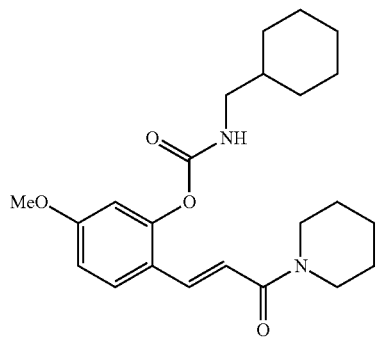

Formula (26)

Production Example 15

Synthesis of Base Generator

A compound represented by the formula (14) was obtained in the same manner as Production example 4. In a 100 mL flask, 1.00 g (3.82 mmol) of the compound represented by the formula (14) was dissolved in chloroform. 310 mg (5.73 mmol, 1.5 eq) of sodium methoxide (manufactured by Tokyo Chemical Industry Co., Ltd.) was added thereto and the resultant was stirred for 10 minutes. After the stirring, 0.69 g (4.01 mmol, 1.05 eq) of 2-nitrobenzyl chloride (manufactured by Tokyo Chemical Industry Co., Ltd.) was added thereto and the resultant was stirred for one night. After reaction was completed, water was added thereto. The resultant was extracted with chloroform to obtain an extract. The extract was washed with saturated saline, dried with magnesium sulfate and purified by silica-gel column chromatography (developing solvent: hexane/ethyl acetate 5/1 to 1/2), thereby obtaining 0.42 g of a base generator (15) represented by the following formula (27):

[Chemical formula 30]

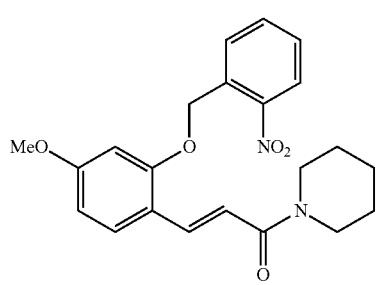

Formula (27)

Production Example 16

Synthesis of Base Generator

In a 500 mL recovery flask, 10.0 g (72.4 mmol) of sesamol (manufactured by Tokyo Chemical Industry Co., Ltd.) and 15.2 g (109 mmol, 1.5 eq) of hexamethylenetetramine (manufactured by Tokyo Chemical Industry Co., Ltd.) were dissolved in 100 ml of trifluoroacetic acid (manufactured by Kanto Chemical Co., Inc.) and reacted at 95° C. for 10 hours. After the reaction was completed, in an ice bath, 200 ml of 1 N hydrochloric acid was added thereto and the resultant was stirred for minutes. After the stirring was completed, the resultant was extracted with chloroform to obtain an extract. The extract was washed with hydrochloric acid and saturated saline, thereby obtaining 2.38 g (14.3 mmol) of 6-hydroxy-3,4-methylenedioxybenzaldehyde.

Synthesis and amidation of cinnamic acid were performed in the same manner as Production example 4, except that 6-hydroxy-3,4-methylenedioxybenzaldehyde was used in place of 2-hydroxy-4-methoxybenzaldehyde. The resultant was purified by silica-gel column chromatography (developing solvent: chloroform/methanol 100/1 to 50/1), thereby obtaining a compound represented by the following chemical formula (28).

A base generator (16) represented by the following formula (29) was obtained in the same manner as Production example 7, except that the compound represented by the chemical formula (28) was used in place of the compound represented by the formula (14).

[Chemical formula 31]

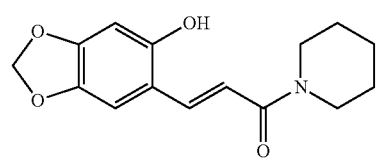

Formula (28)

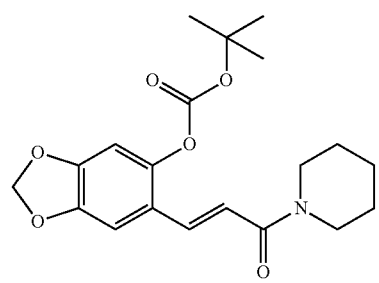

Formula (29)

Production Example 17

Synthesis of Base Generator

In a 500 mL recovery flask, 5.0 g (32.4 mmol) of 3,4-dimethoxyphenol (manufactured by Tokyo Chemical Industry Co., Ltd.) and 18.2 g (130 mmol, 4.0 eq) of hexamethylenetetramine (manufactured by Tokyo Chemical Industry Co., Ltd.) were dissolved in 100 ml of trifluoroacetic acid (manufactured by Kanto Chemical Co., Inc.) and reacted at 100° C. for 24 hours. After the reaction was completed, in an ice bath, 200 ml of 1 N hydrochloric acid was added thereto and the resultant was stirred for 15 minutes. After the stirring was completed, the resultant was extracted with chloroform to obtain an extract. The extract was washed with hydrochloric acid and saturated saline, thereby obtaining 2.17 g (11.0 mmol) of 2-hydroxy-4,5-dimethoxybenzaldehyde.

Synthesis and amidation of cinnamic acid were performed in the same manner as Production example 4, except that 2-hydroxy-4,5-dimethoxybenzaldehyde was used in place of 2-hydroxy-4-methoxybenzaldehyde. The resultant was purified by silica-gel column chromatography (developing solvent: chloroform/methanol 100/1 to 50/1), thereby obtaining a compound represented by the following chemical formula (30).

A base generator (17) represented by the following formula (31) was obtained in the same manner as Production example 7, except that the compound represented by the following formula (30) was used in place of the compound represented by the formula (14).

[Chemical formula 32]

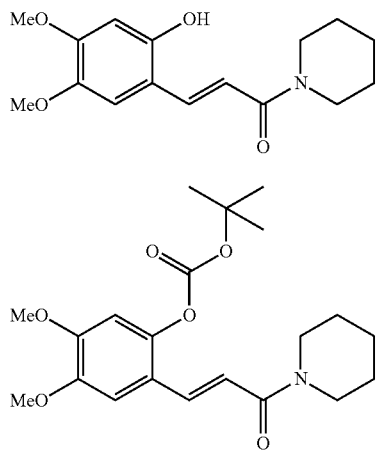

Formula (30)

Formula (31)

Production Example 18

Synthesis of Base Generator

Synthesis and amidation of 3-(1-hydroxy-2-naphthalenyl)-acrylic acid were performed in the same manner as Production example 4, except that 1-hydroxy-2-naphthaldehyde was used in place of 2-hydroxy-4-methoxybenzaldehyde. The resultant was purified by silica-gel column chromatography (developing solvent: chloroform/methanol 100/1 to 50/1), thereby obtaining a compound represented by the following chemical formula (32).

A base generator (18) represented by the following formula (33) was obtained in the same manner as Production example 7, except that the compound represented by the chemical formula (32) was used in place of the compound represented by the formula (14).

[Chemical formula 33]

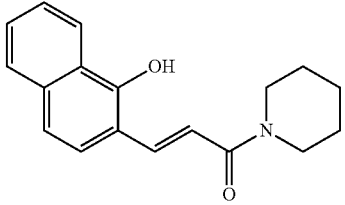

Formula (32)

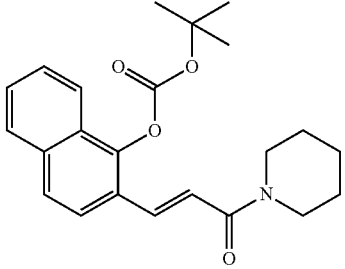

Formula (33)

Production Example 19

Synthesis of Base Generator

In a 200 mL three-necked flask under a nitrogen atmosphere, 3.00 g (21.7 mmol) of 2,4-dihydroxybenzaldehyde (manufactured by Tokyo Chemical Industry Co., Ltd.) and 1.43 g (21.7 mmol) of potassium hydroxide were dissolved in 30 mL of dehydrated ethanol (manufactured by Kanto Chemical Co., Inc.) 4.13 mL (21.7 mmol) of p-toluenesulfonic acid-2-methoxyethyl (manufactured by Tokyo Chemical Industry Co., Ltd.) was gradually added thereto in a dropwise manner and then the resultant was stirred for one night at a reaction temperature of 60° C. After the reaction was completed, the resultant was filtered and subjected to vacuum concentration to exclude ethanol, and 1 N hydrochloric acid was added thereto. The resultant was extracted with ethyl acetate to obtain an extract. The extract was washed with 1 N hydrochloric acid, pure water and saturated saline, and then purified by silica-gel column chromatography (developing solvent: hexane/ethyl acetate 10/1 to 0/1 (volume ratio)), thereby obtaining 1.01 g of an acid derivative A having a —O—(CH$_2$)$_2$—O—CH$_3$ group.

Synthesis and amidation of cinnamic acid were performed in the same manner as Production example 4, except that the acid derivative A having a —O—(CH$_2$)$_2$—O—CH$_3$ group was used in place of 2-hydroxy-4-methoxybenzaldehyde. The resultant was purified by silica-gel column chromatography (developing solvent: chloroform/methanol 100/1 to 50/1), thereby obtaining a compound represented by the following chemical formula (34).

A base generator (19) represented by the following formula (35) was obtained in the same manner as Production example 7, except that the compound represented by the chemical formula (34) was used in place of the compound represented by the formula (14).

[Chemical formula 34]

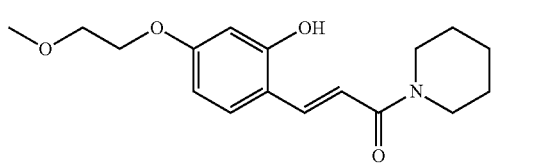

Formula (34)

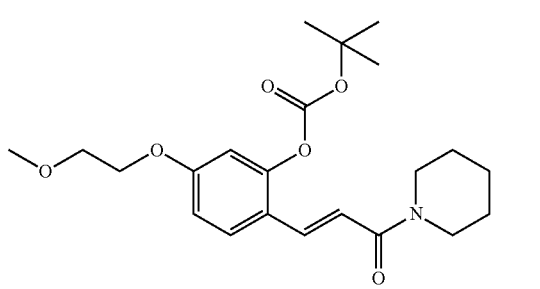

Formula (35)

Production Example 20

Synthesis of Base Generator

Synthesis and amidation of cinnamic acid were performed in the same manner as Production example 4, except that 5-chlorosalicylaldehyde was used in place of 2-hydroxy-4-methoxybenzaldehyde. The resultant was purified by silica-gel column chromatography (developing solvent: chloroform/methanol at 100/1 to 50/1), thereby obtaining a compound represented by the following chemical formula (36).

A base generator (20) represented by the following formula (37) was obtained in the same manner as Production example 7, except that the compound represented by the chemical formula (36) was used in place of the compound represented by the formula (14).

[Chemical formula 35]

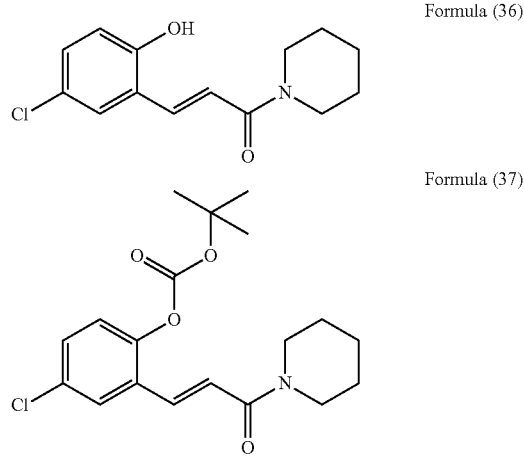

Formula (36)

Formula (37)

Production Example 21

Synthesis of Base Generator

In a 100 mL flask, 2.56 (7.34 mmol) of (triphenylphosphoranylidene)ethyl acetate (manufactured by Tokyo Chemical Industry Co., Ltd.) and 2.56 g (7.34 mmol, 1.0 eq) of 2'-hydroxyacetophenone (manufactured by Tokyo Chemical Industry Co., Ltd.) were dissolved in 20 mL of toluene and stirred at 80° C. for three hours. Completion of reaction was confirmed by thin-layer chromatography. A saturated ammonium chloride aqueous solution was added thereto, and the mixture was extracted with chloroform to obtain an extract. The extract was washed with water and then a saturated ammonium chloride aqueous solution, and then dried with anhydrous magnesium sulfate. After condensation, the resultant was purified by silica-gel column chromatography (developing solvent: hexane/ethyl acetate at 2/1 (volume ratio)).

Then, 15 mL of a 1 N sodium hydroxide aqueous solution was added thereto and the resultant was stirred for one night. After reaction was completed, a reaction solution thus obtained was filtered to exclude a precipitate, and concentrated hydrochloric acid was added thereto in a dropwise manner to acidulate the reaction solution. The reaction solution was then extracted with chloroform to obtain an extract. The extracted was condensed, thereby obtaining 580 mg (3.25 mmol) of a cinnamic acid derivative A.

A compound represented by the following chemical formula (38) was obtained in the same manner as Production example 4, except that amidation of cinnamic acid was performed by using the cinnamic acid derivative A in place of 2-hydroxy-4-methoxycinnamic acid.

A base generator (21) represented by the following formula (39) was obtained in the same manner as Production example 7, except that the compound represented by the chemical formula (38) was used in place of the compound represented by the formula (14).

[Chemical formula 36]

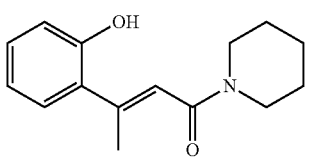

Formula (38)

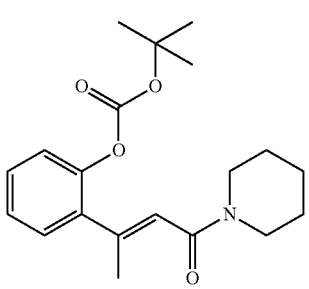

Formula (39)

Production Example 22

Synthesis of Base Generator 5.0 g (27.8 mmol) of 2,4-dihydroxy-cinnamic acid (manufactured by Sigma-Aldrich Japan K.K.) was dissolved in 100 mL of tetrahydrofuran, and 6.4 g (33.3 mmol) of 1-ethyl-3-(3-dimethylaminopropyl)carbodiimide hydrochloride (EDC) (manufactured by Tokyo Chemical Industry Co., Ltd.) was added thereto. After 30 minutes, 3.3 ml (33.3 mmol) of piperidine (manufactured by Tokyo Chemical Industry Co., Ltd.) was added thereto. After reaction was completed, the resultant was dissolved in water and extracted with chloroform to obtain an extract. The extract was washed with a saturated sodium hydrogen carbonate aqueous solution, 1 N hydrochloric acid and then saturated saline. Then, the extract was purified by silica-gel column chromatography (developing solvent: chloroform/methanol 100/1 to 10/1 (volume ratio)), thereby obtaining 3.8 g (15.4 mmol) of a compound represented by the following chemical formula (40).

In a 100 mL flask, 3.00 g (12.1 mmol) of the compound represented by the following chemical formula (40) and 3.26 ml (14.52 mmol, 1.2 eq) of tert-butoxydiphenylchlorosilane (manufactured by Tokyo Chemical Industry Co., Ltd.) were dissolved in 5 mL of dimethylsulfoxide. 2.46 g (36.3 mmol, 2.5 eq) of imidazole (manufactured by Tokyo Chemical Industry Co., Ltd.) was added thereto and the resultant was stirred for one night. After reaction was completed, a 5% sodium hydrogen carbonate solution was added thereto. The resultant was extracted with ethyl acetate to obtain an extract. The extract was washed with saturated saline and dried with magnesium sulfate, thereby obtaining 2.9 g (5.63 mmol) of (E)-3-(4-(tert-butoxydiphenylsilyloxy)-2-hydroxyphenyl)-1-(piperidine-1-yl)prop-2-en-1-on.

In a 100 mL flask, 2.90 g (5.63 mmol) of (E)-3-(4-(tert-butoxydiphenylsilyloxy)-2-hydroxyphenyl)-1-(piperidine-1-yl)prop-2-en-1-on and 1.48 g (6.76 mmol, 1.2 eq) of di-tert-butyl dicarbonate (manufactured by Tokyo Chemical Industry Co., Ltd.) were dissolved in 5 mL of chloroform. A catalytic amount of N,N-dimethyl-4-aminopyridine (manufactured by Tokyo Chemical Industry Co., Ltd.) was added thereto and the resultant was stirred for one night. After reaction was completed, saturated saline was added thereto. The resultant was extracted with ethyl acetate to obtain an extract. The extracted was washed with saturated saline and dried with magnesium sulfate, thereby obtaining 2.10 g (3.4 mmol) of (E)-5-(tert-butoxydiphenylsilyloxy)-2-(3-oxo-3-(piperidine-1-yl)prop-1-enyl)phenyltert-butyl carbonate.

In a 100 mL flask, 2.00 g (3.24 mmol) of (E)-5-(tert-butoxydiphenylsilyloxy)-2-(3-oxo-3-(piperidine-1-yl)prop-1-enyl)phenyltert-butyl carbonate was added to 10 ml of tetrabutylammonium fluoride (a 1 mol/L tetrahydrofuran solution manufactured by Tokyo Chemical Industry Co., Ltd.) and stirred for one night. After reaction was completed, the resultant was washed with water and purified by silica-gel column chromatography (developing solvent: hexane/ethyl acetate 10/1 to 1/1), thereby obtaining 1.03 g of a base generator (22) represented by the following formula (41).

[Chemical formula 37]

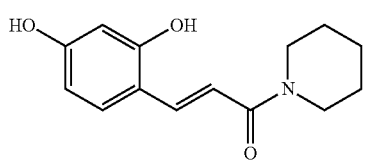

Formula (40)

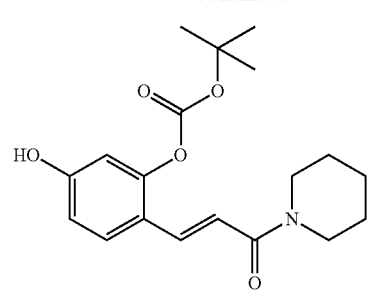

Formula (41)

Production Example 23

Synthesis of Base Generator

Synthesis and amidation of cinnamic acid were performed in the same manner as Production example 4, except that 2-hydroxy-5-nitro-m-anisaldehyde was used in place of 2-hydroxy-4-methoxybenzaldehyde. The resultant was purified by silica-gel column chromatography (developing solvent: hexane/ethyl acetate 10/1 to 0/1 (volume ratio)), thereby obtaining a compound represented by the following chemical formula (42).

A base generator (23) represented by the formula (43) was obtained in the same manner as Production example 7, except that the compound represented by the chemical formula (42) was used in place of the compound represented by the formula (14).

[Chemical formula 38]

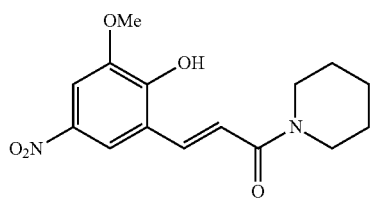

Formula (42)

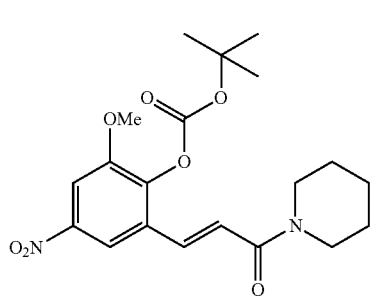

Formula (43)

Production Example 24

Synthesis of Base Generator

In a 500 mL recovery flask, 10.0 g (72.4 mmol) of 4-mercaptophenol (manufactured by Aldrich Inc.) and 16.6 g (119 mmol, 1.5 eq) of hexamethylenetetramine (manufactured by Tokyo Chemical Industry Co., Ltd.) were dissolved in 100 ml of trifluoroacetic acid (manufactured by Kanto Chemical Co., Inc.) and reacted at 95° C. for 10 hours. After the reaction was completed, 200 ml of 1 N hydrochloric acid was added thereto and the resultant was stirred for 15 minutes. After the stirring was completed, the resultant was extracted with chloroform to obtain an extract. The extract was washed with hydrochloric acid and saturated saline, thereby obtaining 2.05 g (13.3 mmol) of 2-hydroxy-4-mercaptobenzaldehyde.

Synthesis and amidation of cinnamic acid were performed in the same manner as Production example 4, except that 2-hydroxy-4-mercaptobenzaldehyde was used in place of 2-hydroxy-4-methoxybenzaldehyde. The resultant was purified by silica-gel column chromatography (developing solvent: hexane/ethyl acetate 10/1 to 0/1 (volume ratio)), thereby obtaining a compound represented by the following chemical formula (44).

A base generator (24) represented by the following formula (45) was obtained in the same manner as Production example 7, except that the compound represented by the chemical formula (44) was used in place of the compound represented by the formula (14).

[Chemical formula 39]

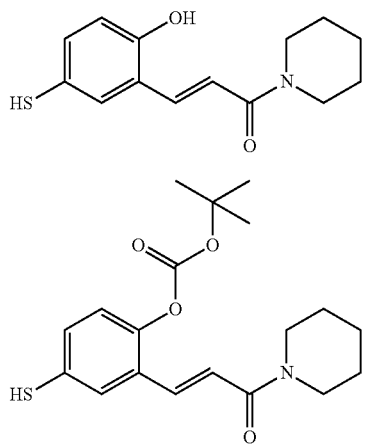

Formula (44)

Formula (45)

Production Example 25

Synthesis of Base Generator

In a 500 mL recovery flask, 5.0 g (36.5 mmol) of 3-methyl-4-nitrosophenol (manufacture by Aldrich Inc.) and 7.63 g (54.7 mmol, 1.5 eq) of hexamethylenetetramine (manufactured by Tokyo Chemical Industry Co., Ltd.) were dissolved in 100 ml of trifluoroacetic acid (manufactured by Kanto Chemical Co., Inc.) and reacted at 95° C. for 10 hours. After the reaction was completed, in an ice bath, 200 ml of 1 N hydrochloric acid was added thereto and the resultant was stirred for 15 minutes. After the stirring, the resultant was extracted with chloroform to obtain an extract. The extract was washed with hydrochloric acid and unsaturated saline, thereby obtaining 1.51 g (9.13 mmol) of 2-hydroxy-4-methyl-5-nitroso-benzaldehyde.

Synthesis and amidation of cinnamic acid were performed in the same manner as Production example 4, except that 2-hydroxy-4-methyl-5-nitroso-benzaldehyde was used in place of 2-hydroxy-4-methoxybenzaldehyde. The resultant was purified by silica-gel column chromatography (developing solvent: hexane/ethyl acetate 10/1 to 0/1 (volume ratio)), thereby obtaining a compound represented by the following chemical formula (46).

A base generator (25) represented by the following formula (47) was obtained in the same manner as Production example 7, except that the compound represented by the chemical formula (46) was used in place of the compound represented by the formula (14).

[Chemical formula 40]

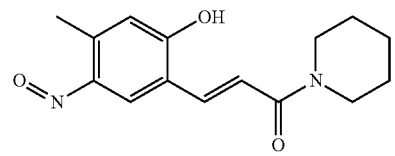

Formula (46)

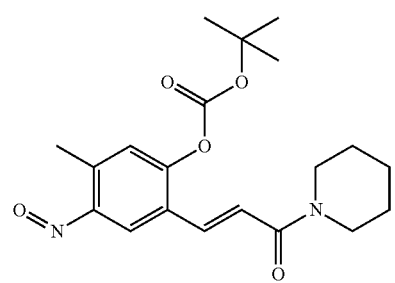

Formula (47)

Production Example 26

Synthesis of Base Generator

A base generator (26) represented by the following formula (48) was obtained in the same manner as Production example 5, except that diethylamine was used in place of piperidine as the base used for amidation.

[Chemical formula 41]

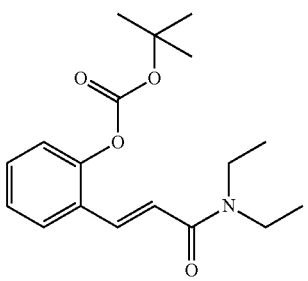

Formula (48)

Production Example 27

Synthesis of Base Generator)

A base generator (27) represented by the following formula (49) was obtained in the same manner as Production example 5, except that 5-amino-1-pentanol was used in place of piperidine as the base used for amidation.

[Chemical formula 42]

Formula (49)

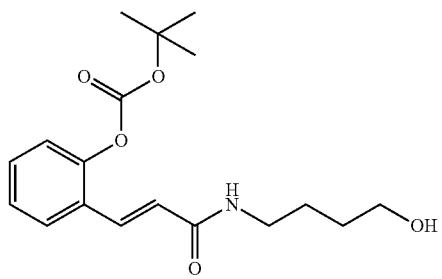

Production Example 28

Synthesis of Base Generator)

A base generator (28) represented by the following formula (50) was obtained in the same manner as Production example 5, except that n-octylamine was used in place of piperidine as the base used for amidation.

[Chemical formula 43]

Formula (50)

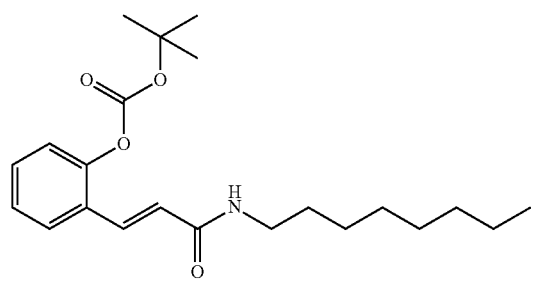

Comparative Production Example 1

Synthesis of Comparative Base Generator (1)

In a 100 mL flask, 2.00 g of potassium carbonate was added to 15 mL of methanol. In a 50 mL flask, 2.19 g (5.1 mmol) of ethoxycarbonylmethyl(triphenyl)phosphonium bromide and 1.0 g (5.1 mmol) of 2,4,5-trimethoxybenzaldehyde were dissolved in 10 mL of methanol. The resultant was gradually added to a well-stirred potassium carbonate solution in a dropwise manner. After stirring the resultant for 3 hours, completion of reaction was confirmed by thin-layer chromatography. The resultant was filtered to exclude potassium carbonate and subjected to vacuum concentration. After the concentration, 50 mL of a 1 N sodium hydroxide aqueous solution was added thereto and the resultant was stirred for one hour. After reaction was completed, a reaction solution thus obtained was filtered to exclude triphenylphosphine oxide, and concentrated hydrochloric acid was added thereto in a dropwise manner to acidulate the reaction solution. A precipitate thus produced was collected by filtration and washed with a small amount of chloroform, thereby obtaining 2,4,5-trimethoxycinnamic acid. Then, in a 100 mL three-necked flask, 500 mg (2.8 mmol) of 2,4,5-trimethoxycinnamic acid was dissolved in 40 mL of dehydrated tetrahydroxyfuran, and 0.64 g (3.3 mmol) of 1-ethyl-3-(3-dimethylaminopropyl)carbodiimide hydrochloride (EDC) was added thereto. After 30 minutes, 0.38 ml (3.3 mmol) of cyclohexylamine was added thereto. After reaction was completed, a reaction solution thus obtained was condensed and dissolved in water. The resulting solution was extracted with diethyl ether to obtain an extract. The extract was washed with a saturated sodium hydrogen carbonate aqueous solution, 1 hydrochloric acid and saturated saline, and then purified by silica-gel column chromatography (developing solvent: chloroform/methanol 100/1 to 10/1 (volume ratio)), thereby obtaining 210 mg of a comparative base generator (1) represented by the following chemical formula (51):

[Chemical formula 44]

Formula (51)

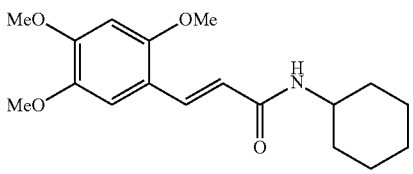

Comparative Production Example 2

Synthesis of Comparative Base Generator (2)

A compound represented by the formula (10) was produced in the same manner as Production example 1 and made into a comparative base generator (2) having no protecting group.

<Evaluation of Base Generators>

The synthesized base generators were measured for the following properties for evaluation.

(1) Molar Absorbance Coefficient

Each of the base generators (1) to (28) was dissolved in acetonitrile to have a concentration of $1 \times 10^{-4}$ mol/L. A quartz cell (optical path 10 mm) was filled with the resulting solution to measure the absorbance. Molar absorbance coefficient E is the absorbance of a solution divided by the thickness of an absorbing layer and the molar concentration of a solute. The results are obtained in Table 1.

TABLE 1

| | Molar absorbance coefficient ($\epsilon$) | |
|---|---|---|
| | 365 nm | 405 nm |
| Base generator 1 | 19 | 10 |
| Base generator 2 | 50 | 0 |
| Base generator 3 | 20 | 0 |
| Base generator 4 | 260 | 0 |
| Base generator 5 | 10 | 0 |
| Base generator 6 | 230 | 10 |
| Base generator 7 | 10 | 0 |
| Base generator 8 | 20 | 0 |
| Base generator 9 | 10 | 0 |
| Base generator 10 | 20 | 0 |
| Base generator 11 | 30 | 0 |
| Base generator 12 | 10 | 0 |
| Base generator 13 | 10 | 0 |
| Base generator 14 | 10 | 0 |
| Base generator 15 | 10 | 0 |
| Base generator 16 | 110 | 10 |

TABLE 1-continued

|  | Molar absorbance coefficient (ε) | |
| --- | --- | --- |
|  | 365 nm | 405 nm |
| Base generator 17 | 80 | 0 |
| Base generator 18 | 50 | 0 |
| Base generator 19 | 10 | 0 |
| Base generator 20 | 10 | 0 |
| Base generator 21 | 0 | 0 |
| Base generator 22 | 20 | 0 |
| Base generator 23 | 10 | 0 |
| Base generator 24 | 10 | 0 |
| Base generator 25 | 10 | 0 |
| Base generator 26 | 10 | 0 |
| Base generator 27 | 10 | 0 |
| Base generator 28 | 10 | 0 |

(2) Base Generating Ability and Deprotection Temperature

Two 1 mg samples were taken from each of the base generators (1) to (28) and comparative base generator (1). Each sample was dissolved in dimethyl-d6 sulfoxide in a quartz NMR tube. One of the tubes was exposed to 2 J/cm² of light (in terms of i-line) from a high pressure mercury lamp, while the other was not exposed to light. Each sample was measured for $^1$H NMR to obtain the rate of isomerization.

The base generators (1) to (28) were isomerized when exposed to light at 2 J/cm² (in terms of i-line).

The isomerized samples were heated at a heating rate of 10° C./min. In the base generator (1), deprotection gradually started at a temperature of 60° C., and when heated 100° C. or more, the sample was cyclized and generation of a base was confirmed with this. The deprotection temperature and cyclization temperature of each base generator are shown in Table 2. When exposed to light, the base generator (15) having an o-nitrobenzyl group as the protecting group was deprotected and isomerized at the same time. As a result of heating deprotected and isomerized samples, cyclization was observed when heated at 100° C. or more and base generation was confirmed with this. No deprotection and cyclization was observed in the base generator (15) having an o-nitrobenzyl group only by heating the same.

TABLE 2

| | Deprotection temperature (° C.) | Cyclization temperature (° C.) |
| --- | --- | --- |
| Base generator 1 | 60 | 100 |
| Base generator 2 | 40 | 100 |
| Base generator 3 | 80 | 120 |
| Base generator 4 | 160 | 160 |
| Base generator 5 | 130 | 160 |
| Base generator 6 | 160 | 160 |
| Base generator 7 | 130 | 160 |
| Base generator 8 | 130 | 160 |
| Base generator 9 | 130 | 160 |
| Base generator 10 | 130 | 160 |
| Base generator 11 | 160 | 160 |
| Base generator 12 | 160 | 160 |
| Base generator 13 | 160 | 160 |
| Base generator 14 | 160 | 160 |
| Base generator 15 | Not deprotected | 100 |
| Base generator 16 | 130 | 160 |
| Base generator 17 | 130 | 160 |
| Base generator 18 | 130 | 160 |
| Base generator 19 | 130 | 160 |
| Base generator 20 | 130 | 160 |
| Base generator 21 | 130 | 160 |
| Base generator 22 | 130 | 160 |
| Base generator 23 | 130 | 160 |
| Base generator 24 | 130 | 160 |
| Base generator 25 | 130 | 160 |
| Base generator 26 | 130 | 160 |
| Base generator 27 | 130 | 160 |
| Base generator 28 | 130 | 160 |
| Comparative base generator 1 | Not deprotected | Not cyclized |

The comparative base generator (1) was isomerized by exposure to 2 J/cm² of light (in terms of i-line). The isomerized sample was heated at a heating rate of 10° C./min; however, no deprotection and cyclization occurred and no base generation was observed.

Among the base generators (1) to (28), the base generator having the protecting groups of the formula (2-1) or (2-3) and a substituent at any of $R^5$ to $R^8$ was found to have high sensitivity. In the case of the base generator having a protecting group having a carbonyl group, such as the protecting groups of the formulae (2-2), (2-4) and (2-6), the absorption wavelength of the base generator is shifted to a short wavelength side, so that the sensitivity of the same was likely to be decreased. Therefore, in the case of such a protecting group, it was found to be effective to deprotect the protecting group and increase the sensitivity before exposure to electromagnetic radiation.

Also, as the substituents at $R^5$ to $R^8$, the following groups were found to particularly increase sensitivity and to be effective: a methoxy group, a hydroxyl group, a dimethoxy type as represented by the formula (31), a type which has a —O—X—O— part as represented by the formula (28), a naphthalene ring-forming type as represented by the formula (31), and a —OROR type as represented by the formula (34).

Example 1

Production of Photosensitive Resin Composition (1)

The photosensitive resin composition (1) having the following composition was produced using the base generator (1). The base generator (1) dissolved in an epoxy resin in a solvent-free state.

Epoxy resin (jER828 manufactured by Japan Epoxy Resins Co., Ltd.): 100 parts by weight Base generator (1): 15 parts by weight The photosensitive resin composition (1) was spin-coated onto a glass so as to have a final film thickness of 0.5 μm and dried on a hot plate at 80° C. for 15 minutes, thereby obtaining two coating films of the photosensitive resin composition. The whole surface of one of the films was exposed to 10 J/cm² of light from a high pressure mercury lamp using a manual exposure device. Then, the coating films were heated at 160° C. for 30 minutes. The heated coating films were immersed in a mixed solution of isopropanol and chloroform (isopropanol:chloroform=4:1 (volume ratio)) at room temperature for 10 minutes. As a result, the coating film exposed and then heated was not dissolved in the mixed solution, so that the epoxy resin was found to be cured. On the other hand, the coating film heated but not exposed was dissolved in the mixed solution.

Examples 2 to 28

Production of Photosensitive Resin Compositions (2) to (28)

In Examples 2 to 28, the photosensitive resin compositions (2) to (28) were produced in the same manner as Example 1, except that the base generators (2) to (28) were used in place of the base generator (1).

Two coating films were produced from each of the photosensitive resin compositions (2) to (28) in the same manner as Example 1. As to the photosensitive resin compositions (2) to (28), as with Example 1, the coating film exposed and then heated was not dissolved in the mixed solution, so that the epoxy resin was found to be cured. On the other hand, the coating film heated but not exposed was dissolved in the mixed solution.

Example 29

Production of a Coating Film Using Photosensitive Resin Composition (9)

The photosensitive resin composition (9) containing the base generator (9) was spin-coated onto a glass so as to have a final thickness of 0.5 μm and dried on a hot plate at 160° C. for one minute, thereby obtaining two coating films of the photosensitive resin composition.

The whole surface of one of the films was exposed to 1 J/cm$^2$ of light from a high pressure mercury lamp using a manual exposure device. Then, the coating films were heated at 100° C. for 60 minutes. The heated coating films were immersed in a mixed solution of isopropanol and chloroform (isopropanol:chloroform=4:1 (volume ratio)) at room temperature for 10 minutes. As a result, the coating film exposed and then heated was not dissolved in the mixed solution, so that the epoxy resin was found to be cured. On the other hand, the coating film heated but not exposed was dissolved in the mixed composition.

The protecting groups were not deprotected by heating (as in Examples 1 to 28) on a hot plate at 80° C. for 15 minutes upon forming the coating films. In Example 29, however, by heating at 160° C. for one minute, the protecting group was deprotected before the exposure to light. Therefore, the sensitivity was increased, and it was possible to cure the film with a small exposure amount of 1 J/cm$^2$.

Comparative Example 1

Production of Comparative Photosensitive Resin Composition (1)

The comparative photosensitive resin composition (1) was produced in the same manner as Example 1, except that the comparative base generator (2) was used in place of the base generator (1). While the base generators (1) to (28) of Examples (1) to (28) dissolved in the epoxy resin in a solvent-free state, the comparative base generator (2) did not dissolve in the epoxy resin in a solvent-free state and was suspended.

Synthesis Example 1

Synthesis of Polyimide Precursor

Into a 300 mL three-necked flask, 10.0 g (50 mmol) of di(4-aminophenyl)ether was poured and dissolved in 105.4 mL of dehydrated N,N-dimethylacetamide (DMAc). Under a nitrogen flow, the mixture was stirred while cooling in an ice bath. 14.7 g (50 mmol) of 3,3',4,4'-biphenyltetracarboxylic dianhydride was gradually added thereto. After reaction was completed, the resultant was stirred for five hours in an ice bath. Dehydrated diethyl ether was used to cause reprecipitation in the solution and a precipitate thus obtained was dried under a reduced pressure for 17 hours, thereby obtaining a polyamide acid having a weight average molecular weight of 10,000 (polyimide precursor (1)) quantitatively as a white solid.

Example 30

Production of Photosensitive Resin Composition (29)

The photosensitive resin composition (29) having the following composition was produced using the base generator (4).

Polyimide precursor (1): 85 parts by weight
Base generator (4): 15 parts by weight
Solvent (N-methylpyrrolidone (NMP)): 843 parts by weight The photosensitive resin composition (29) was spin-coated onto a glass so as to have a final film thickness of 1.0 μm and dried on a hot plate at 80° C. for 15 minutes, thereby obtaining three coating films of the photosensitive resin composition. The whole surface of one of the films was exposed to 10 J/cm$^2$ of light from a high pressure mercury lamp using a manual exposure device. One of the films was exposed to 10 J/cm$^2$ of light in a pattern from a high pressure mercury lamp using a manual exposure device. Then, the coating films were heated at 160° C. for 10 minutes. The heated coating films were immersed in a mixed solution of a 2.38 wt % tetramethylammonium hydroxide aqueous solution and isopropanol at 9:1. As a result, the coating film exposed and then heated was not dissolved in NMP, so that the polyimide precursor was found to be cured. On the other hand, the coating film heated but not exposed was dissolved in NMP. As for the coating film exposed to light in a pattern, a pattern in which an exposed region was not dissolved in the developer and remained, was obtained. In addition, the patterned coating film was heated at 350° C. for one hour for imidization. As a result, the photosensitive resin composition of the present invention was found to be able to form an excellent pattern.

Example 31

Production of Photosensitive Resin Composition (30)

The photosensitive resin composition (30) was prepared, the composition comprising: 100 parts by weight or hexamethylene diisocyanate (manufactured by Kanto Chemical Co., Inc.) as an isocyanato resin, 150 parts by weight of polytetrahydrofuran (manufactured by Aldrich Inc.) as a resin having a hydroxyl group, 10 parts by weight of the base generator (1) and 500 parts by weight of tetrahydrofuran.

The photosensitive resin composition (30) was spin-coated onto a chrome plated glass so as to have a final film thickness of 0.5 μm and dried on a hot plate at 60° C. for five minutes, thereby obtaining one coating film of the photosensitive resin composition. The whole surface of the film was exposed to 1 J/cm$^2$ of light from a high pressure mercury lamp using a manual exposure device. Then, the coating film was heated at 120° C. for 10 minutes and cooled to room temperature. As a result, a low elastic solid was obtained, so that curing of the isocyanato and hydroxyl groups was found to proceed.

Synthesis Example 2

Synthesis of Metal Alkoxide Condensate

Into a 100 ml flask equipped with a condenser tube, g of phenyltriethoxysilane, 10 g of triethoxysilane, 0.05 g of ammonia water, 5 ml of water and 50 ml of propylene glycol monomethyl ether acetate were poured. The mixed solution was stirred with an anchor-type mechanical stirrer and reacted at 70° C. for 6 hours with a heating mantle. Then, ethanol and residual water produced by condensation reaction with water were removed therefrom with an evaporator. After the reaction was completed, the flask was left until it reached room temperature, thereby producing a condensate of alkoxysilane (alkoxysilane condensate (1)).

Example 32

Production of Photosensitive Resin Composition (31)

After 100 parts by weight of the alkoxysilane condensate (1) obtained in Synthesis example 2 was mixed with 10 parts by weight of the base generator (1), the mixture was dissolved in 500 parts by weight of tetrahydrofuran (solvent), thereby producing a photosensitive resin composition (31).

The photosensitive resin composition (31) was spin-coated onto two chrome plated glasses so as to have a final film thickness of 0.5 μm and dried on a hot plate at 80° C. for five minutes, thereby obtaining two coating films of the photosensitive resin composition. The whole surface of one of the films was exposed to 10 J/cm$^2$ of light from a high pressure mercury lamp using a manual exposure device. Then, the coating films were heated at 120° C. for 30 minutes. Before and after the heating, the samples were subjected to infrared absorption spectral measurement. As a result, the sample of the exposed film after the heating showed a peak at 1020 cm$^{-1}$ which is assigned to a Si—O—Si bond that indicates occurrence of polymerization, and the number of peaks at 2850 cm$^{-1}$ and 850 cm$^{-1}$ which is assigned to Si—OCH$_3$ that indicates raw materials was decreased than those of the same before the heating. The sample of the unexposed coating film after the heating showed a peak at 1020 cm$^{-1}$ which is assigned to a Si—O—Si bond that indicates occurrence of polymerization. Compared to the exposed coating film, however, the peak was small. From these results, it is now clear that when the base generator of the present invention is used, a base is generated by exposure to light, and polymerization of alkoxysilane condensate is promoted.

The invention claimed is:

1. A base generator which is represented by the following chemical formula (1) and generates a base by exposure to electromagnetic radiation and heating:

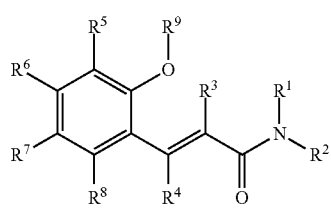

Formula (1)

wherein R$^1$ and R$^2$ are each independently a hydrogen or an organic group and may be the same or different; R$^1$ and R$^2$ may be bound to form a cyclic structure which may contain a heteroatom; at least one of R$^1$ and R$^2$ is an organic group; R$^3$ and R$^4$ are each independently a hydrogen, a halogen, a hydroxyl group, a mercapto group, a sulfide group, a silyl group, a silanol group, a nitro group, a nitroso group, a sulfino group, a sulfa group, a sulfonato group, a phosphino group, a phosphinyl group, a phosphono group, a phosphonato group or an organic group and may be the same or different; R$^5$, R$^6$, R$^7$ and R$^8$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, ammonio group or an organic group and may be the same or different; two or more of R$^5$, R$^6$, R$^7$ and R$^8$ may be bound to form a cyclic structure which may contain a heteroatom; and R$^9$ is a protecting group which can be deprotected by at least one of heating and exposure to electromagnetic radiation, and R$^9$ is one or more kinds selected from the group consisting of organic groups represented by the following formulae (2-1), (2-2), (2-3) and (2-6):

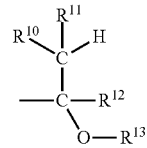

Formula (2-1)

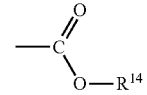

Formula (2-2)

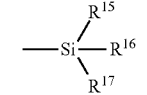

Formula (2-3)

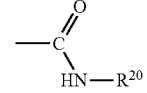

Formula (2-6)

wherein R$^{10}$, R$^{11}$ and R$^{12}$ in the formula (2-1) are each independently a hydrogen, a halogen or an organic group; R$^{13}$ in the formula (2-1) is an organic group; R$^{10}$, R$^{11}$, R$^{12}$ and R$^{13}$ may be bound to form a cyclic structure; R$^{14}$ in the formula (2-2) is an organic group; R$^{15}$, R$^{16}$ and R$^{17}$ in the formula (2-3) are each independently a hydrogen, a halogen or an organic group; and R$^{20}$ in the formula (2-6) is an organic group.

2. A photosensitive resin composition comprising a polymer precursor in which reaction into a final product is promoted by a basic substance or by heating in the presence of a basic substance, and a base generator which is represented by the following chemical formula (1) and generates a base by exposure to electromagnetic radiation and heating:

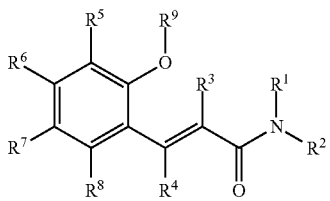

Formula (1)

wherein $R^1$ and $R^2$ are each independently a hydrogen or an organic group and may be the same or different; $R^1$ and $R^2$ may be bound to form a cyclic structure which may contain a heteroatom; at least one of $R^1$ and $R^2$ is an organic group; $R^3$ and $R^4$ are each independently a hydrogen, a halogen, a hydroxyl group, a mercapto group, a sulfide group, a silyl group, a silanol group, a nitro group, a nitroso group, a sulfino group, a sulfa group, a sulfonato group, a phosphino group, a phosphinyl group, a phosphano group, a phosphonato group or an organic group and may be the same or different; $R^5$, $R^6$, $R^7$ and $R^8$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonia group or an organic group and may be the same or different; two or more of $R^5$, $R^6$, $R^7$ and $R^8$ may be bound to form a cyclic structure which may contain a heteroatom; and $R^9$ is a protecting group which can be deprotected by at least one of heating and exposure to electromagnetic radiation.

3. The photosensitive resin composition according to claim 2, wherein the polymer precursor comprises one or more kinds selected from the group consisting of a compound having an epoxy group, isocyanate group, oxetane group or thiirane group, a polymer having an epoxy group, isocyanate group, oxetane group or thiirane group, a polysiloxane precursor, a polyimide precursor and a polybenzoxazole precursor.

4. The photosensitive resin composition according to claim 2, wherein the polymer precursor is soluble in basic solutions.

5. The photosensitive resin composition according to claim 2, wherein the polymer precursor is a polyimide precursor or polybenzoxazole precursor.

6. The photosensitive resin composition according to claim 2, which is usable as a paint, a printing ink, a sealing agent or an adhesive, or as a material for forming display devices, semiconductor devices, electronic components, microelectromechanical systems, stereolithography products, optical elements or building materials.

7. A pattern forming material comprising any of the photosensitive resin compositions defined by claim 2.

8. A pattern forming method by forming a coating film or molded body with any of the photosensitive resin compositions defined by claim 2, exposing the coating film or molded body to electromagnetic radiation in a predetermined pattern, heating the coating film or molded body after or at the same time as the exposure to change the solubility of the exposed region, and then developing the coating film or molded body.

9. An article selected from a printed product, a paint, a sealing agent, an adhesive, a display device, a semiconductor device, an electronic component, a microelectromechanical system, a stereolithography product, an optical element or a building material, at least part of each of which articles comprising a photosensitive resin composition or a cured product thereof, the photosensitive resin composition comprising a polymer precursor in which reaction into a final product is promoted by a basic substance or by heating in the presence of a basic substance, and a base generator which is represented by the following chemical formula (1) and generates a base by exposure to electromagnetic radiation and heating, and the cured product thereof comprising the base generator represented by the following formula (1):

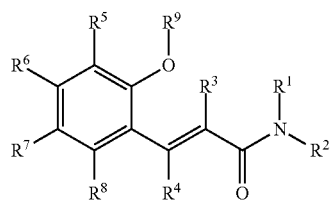

Formula (1)

wherein $R^1$ and $R^2$ are each independently a hydrogen or an organic group and may be the same or different; $R^1$ and $R^2$ may be bound to form a cyclic structure which may contain a heteroatom; least one of $R^1$ and $R^2$ is an organic group; $R^3$ and $R^4$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group or an organic group and may be the same or different; $R^5$, $R^6$, $R^7$ and $R^8$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonia group or an organic group and may be the same or different; two or more of $R^5$, $R^6$, $R^7$ and $R^8$ may be bound to form a cyclic structure which may contain a heteroatom; and $R^9$ is a protecting group which can be deprotected by at least one of heating and exposure to electromagnetic radiation.

10. A base generator which is represented by the following chemical formula (1) and generates a base by exposure to electromagnetic radiation and heating:

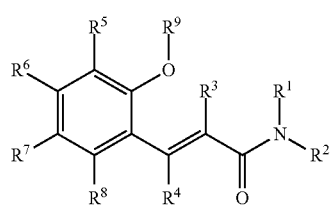

Formula (1)

wherein $R^1$ and $R^2$ are each independently a hydrogen or an organic group and may be the same or different; $R^1$ and $R^2$ may be bound to form a cyclic structure which may contain a heteroatom; at least one of $R^1$ and $R^2$ is an organic group; $R^3$ and $R^4$ are each independently a hydrogen, a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group or an organic group and may be the same or different; $R^5$, $R^6$, $R^7$ and $R^8$ are each independently a hydrogen, a halogen, a hydroxyl group, a mercapto group, a sulfide croup, a silyl group, a silanol group, a nitro group, a nitroso group, a sulfino group, a sulfa group, a sulfonato group, a phosphino group, a phosphinyl group, a phosphono group, a phosphonato group, an amino group, an ammonia group or an organic group and may be the same or different; two or more of $R^5$, $R^6$, $R^7$ and $R^8$ may be bound to form a cyclic structure which may contain a heteroatom; $R^1$ to $R^8$ satisfy at least one of the following (i) and (ii):

(i) at least one of $R^3$ and $R^4$ is a halogen, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group or an organic group;

(ii) at least one of $R^5$, $R^6$, $R^7$ and $R^8$ is a halogen, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, an alkyl group having 2 to 20 carbon atoms, a cycloalkyl group, a cycloalkenyl group, an aryloxyalkenyl group, an aryloxyalkyl group, an aralkyl group, an alkyl group having a cyano group, an alkyl group having a hydroxyl group, an alkoxy group having 2 to 20 carbon atoms, an amide group, an alkylthio group, an acyl group, an ester group, an aryl group or a cyano group; and $R^5$ and $R^6$ may be bound to form a cyclic structure which may contain a heteroatom or $R^7$ and $R^8$ may be bound to form a cyclic structure which may contain a heteroatom;

and $R^9$ is a protecting group which can be deprotected by at least one of heating and exposure to electromagnetic radiation, and $R^9$ is an organic group represented by the following formula (2-4):

Formula (2-4)

wherein $R^{18}$ is an organic group.

* * * * *